US012617767B2

(12) United States Patent
Reddy et al.

(10) Patent No.: US 12,617,767 B2
(45) Date of Patent: May 5, 2026

(54) CRYSTALLINE FORMS OF SOMATOSTATIN MODULATORS

(71) Applicant: Crinetics Pharmaceuticals, Inc., San Diego, CA (US)

(72) Inventors: Jayachandra P. Reddy, San Diego, CA (US); Yuxin Zhao, San Diego, CA (US); Mahmoud Mirmehrabi, Halifax (CA); Alex Mayo, Halifax (CA); Madhukar Kota, San Diego, CA (US); Uttam Dash, San Diego, CA (US); Vijaykumar Umesh Naik, San Diego, CA (US); Praveen Kumar Bandaru, San Diego, CA (US); Yuanqing Fang, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 1145 days.

(21) Appl. No.: 17/626,777

(22) PCT Filed: Jul. 15, 2020

(86) PCT No.: PCT/US2020/042119

§ 371 (c)(1),
(2) Date: Jan. 12, 2022

(87) PCT Pub. No.: WO2021/011641

PCT Pub. Date: Jan. 21, 2021

(65) Prior Publication Data

US 2022/0267295 A1 Aug. 25, 2022

Related U.S. Application Data

(60) Provisional application No. 62/875,285, filed on Jul. 17, 2019.

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .......................... C07D 401/04; C07B 2200/13
See application file for complete search history.

(56) References Cited

U.S. PATENT DOCUMENTS 7,115,634 B2 10/2006 Thurieau et al.
7,648,984 B2 1/2010 Miller et al.
(Continued)

FOREIGN PATENT DOCUMENTS

CA 2925651 A1 4/2015
CN 1627945 A 6/2005
(Continued)

OTHER PUBLICATIONS

Co-pending U.S. Appl. No. 18/952,194, filed Nov. 19, 2024.
(Continued)

*Primary Examiner* — Andrew D Kosar
*Assistant Examiner* — John D McAnany
(74) *Attorney, Agent, or Firm* — WILSON SONSINI GOODRICH & ROSATI

(57) ABSTRACT

Described herein are pharmaceutically acceptable salts of a somatostatin modulator, crystalline forms of the pharmaceutically acceptable salts of the somatostatin modulator, methods of making such salts and crystalline forms, pharmaceutical compositions and medicaments comprising such salts and crystalline forms, and methods of using such salts and crystalline forms in the treatment of conditions, diseases, or disorders that would benefit from modulation of somatostatin activity.

16 Claims, 23 Drawing Sheets

(56) References Cited

U.S. PATENT DOCUMENTS

| | | | |
|---|---|---|---|
| 7,767,817 B2 | 8/2010 | Wang et al. | |
| 9,120,749 B2 | 9/2015 | Matsuo et al. | |
| 9,309,222 B2 | 4/2016 | Leonard et al. | |
| 9,643,951 B2 | 5/2017 | Ishida et al. | |
| 9,896,432 B2 | 2/2018 | Zhao et al. | |
| 9,902,703 B2 | 2/2018 | Zhao et al. | |
| 9,957,267 B2 | 5/2018 | Zhu et al. | |
| 10,351,547 B2 | 7/2019 | Zhao et al. | |
| 10,464,918 B2 | 11/2019 | Reddy et al. | |
| 10,597,377 B2 | 3/2020 | Zhao et al. | |
| 10,696,689 B2 | 6/2020 | Han et al. | |
| 10,875,839 B2 | 12/2020 | Zhao et al. | |
| 10,889,561 B2 | 1/2021 | Reddy et al. | |
| 11,072,598 B2 | 7/2021 | Han et al. | |
| 11,266,641 B1 | 3/2022 | Burke et al. | |
| 11,957,674 B2 | 4/2024 | Burke et al. | |
| 2003/0153553 A1 | 8/2003 | Mattei et al. | |
| 2005/0009815 A1 | 1/2005 | Devita et al. | |
| 2007/0225366 A1 | 9/2007 | Xiang et al. | |
| 2009/0258853 A1 | 10/2009 | Eastman et al. | |
| 2010/0256184 A1 | 10/2010 | Rowe et al. | |
| 2012/0329741 A1 | 12/2012 | Oyelere et al. | |
| 2014/0038990 A1 | 2/2014 | Buschmann et al. | |
| 2014/0228417 A1 | 8/2014 | Mizhiritskii et al. | |
| 2014/0315924 A1* | 10/2014 | Schwab | A61P 31/12 544/364 |
| 2015/0232478 A1 | 8/2015 | Ishida et al. | |
| 2015/0239900 A1 | 8/2015 | Li et al. | |
| 2015/0284337 A1 | 10/2015 | Aubele et al. | |
| 2017/0096422 A1 | 4/2017 | Tsukamoto et al. | |
| 2018/0016252 A1 | 1/2018 | Zhao et al. | |
| 2019/0211008 A1 | 7/2019 | Gallina et al. | |
| 2019/0382367 A1 | 12/2019 | Zhao et al. | |
| 2020/0190053 A1 | 6/2020 | Zhao et al. | |
| 2021/0087165 A1 | 3/2021 | Reddy et al. | |
| 2021/0171492 A1 | 6/2021 | Zhao et al. | |
| 2022/0071986 A1 | 3/2022 | Burke et al. | |
| 2022/0143007 A1 | 5/2022 | Burke et al. | |
| 2022/0380337 A1 | 12/2022 | Zhao et al. | |
| 2022/0387420 A1 | 12/2022 | Madan et al. | |
| 2024/0376067 A1 | 11/2024 | Reddy et al. | |
| 2024/0398782 A1 | 12/2024 | Burke et al. | |

FOREIGN PATENT DOCUMENTS

| | | | | |
|---|---|---|---|---|
| CN | 102171202 A | 8/2011 | | |
| CN | 103917525 A | 7/2014 | | |
| CN | 105593221 A | 5/2016 | | |
| CN | 108473489 A | 8/2018 | | |
| CN | 110913840 A | 3/2020 | | |
| EP | 2871179 A1 | 5/2015 | | |
| EP | 3053916 A1 | 8/2016 | | |
| EP | 3053916 B1 | 1/2019 | | |
| JP | 2009520690 A | 5/2009 | | |
| KR | 20160062023 A | 6/2016 | | |
| WO | WO-03045920 A1 | 6/2003 | | |
| WO | WO-03066055 A1 | 8/2003 | | |
| WO | WO-2006070284 A1 | 7/2006 | | |
| WO | WO-2007067495 A2 | 6/2007 | | |
| WO | WO-2007098214 A1 | 8/2007 | | |
| WO | WO-2007103554 A1 | 9/2007 | | |
| WO | WO-2008051272 A2 | 5/2008 | | |
| WO | WO-2010019239 A2 | 2/2010 | | |
| WO | WO-2010026121 A1 | 3/2010 | | |
| WO | WO-2010041054 A1 | 4/2010 | | |
| WO | WO-2011019413 A1 | 2/2011 | | |
| WO | WO-2012027731 A2 | 3/2012 | | |
| WO | WO-2012151567 A1 | 11/2012 | | |
| WO | WO-2012162254 A1 | 11/2012 | | |
| WO | WO-2012163354 A1 | 12/2012 | | |
| WO | WO-2013020993 A1 | 2/2013 | | |
| WO | WO-2013050996 A2 | 4/2013 | | |
| WO | WO-2014042945 A1 | 3/2014 | | |
| WO | WO-2015024010 A2 | 2/2015 | | |
| WO | WO-2015046482 A1 | 4/2015 | | |
| WO | WO-2015146929 A1 | 10/2015 | | |
| WO | WO-2016049568 A1 | 3/2016 | | |
| WO | WO-2017003724 A1 | 1/2017 | | |
| WO | WO-2017075340 A1 | 5/2017 | | |
| WO | WO-2017083431 A2 | 5/2017 | | |
| WO | WO-2017106607 A1 | 6/2017 | | |
| WO | WO-2018013676 A1 * | 1/2018 | A61K 3/454 | |
| WO | WO-2018208987 A2 | 11/2018 | | |
| WO | WO-2019030302 A1 | 2/2019 | | |
| WO | WO-2019143718 A1 | 7/2019 | | |
| WO | WO-2020061046 A1 | 3/2020 | | |
| WO | WO-2021011641 A1 | 1/2021 | | |
| WO | WO-2022055880 A1 | 3/2022 | | |

OTHER PUBLICATIONS

Antunes et al. New and emerging pharmacological treatment options for acromegaly. Expert Opin Pharmacother. 22(12):1615-1623 (2021).

Betz et al. Suppression of Growth Hormone and Insulin-Like Growth Factor 1 in Rats After Oral Administration of CRN00808, a Small Molecule, sst2 Selective Somatostatin Biased Agonist. Poster SUN-604 #6743 (2018).

Carmichael et al. Acromegaly clinical trial methodology impact on reported biochemical efficacy rates of somatostatin receptor ligand treatments: A Meta-Analysis. J Clin Endocrinol Metab 99:1825-1833 (2014).

Carroll et al. Acromegaly. In: Feingold KR, Anawalt B, Boyce A, et al., editors. Endotext [Internet]. South Dartmouth (MA): MDText.com, Inc.; 2000-. Available from: https://www.ncbi.nlm.nih.gov/books/NBK279097/ [Updated Sep. 7, 2022].

Crinetics Pharmaceuticals. Acromegaly KOL Event. Presentation. Nov. 20, 2020.

Diabetes-Test information on the website of the CDC (2023).

Gadelha et al. ACROBAT Edge Phase 2 Study: Safety and Efficacy of Switching Injected Long-Acting Somatostatin Receptor Ligands (SRLs) to Once Daily Oral Paltusotine. Poster #7452 (2021).

Gadelha et al. Safety and efficacy of switching injected peptide long-acting somatostatin receptor ligands to once daily oral paltusotine: ACROBAT edge phase 2 study. Journal of the Endocrine Society 5.Supplement_1 (2021):A526-A527 (2021).

Gadelha et al. The Future of Somatostatin Receptor Ligands in Acromegaly. J Clin Endocrinol Metab. 107(2):297-308 (2022).

Henry et al., Hyperglycemia associated with pasireotide: results from a mechanistic study in healthy volunteers. J Clin. Endocrinol. Metab. 98(8):3446-3453 (2013).

Hirayama Yoshinaki. The Organic Compound Crystal Production Handbook. (pp. 17, 23, 37, 40, 45, 51, 57, 65) (2008).

Katznelson et al. Acromegaly: an endocrine society clinical practice guideline. J Clin Endocrinol Metab 99(11):3933-3951 (2014).

Kuhn et al. Pharmacokinetic study and effects on growth hormone secretion in healthy volunteers of the new somatostatin analogue BIM 23014. Eur J Clin Pharmacol 45:73-77 (1993).

Madan et al. Paltusotine, a novel oral once-daily nonpeptide SST2 receptor agonist, suppresses GH and IGF-1 in healthy volunteers. Pituitary 25(2):328-339 (2022).

Mazziotti et al. Effects of high-dose octreotide LAR on glucose metabolism in patients with acromegaly inadequately controlled by conventional somatostatin analog therapy. Eu J Endocrinol 164:341-347 (2011).

Mazziotti et al., Effects of somatostatin analogs on glucose homeostasis: a metaanalysis of acromegaly studies. J Clin. Endocrinol. Metab. 94(5):1500-1508 (2009).

NCT03792555 ClinicalTrials.gov (Jan. 3, 2019).

Paltusotine (CRN00808), Evidence from the website of the MedChemExpress (2023).

Parkinson et al., A comparison of the effects of pegvisomant and octreotide on glucose, insulin, gastrin, cholecystokinin, and pancreatic polypeptide responses to oral glucose and a standard mixed meal. J. Clin. Endocrinol. Metab. 87:1797-1804 (2002).

PCT/US2022/030721 International Search Report and Written Opinion dated Oct. 17, 2022.

(56) References Cited

OTHER PUBLICATIONS

PCT/US2022/030721 Invitation to Pay Additional Fees dated Jul. 26, 2022.
Pharmaceutical Affairs and Pharmaceutical Safety Bureau Examination and Management Department Chief Administrative Agency (pp. 1-11) (1998).
Pubchem-SID: 374408995 Deposit Date: Jun. 23, 2018 (Jun. 23, 2018).
Quabbe et al., Dose-response study and long term effect of the somatostatin analog octreotide in patients with therapy-resistant acromegaly. J. Clin. Endocrinol. Metab. 68:873-881 (1989).
Randeva et al. ACROBAT Advance: long-term safety and efficacy results of paltusotine for the treatment of acromegaly. Poster p. 80 (2021).
Rico, Elizabeth et al., Selective Somatostatin 5 (SST5) and Somatostatin 2 (SST2) Nonpeptide Agonists Potently Suppress Glucose- and Tolbutamide-Stimulated Dynamic Insulin Secretion From Isolated Human Islets . J Endocrine Soc 5(Supp I):A325 (Apr.-May 2021).
Sandret et al. Place of cabergoline in acromegaly: a meta-analysis. J Clin Endocrinol Metab 96(5):1327-1335 (2011).
Stumvoll et al. Use of the oral glucose tolerance test to assess insulin release and insulin sensitivity. Diabetes Care 23(3):295-301 (2000).
Take on an Empty Stomach. How Do You Know When Your Stomach Is Empty? wral.news (Oct. 1, 2018).
Tiberg et al. Octreotide s.c. depot provides sustained octreotide bioavailability and similar IGF-1 suppression to octreotide LAR in healthy volunteers. Br J Clin Pharmacol 80:460-472 (2015).
Wermuth, C. G. Knitting, Winding under the latest medicinal chemicals. Technomere (pp. 347-365) (1999).
Berge et al. Pharmaceutical Salts. Journal of Pharmaceutical Sciences 66(1): 1-19 (Jan. 1977).
Brazeau et al. Hypothalamic polypeptide that inhibits the secretion of immunoreactive pituitary growth hormone. Science 179:77-79 (1973).
BUNDGAARD. Design and Application of Prodrugs. Textbook of Drug Design and Development. Krosgaard-Larsen and Bundgaard. Chapter 5. pp. 113-191 (1991).
BUNDGAARD. Design of Prodrugs. Elsevier (12 pgs.) (1985).
BUNDGAARD. Means to Enhance Penetration: Prodrugs as a Means to Improve the Delivery of Peptide Drugs. Advanced Drug Delivery Review 8:1-38 (1992).
Cescato et al. Agonist-Biased Signaling at the sst2A Receptor: The Multi-Somatostatin Analogs KE108 and SOM230 Activate and Antagonize Distinct Signaling Pathways. Mol Endocrinol 24(1):240-249 (2010).
Esch et al. Primary structure of ovine hypothalamic somatostatin-28 and somatostatin-25. Pnas USA 77:6827-6831 (1980).
Gadelha et al. Safety and Efficacy of Switching Injected Peptide Long-Acting Somatostatin Receptor Ligands to Once Daily Oral Paltusotine: ACROBAT Edge Phase 2 Study. Poster Presented at ENDO 2021 (Mar. 20-23, 2021).
Gao et al., Identification, characterization and quantification of process-related and degradation impurities in lisdexamfetamine dimesylate: identifiction of two new compounds. Molecules 23(12):3125 (2018).
Garrett et al. The Art of Meeting Palladium Specifications in Active Pharmaceutical Ingredients Produced by Pd-Catalyzed Reactions. Adv. Synth. Catal. 346:889-900 (2004).
Gradiz et al. MIA PaCa-2 and PANC-1—pancreas ductal adenocarcinoma cell lines with neuroendocrine differentiation and somatostatin receptors. Scientific Reports 6:21648 (15 pgs.) (2016).
Guideline on the Specification Limits for Residues of Metal Catalysts. European Medicines Agency. Pre-authorization Evaluation of Medicines for Human Use, London (Jan. 2007) (pp. 1-32).
Ishida et al. Discovery and SAR Studies of Orally Active Somatostatin Receptor Subtype-2 (SSTR2) Agonists for the Treatment of Acromegaly. ACS Chem Neurosci 11(10):1482-1494 (2020).
Luo et al. Pharmacokinetics and Safety of an Improved Oral Formulation of Paltusotine, a Selective, Non-Peptide Somatostatin Receptor 2 (SST2) Agonist for the Treatment of Acromegaly. Poster Presented at ENDO 2021 (Mar. 20-23, 2021).
Madan et al. Absolute Oral Bioavailability and Absorption, Metabolism, Excretion of [14C]-Labeled Paltusotine (CRN00808), An Orally Bioavailable, Nonpeptide, Selective, Somatostatin Receptor 2 (SST2) Biased Agonist for The Treatment of Acromegaly. Poster Presented at the virtual European Congress of Endocrinology (eECE) on Sep. 5-9, 2020.
Madan et al. Final Results from the First in Man Phase 1 Clinical Trial of CRN00808, an Orally Bioavailable sst2-Selective, Nonpeptide Somatostatin Biased Agonist, for the Treatment of Acromegaly: Safety, Pharmacokinetics, Pharmacodynamics, and Midazolam Drug Interaction in Healthy Volunteers. Poster Presented at ENDO 2019 (Mar. 23-26, 2019).
Madan et al. OR23-05 Human Absorption, Metabolism, Excretion, and Absolute Oral Bioavailability of 14C-CRN00808, an Orally Bioavailable, Nonpeptide, Selective, Somatostatin Receptor 2 (sST2) Biased Agonist for the Treatment of Acromegaly. J Endocr Soc. 4(Suppl 1):A352-A353. Published online May 8, 2020.
Maia et al. Novel therapies for acromegaly. Endocrine Connections 9(12):R274-R285 (2020).
Patel et al. Somatostatin receptors. Trends Endocrinol Metab 8:398-405 (1997).
PCT/US2017/041694 International Search Report and Written Opinion dated Dec. 12, 2017.
PCT/US2019/013844 International Search Report and Written Opinion dated May 1, 2019.
PCT/US2020/042119 International Search Report and Written Opinion dated Nov. 5, 2020.
PCT/US2021/049282 International Search Report and Written Opinion dated Dec. 22, 2021.
Pradayrol et al. N-terminally extended somatostatin: the primary structure of somatostatin-28. FEBS Letters 109:55-58 (1980).
Prasoon et al. Role of somatostatin and somatostatin receptor type 2 in postincisional nociception in rats. Neropeptides 49:47-54 (2015).
Reisine et al. Molecular biology of somatostatin receptors. Endocr Rev 16:427-442 (1995).
Science IP CAS Search, May 23, 2016 (291 pgs).
Song et al. Amine-Mediated Transimination and Aromatization-Triggered Domino Reaction in the Synthesis of Polyfunctionalized 4-Aminoquinolines. Org Lett 18(20):5328-5331 (2016).
Stahl et al. Handbook of Pharmaceutical Salts. Verlag Helvetica Chimica Acta, Zurich, 2002.
Widder et al. Section III: Prodrugs Kinetics. Method in Enzymology. 112:309-396 (1985).
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).
Young et al. SUN-125 Phase lb Study of Dual Therapy with an Aromatase Inhibitor Exemestane and Carboplatin-Based Therapy for Postmenopausal Women with Advanced Non-Small Cell Lung Cancer, Journal of the Endocrine Society. Tumor Biology: Diagnostics, Therapies, Endocrine Neoplasias, And Hormone Dependent Tumors. Available at https://doi.org/10.1210/jendso/bvaa046.695 Journal of the Endocrine Society 4(Supp 1):A352 (Abstract).
Zhao et al. Discovery of nonpeptide 3,4-dihydroquinazoline-4-carboxamides as potent and selective sst2 agonists. Bioorg Med Chem Lett 30(17):127391 (2020).
Bastin, et al. Salt Selection and Optimisation Procedures for Pharmaceutical New Chemical Entities. Org. Proc. Res. Dev. 4(5):427-435 (2000).
Chiang et al. In vitro and in vivo evaluation of amorphous solid dispersions generated by different bench-scale processes, using griseofulvin as a model compound. AAPS J 15(20:608-617 (2013).
Florence. Polymorph screening in pharmaceutical development. European Pharmaceutical Review. Available at https://www.europeanpharmaceuticalreview.com/article/3659/ polymorph-screening-in-pharmaceutical-development/ [retrieved on Mar. 7, 2018] (2010).
Paudel et al. Manufacturing of solid dispersions of poorly water soluble drugs by spray drying: Formulation and process considerations. International Journal of Pharmaceutics. 453(1):253-284 (2013).

(56) References Cited

OTHER PUBLICATIONS

Caplin, ME et al. Lanreotide in metastatic enteropancreatic neuroendocrine tumors. The New England Journal of Medicine 371(16):1556-1557 (2014).
Chan, David L. et al. Developments in the treatment of carcinoid syndrome—impact of telotristat. Ther Clin Risk Manag 14:323-329 (2018).
Chan, JA et al. Medical Management of Pancreatic Neuroendocrine Tumors: Current and Future Therapy. Surg Oncol Clin N Am 25(2):423-437 (2016).
Co-pending U.S. Appl. No. 18/587,187, inventors Reddy; Jayachandra P. et al., filed Feb. 26, 2024.
Crinetics Therapeutics 2021 Clinical Strategy and 2020 Financial Results Mar. 30, 2021. Crinetics Pharmaceuticals, Inc. (pp. 1-12) (2021).
Crinetics Therapeutics Corporate Presentation Jan. 2021. Crinetics Pharmaceuticals, Inc. (1-38) (2021).
Crinetics Therapeutics Corporate Presentation Mar. 2021. Crinetics Pharmaceuticals, Inc. (pp. 1-43) (2021).
Crinetics Therapeutics Corporate Presentation Sep. 2020. Crinetics Pharmaceuticals, Inc. (pp. 1-34) (2020).
Halperin, DM et al. Frequency of carcinoid syndrome at neuroendocrine tumour diagnosis: a population-based study. Lancet Oncol 18(4):525-534 (2017).
Kunz PL. Carcinoid and neuroendocrine tumors: building on success. J Clin Oncol. 33(16):1855-1863 (2015).
Kvols, LK et al. Treatment of the malignant carcinoid syndrome. Evaluation of a long-acting somatostatin analogue. N Engl J Med 315(11):663-666 (1986).
Lagast, Hjalmar et al. Dose selection for paltusotine, a once daily oral nonpeptide, somatostatin receptor 2 ligand, for the treatment of patients with carcinoid syndrome (CS). Poster presented at North American Neuroendocrine Tumor Society NET Medical Symposium Nov. 4-6, 2021 (1 pg.).
Naraev, Boris G. et al. Management of Diarrhea in Patients With Carcinoid Syndrome. Pancreas 48(8):961-972 (2019).
Oronsky, B. et al. Nothing But NET: A Review of Neuroendocrine Tumors and Carcinomas. Neoplasia 19(12):991-1002 (2017).
Rinke, A et al. Placebo-controlled, double-blind, prospective, randomized study on the effect of octreotide LAR in the control of tumor growth in patients with metastatic neuroendocrine midgut tumors: a report from the PROMID Study Group. J Clin Oncol 27(28):4656-4663 (2009).
Anderson et al. Hiroshi Nagase Supervision of Translation, Newest Medicinal Chemistry Beaming, Technomics, Inc., (pp. 347-365) (Sep. 25, 1999).
Liu, Yihuan et al. Study on the Dissolution Model of Efavirenz in Solid Dispersion Based on HPMCAS Carrier. Chinese Journal of Modern Applied Pharmacy 9:1096-1101 (2020) (English Abstract).

* cited by examiner

CRYSTALLINE FORMS OF SOMATOSTATIN MODULATORS

CROSS-REFERENCE TO RELATED APPLICATIONS

This application claims benefit of U.S. Provisional Patent Application No. 62/875,285, filed on Jul. 17, 2019, which is incorporated herein by reference in its entirety.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor, or combination thereof, is attractive for the treatment of conditions, diseases, or disorders that would benefit from modulating somatostatin activity.

SUMMARY OF THE INVENTION

Disclosed herein is a compound that is 3-(4-(4-aminopiperidin-1-yl)-3-(3,5-difluorophenyl)quinolin-6-yl)-2-hydroxybenzonitrile dimesylate.

In one aspect disclosed herein, the compound is the amorphous solid form of 3-(4-(4-aminopiperidin-1-yl)-3-(3,5-difluorophenyl)quinolin-6-yl)-2-hydroxybenzonitrile dimesylate. In some embodiments, the amorphous solid form of 3-(4-(4-aminopiperidin-1-yl)-3-(3,5-difluorophenyl)quinolin-6-yl)-2-hydroxybenzonitrile dimesylate is characterized as having: an X-ray powder diffraction (XRPD) pattern showing a lack of crystallinity; a modulated Differential Scanning Calorimetry thermogram substantially the same as shown in FIG. 1; a modulated Differential Scanning Calorimetry thermogram with a glass transition temperature having an onset at about 166.6° C. and a midpoint at about 169.3° C.; a Thermogravimetric Analysis pattern substantially the same as shown in FIG. 12; a Thermogravimetric Analysis pattern with a 3.85% w/w loss between 40 and 170° C.; or a combination thereof.

In another aspect disclosed herein, the compound is a crystalline form of 3-(4-(4-aminopiperidin-1-yl)-3-(3,5-difluorophenyl)quinolin-6-yl)-2-hydroxybenzonitrile dimesylate.

In some embodiments disclosed herein, the compound is the crystalline Pattern A of 3-(4-(4-aminopiperidin-1-yl)-3-(3,5-difluorophenyl)quinolin-6-yl)-2-hydroxybenzonitrile dimesylate. In some embodiments, the crystalline Pattern A of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 3; an X-ray powder diffraction pattern with X-ray diffraction pattern reflections at about 6.20° 2-Theta, about 6.76° 2-Theta, about 17.14° 2-Theta, and about 21.70° 2-Theta; a Differential Scanning Calorimetry thermogram substantially the same as shown in FIG. 4; a Differential Scanning Calorimetry thermogram with four endothermic events having: an onset at about 78.4° C. and a peak at about 81.8° C.; an onset at about 266.1° C. and a peak at about 270.1° C.; an onset at about 281.1° C. and a peak at about 286.1° C.; and an onset at about 294.6° C. and a peak at about 297.7° C.; a Thermogravimetric Analysis pattern substantially the same as shown in FIG. 5*a*; a Thermogravimetric Analysis pattern with a 2.28% w/w loss from 60 to 180° C.; a Dynamic Vapour Sorption isotherm plot substantially the same as shown in FIG. 6; a reversible water uptake (9.8% w/w) between 2% and 95% Relative Humidity (RH); an XRPD that converts to Pattern B on storage at 75% RH and 40° C. for 7 days; an XRPD that converts to Pattern B on storage at 96% RH and 25° C. for 3 days; an unchanged XRPD after drying under dynamic vacuum at 50° C. for 2 hours; an XRPD that converts to Pattern P after heating to 255° C.; a 1.5% w/w water content; or a combination thereof.

In some embodiments disclosed herein, the compound is the crystalline hydrate Pattern B of 3-(4-(4-aminopiperidin-1-yl)-3-(3,5-difluorophenyl)quinolin-6-yl)-2-hydroxybenzonitrile dimesylate. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 7; an X-ray powder diffraction pattern with X-ray diffraction pattern reflections at about 5.58° 2-Theta, about 7.48° 2-Theta, about 15.94° 2-Theta, and about 25.13° 2-Theta; a Differential Scanning Calorimetry thermogram substantially the same as shown in: FIG. 8; or FIG. 10*b*; a Differential Scanning Calorimetry thermogram with: a broad endothermic event having an onset at about 86.3° C. and a peak at about 115.1° C.; and an endothermic event having an onset at about 213.2° C. and a peak at about 221.8° C.; or an endothermic event having an onset at about 205.6° C. and a peak at about 221.8° C.; an exothermic event having an onset at about 243.0° C. and a peak at about 254.2° C.; and an endothermic event having an onset at about 278.0° C. and a peak at about 288.2° C.; a Thermogravimetric Analysis pattern substantially the same as shown in: FIG. 9*a*; or FIG. 10*a*; a Thermogravimetric Analysis pattern with: a 2.9% w/w loss from 40 to 205° C.; or a 4.23% w/w loss from 45 to 175° C.; a Dynamic Vapour Sorption isotherm plot substantially the same as shown in FIG. 11; a reversible water uptake (3.2% w/w) between 2% and 95% Relative Humidity (RH); an unchanged XRPD after DVS analysis at 95% RH and 25° C.; an unchanged XRPD after storage at 75% RH and 40° C. for 7 days; an unchanged XRPD after drying under dynamic vacuum at 50° C. for 2 hours; an unchanged XRPD after storage under static vacuum at 50° C. for 3 days; an XRPD that converts to Pattern I after heating to 270° C.; a 4.2% w/w water content; or a combination thereof.

In some embodiments disclosed herein, the compound is the crystalline Pattern C of 3-(4-(4-aminopiperidin-1-yl)-3-(3,5-difluorophenyl)quinolin-6-yl)-2-hydroxybenzonitrile dimesylate. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 12; an X-ray powder diffraction pattern with X-ray diffraction pattern reflections at about 7.10° 2-Theta, about 17.44° 2-Theta, about 22.18° 2-Theta, and about 25.20° 2-Theta; a Differential Scanning Calorimetry thermogram substantially the same as shown in FIG. 13; a Differential Scanning Calorimetry thermogram with an exothermic event having an onset at about 192.8° C. and a peak at about 213.3° C.; an endothermic event having an onset at about 252.2° C. and a peak at about 272.3° C.; and an endothermic event having an onset at about 296.6° C. and a peak at about 298.9° C.; a Thermogravimetric Analysis pattern substantially the same as shown in FIG. 14*a*; a Thermogravimetric Analysis pattern with a 0.12% w/w loss from 40 to 140° C. and a further 0.62% w/w loss from 140 to 290° C.; an unchanged XRPD after storage at 75% RH and 40° C. for 7 days; an unchanged XRPD after drying under dynamic vacuum at 50° C. for 2 hours; an XRPD that converts to Pattern I after heating to 240° C.; or a combination thereof.

In some embodiments disclosed herein, the compound is the crystalline Pattern I of 3-(4-(4-aminopiperidin-1-yl)-3-(3,5-difluorophenyl)quinolin-6-yl)-2-hydroxybenzonitrile dimesylate. In some embodiments, the crystalline Pattern I of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 15; an X-ray powder diffraction pattern with X-ray diffraction pattern reflections at about 6.74° 2-Theta, about 11.17° 2-Theta, about 20.83° 2-Theta, and about 21.65° 2-Theta; a Differential Scanning Calorimetry thermogram substantially the same as shown in FIG. 16; a Differential Scanning Calorimetry thermogram with an endothermic event having an onset at about 260.9° C. and a peak at about 274.8° C.; and an endothermic event having an onset at about 292.7° C. and a peak at about 296.0° C.; a Thermogravimetric Analysis pattern substantially the same as shown in FIG. 17*a*; a Thermogravimetric Analysis pattern with a 0.19% w/w loss from 40 to 185° C. and a further 0.67% w/w loss from 185 to 290° C.; a Dynamic Vapour Sorption isotherm plot substantially the same as shown in FIG. 18; a reversible water uptake (9.1% w/w) between 2% and 95% Relative Humidity (RH); with a 2.5% w/w water uptake between 15 and 75% RH; an XRPD that converts to Pattern B after DVS analysis between 2% and 95% RH and 25° C.; an unchanged XRPD after storage at 75% RH and 40° C. for 7 days; an unchanged XRPD after drying under dynamic vacuum at 50° C. for 2 hours; a 0.29% w/w water content; or a combination thereof.

In some embodiments disclosed herein, the compound is the crystalline isopropanol solvate Pattern D of 3-(4-(4-aminopiperidin-1-yl)-3-(3,5-difluorophenyl)quinolin-6-yl)-2-hydroxybenzonitrile dimesylate. In some embodiments, the crystalline isopropyl solvate Pattern D of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 19; an X-ray powder diffraction pattern with X-ray diffraction pattern reflections at about 6.10° 2-Theta, about 6.70° 2-Theta, about 17.75° 2-Theta, and about 22.22° 2-Theta; an XRPD that converts to Pattern A after drying under dynamic vacuum at 50° C. for 2 hours; or a combination thereof.

In some embodiments disclosed herein, the compound is the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate. In some embodiments, the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 20; an X-ray powder diffraction pattern with X-ray diffraction pattern reflections at about 6.42° 2-Theta, about 19.99° 2-Theta, and about 21.12° 2-Theta; an XRPD that converts to Pattern A after drying under dynamic vacuum at 50° C. for 2 hours; or a combination thereof.

In some embodiments disclosed herein, the compound is the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate. In some embodiments, the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 21; an X-ray powder diffraction pattern with X-ray diffraction pattern reflections at about 5.63° 2-Theta, about 6.27° 2-Theta, about 20.55° 2-Theta, and about 22.33° 2-Theta; an XRPD that converts to Pattern I after drying under dynamic vacuum at 50° C. for 2 hours; or a combination thereof.

In some embodiments disclosed herein, the compound is the crystalline ethyl acetate solvate Pattern G of 3-(4-(4-aminopiperidin-1-yl)-3-(3,5-difluorophenyl)quinolin-6-yl)-2-hydroxybenzonitrile dimesylate. In some embodiments, the crystalline ethyl acetate solvate Pattern G of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 22; an X-ray powder diffraction pattern with X-ray diffraction pattern reflections at about 6.62° 2-Theta, about 13.21° 2-Theta, about 19.79° 2-Theta, and about 21.72° 2-Theta; an XRPD that converts to Pattern I after drying under dynamic vacuum at 50° C. for 2 hours; or a combination thereof.

In some embodiments disclosed herein, the compound is the crystalline isopropyl acetate solvate Pattern H of 3-(4-(4-aminopiperidin-1-yl)-3-(3,5-difluorophenyl)quinolin-6-yl)-2-hydroxybenzonitrile dimesylate. In some embodiments, the crystalline isopropyl acetate solvate Pattern H of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 23; an X-ray powder diffraction pattern with X-ray diffraction pattern reflections at about 5.66° 2-Theta, about 16.77° 2-Theta, and about 22.78° 2-Theta; an XRPD that converts to Pattern I after drying under dynamic vacuum at 50° C. for 2 hours; or a combination thereof.

In some embodiments disclosed herein, the compound is the crystalline Pattern J of 3-(4-(4-aminopiperidin-1-yl)-3-(3,5-difluorophenyl)quinolin-6-yl)-2-hydroxybenzonitrile dimesylate. In some embodiments, the crystalline Pattern J of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 24; an X-ray powder diffraction pattern with X-ray diffraction pattern reflections at about 6.32° 2-Theta, about 6.72° 2-Theta, about 12.33° 2-Theta, and about 21.47° 2-Theta; or a combination thereof.

In some embodiments disclosed herein, the compound is the crystalline Pattern K of 3-(4-(4-aminopiperidin-1-yl)-3-(3,5-difluorophenyl)quinolin-6-yl)-2-hydroxybenzonitrile dimesylate. In some embodiments, the crystalline Pattern K of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 25; an X-ray powder diffraction pattern with X-ray diffraction pattern reflections at about 5.42° 2-Theta, about 15.90° 2-Theta, about 19.59° 2-Theta, and about 21.52° 2-Theta; a Differential Scanning Calorimetry thermogram substantially the same as shown in FIG. 26*b*; a Differential Scanning Calorimetry thermogram with an endothermic event having an onset at about 254.1° C. and a peak at about 271.9° C.; and an endothermic event having an onset at about 294.5° C. and a peak at about 297.7° C.; a Thermogravimetric Analysis pattern substantially the same as shown in FIG. 26*a*; a Thermogravimetric Analysis pattern with a 0.1% w/w loss from 40 to 190° C. and a further 0.69% w/w loss from 190 to 310° C.; an unchanged XRPD after drying under dynamic vacuum at 50° C. for 2 hours; or a combination thereof.

In some embodiments disclosed herein, the compound is the crystalline acetone solvate Pattern M of 3-(4-(4-aminopiperidin-1-yl)-3-(3,5-difluorophenyl)quinolin-6-yl)-2-hydroxybenzonitrile dimesylate. In some embodiments, the crystalline acetone solvate Pattern M of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 27; an X-ray powder diffraction pattern with X-ray diffraction pattern reflections at about 5.67° 2-Theta, about 14.63° 2-Theta, about 22.14° 2-Theta, and about 24.91° 2-Theta; or a combination thereof.

In some embodiments disclosed herein, the compound is the crystalline acetonitrile solvate Pattern N of 3-(4-(4-aminopiperidin-1-yl)-3-(3,5-difluorophenyl)quinolin-6-yl)-2-hydroxybenzonitrile dimesylate. In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 28; an X-ray powder diffraction pattern with X-ray diffraction pattern reflections at about 5.18° 2-Theta, and about 17.21° 2-Theta; a Differential Scanning Calorimetry thermogram substantially the same as shown in FIG. 29*b*; a Differential Scanning Calorimetry thermogram with an endothermic event having an onset at about 132.6° C. and a peak at about 144.0° C.; an endothermic event having an onset at about 179.7° C. and a peak at about 193.5° C.; and an endothermic event having an onset at about 192.4° C. and a peak at about 211.1° C.; a Thermogravimetric Analysis pattern substantially the same as shown in FIG. 29*a*; a Thermogravimetric Analysis pattern with a 5.44% w/w loss from 40 to 220° C.; an unchanged XRPD after drying under dynamic vacuum at 50° C. for 2 hours; or a combination thereof.

In some embodiments disclosed herein, the compound is the crystalline hydrate Pattern O of 3-(4-(4-aminopiperidin-1-yl)-3-(3,5-difluorophenyl)quinolin-6-yl)-2-hydroxybenzonitrile dimesylate. In some embodiments, the crystalline hydrate Pattern O of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 30; an X-ray powder diffraction pattern with X-ray diffraction pattern reflections at about 5.56° 2-Theta, 15.87° 2-Theta, 18.43° 2-Theta, and about 24.80° 2-Theta; a Differential Scanning Calorimetry thermogram substantially the same as shown in FIG. 31*b*; a Differential Scanning Calorimetry thermogram with an endothermic event having an onset at about 206.9° C. and a peak at about 217.6° C.; a Thermogravimetric Analysis pattern substantially the same as shown in FIG. 31*a*; a Thermogravimetric Analysis pattern with a 4.54% w/w loss from 40 to 260° C.; an unchanged XRPD after drying under dynamic vacuum at 50° C. for 2 hours; or a combination thereof.

In some embodiments disclosed herein, the compound is the crystalline Pattern P of 3-(4-(4-aminopiperidin-1-yl)-3-(3,5-difluorophenyl)quinolin-6-yl)-2-hydroxybenzonitrile dimesylate. In some embodiments, the crystalline Pattern P of 3-(4-(4-aminopiperidin-1-yl)-3-(3,5-difluorophenyl)quinolin-6-yl)-2-hydroxybenzonitrile dimesylate is characterized as having: an X-ray powder diffraction pattern substantially the same as shown in FIG. 32; an X-ray powder diffraction pattern with X-ray diffraction pattern reflections at about 6.97° 2-Theta, about 17.26° 2-Theta, about 19.33° 2-Theta, and about 20.94° 2-Theta; an unchanged XRPD after drying under dynamic vacuum at 50° C. for 2 hours; an XRPD that converts to Pattern B on storage at 96% RH and 25° C. for 3 days; or a combination thereof.

In another aspect disclosed herein, is a pharmaceutical composition comprising 3-(4-(4-aminopiperidin-1-yl)-3-(3,5-difluorophenyl)quinolin-6-yl)-2-hydroxybenzonitrile dimesylate, or a solvate thereof, and at least one pharmaceutically acceptable excipient. In some embodiments, the pharmaceutical composition comprises amorphous 3-(4-(4-aminopiperidin-1-yl)-3-(3,5-difluorophenyl)quinolin-6-yl)-2-hydroxybenzonitrile dimesylate, or a solvate thereof, and at least one pharmaceutically acceptable excipient. In some embodiments, the pharmaceutical composition comprises crystalline 3-[4-(4-amino-piperidin-1-yl)-3-(3,5-difluoro-phenyl)-quinolin-6-yl]-2-hydroxy-benzonitrile dimesylate, or solvate thereof, and at least one pharmaceutically acceptable excipient. In some embodiments, the pharmaceutical composition is formulated for administration to a mammal by oral administration. In some embodiments, the pharmaceutical composition is in the form of a solid form pharmaceutical composition. In some embodiments, the pharmaceutical composition is in the form of a tablet, a pill, or a capsule. In some embodiments, the pharmaceutical composition is a composition for use for the treatment of a disease or condition in a mammal that would benefit from the modulation of the somatostatin receptor subtype 2 (SSTR2) activity. In some embodiments, the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

In another aspect disclosed herein, is a method of treating a disease or condition in a mammal that would benefit from the modulation of the somatostatin receptor subtype 2 (SSTR2) activity comprising administering 3-(4-(4-aminopiperidin-1-yl)-3-(3,5-difluorophenyl)quinolin-6-yl)-2-hydroxybenzonitrile dimesylate, or a solvate thereof, to the mammal in need thereof. In some embodiments, the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

In another aspect disclosed herein, is a method of treating a disease or condition in a mammal that would benefit from the modulation of the somatostatin receptor subtype 2 (SSTR2) activity comprising administering a pharmaceutical composition comprising 3-(4-(4-aminopiperidin-1-yl)-3-(3,5-difluorophenyl)quinolin-6-yl)-2-hydroxybenzonitrile dimesylate, or a solvate thereof, and at least one pharmaceutically acceptable excipient, to the mammal in need thereof. In some embodiments, the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

In some embodiments, the mammal is a human.

Articles of manufacture, which include packaging material, the somatostatin receptor modulator 3-(4-(4-aminopiperidin-1-yl)-3-(3,5-difluorophenyl)quinolin-6-yl)-2-hydroxybenzonitrile dimesylate, or a solvate thereof, within the packaging material, and a label that indicates that the somatostatin receptor modulator is used for modulating the activity of somatostatin receptor(s), or for the treatment, prevention or amelioration of one or more symptoms of a disease of condition described herein are provided.

DETAILED DESCRIPTION OF THE INVENTION

Figure 1:
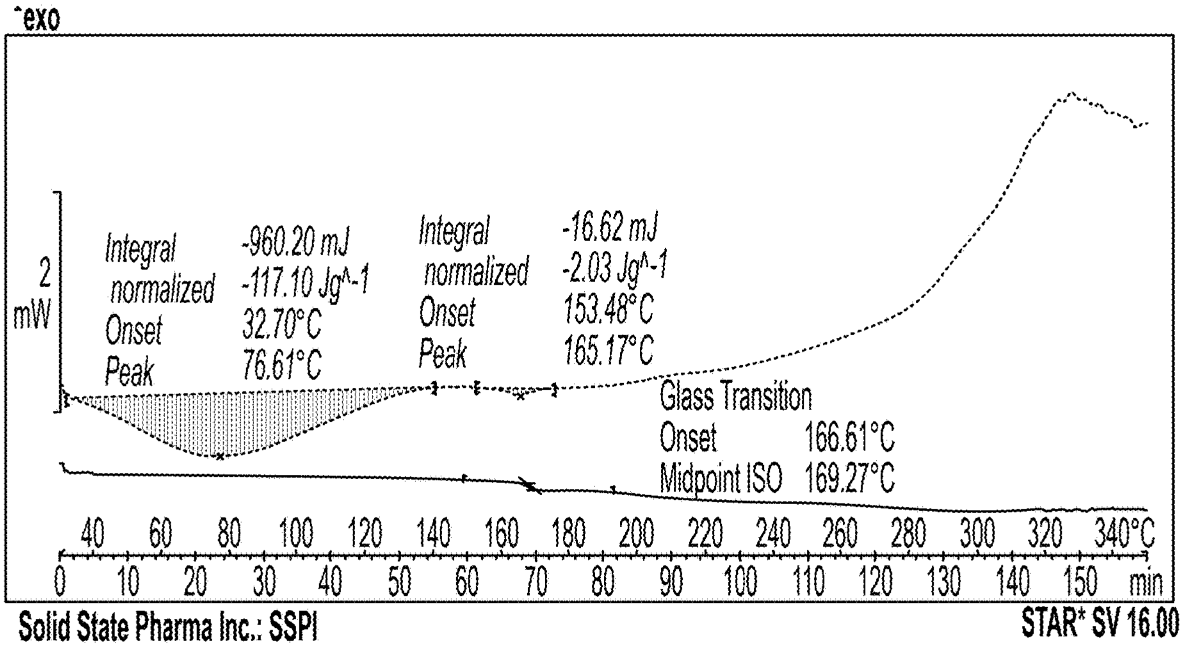
FIG. 1 shows the modulated reversible and non-reversible heat flow DSC thermograms of amorphous Compound A•2MSA.

Somatostatin (SST), also known as somatotropin release inhibiting factor (SRIF) was initially isolated as a 14-amino acid peptide from ovine hypothalamii (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters,* 109, 55-58, 1980; Esch et al., *Proc. Natl. Acad. Sci. USA,* 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous system (CNS) and gut, and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, and SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-

405, 1997). All the receptors are members of the class-A subgroup of the GPCR superfamily. SST2A receptor is the most widely expressed subtype in human tumors and is the dominant receptor by which GH secretion is suppressed. Unless otherwise stated, the term SSTR2 means SSTR2a.

It is possible to selectively modulate any one of the somatostatin receptor subtypes, or combination thereof. In some embodiments, selectively modulating any one of the somatostatin receptor subtypes relative to the other somatostatin receptor subtypes, or combination thereof, is useful in a variety of clinical applications. In some embodiments, selectively modulating any one of the somatostatin receptor subtypes relative to the other somatostatin receptor subtypes reduces unwanted side effects in a variety of clinical applications.

For example, modulation of SSTR2 activity mediates the inhibition of growth hormone (GH) release from the anterior pituitary and glucagon release from pancreas. SSTR2 is also implicated in many other biological functions such as, but not limited to, cell proliferation, nociception, inflammation, and angiogenesis. In some embodiments, a selective SSTR2 modulator is used in the treatment of acromegaly, gut neuroendocrine tumors, pain, neuropathies, nephropathies, and inflammation, as well as retinopathies resulting from aberrant blood vessel growth. In some other embodiments, a selective SSTR2 modulator is used in the treatment of arthritis, pain, cancer, inflammatory bowel disease, irritable bowel syndrome, Crohn's disease, Cushing's disease, acute lung injury, acute respiratory distress syndrome, and ophthalmic disorders such as age-related macular degeneration (AMD), diabetic retinopathy, diabetic macular edema, and Graves ophthalmology, among others.

In some embodiments, SSTR4 agonists exhibit anti-inflammatory and anti-nociceptive effects.

In some embodiments, SSTR3 agonists inhibit insulin secretion.

In some embodiments, SSTR5 agonists inhibit insulin secretion. In addition, SSTR5 has also been implicated to modulate the release of growth hormone.

Somatostatin peptide and its receptor subtypes are also widely expressed in the brain and disruption or diminishment of their activity is potentially involved in several psychiatric and neurodegenerative diseases. For example, concentrations of somatostatin in the cerebral cortex and hippocampus are reduced in schizophrenics and one of the most consistent neuropathologic findings in this patient group is a deficit in cortical inhibitory interneurons expressing somatostatin. Somatostatin is also highly expressed in brain regions associated with seizures and has also been implicated as having an important role in epilepsy. Somatostatin levels are diminished in the hippocampi of Alzheimer's and Parkinson's patients, suggesting that restoration of its signaling as a potential drug target for neurodegeneration.

In one aspect, compounds described herein are modulators of SSTR2. In some embodiments, compounds described herein selectively modulate the activity of SSTR2 relative to the other somatostatin receptors.

In some embodiments, compounds described here are amenable to oral administration to a mammal in need of treatment with a somatostatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to acromegaly, neuroendocrine tumors, retinopathies and other ophthalmic disorders, neuropathy, nephropathy, respiratory diseases, cancers, pain, neurodegenerative diseases, inflammatory diseases, as well as psychiatric and neurodegenerative disorders. In some embodiments, somatostatin receptor modulators described herein are used in the treatment of acromegaly in a mammal.

In some embodiments, somatostatin receptor modulators described herein inhibit the secretion of various hormones and trophic factors in mammals. In some embodiments, the compounds are used to suppress certain endocrine secretions, such as, but not limited to GH, insulin, glucagon and prolactin. The suppression of certain endocrine secretions is useful in the treatment of disorders such as acromegaly; endocrine tumors such as carcinoids, VIPomas, insulinomas and glucagonomas; or diabetes and diabetes-related pathologies, including retinopathy, neuropathy and nephropathy. In some embodiments, somatostatin receptor modulators described herein are used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, colon and pancreatic adenocarcinomas (ductal type), chondrosarcomas, and melanomas, diabetic retinopathy, and atherosclerosis associated with vascular grafts and restenosis following angioplasty.

In some embodiments, somatostatin receptor modulators described herein are used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, somatostatin receptor modulators described herein provide cytoprotection in disorders involving the splanchnic blood flow, including cirrhosis and oesophagal varices.

Compound A

Compound A is a somatostatin modulator that is useful in the methods of treatment described herein.

As used herein, the term Compound A refers to 3-(4-(4-aminopiperidin-1-yl)-3-(3,5-difluorophenyl)quinolin-6-yl)-2-hydroxybenzonitrile, which has the chemical structure shown below.

Compound A

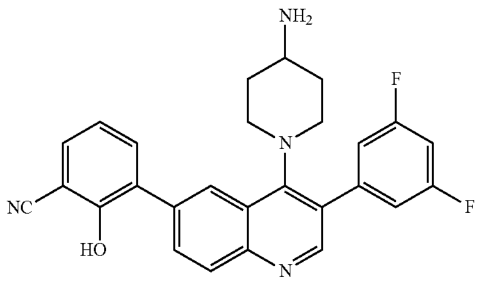

Described herein is a mesylate salt of Compound A. Unless indicated otherwise, "mesylate salt" encompasses both "mono mesylate salt" and "dimesylate salt."

In some embodiments, provided herein is the dimesylate salt of Compound A ("Compound A•2MSA"). In some embodiments, the dimesylate salt of Compound A is referred to as "3-(4-(4-aminopiperidin-1-yl)-3-(3,5-difluorophenyl) quinolin-6-yl)-2-hydroxybenzonitrile dimesylate", "3-(4-(4-aminopiperidin-1-yl)-3-(3,5-difluorophenyl)quinolin-6-yl)-2-hydroxybenzonitrile dimethanesulfonic acid", or "3-(4-(4-aminopiperidin-1-yl)-3-(3,5-difluorophenyl)quinolin-6-yl)-2-hydroxybenzonitrile dimethanesulfonic acid salt".

Compound A•2MSA

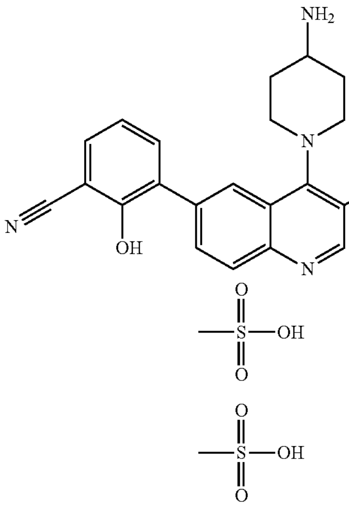

In some embodiments, Compound A•2MSA is amorphous.

In some embodiments, Compound A•2MSA is crystalline.

Amorphous Compound A•2MSA

Figure 2A:
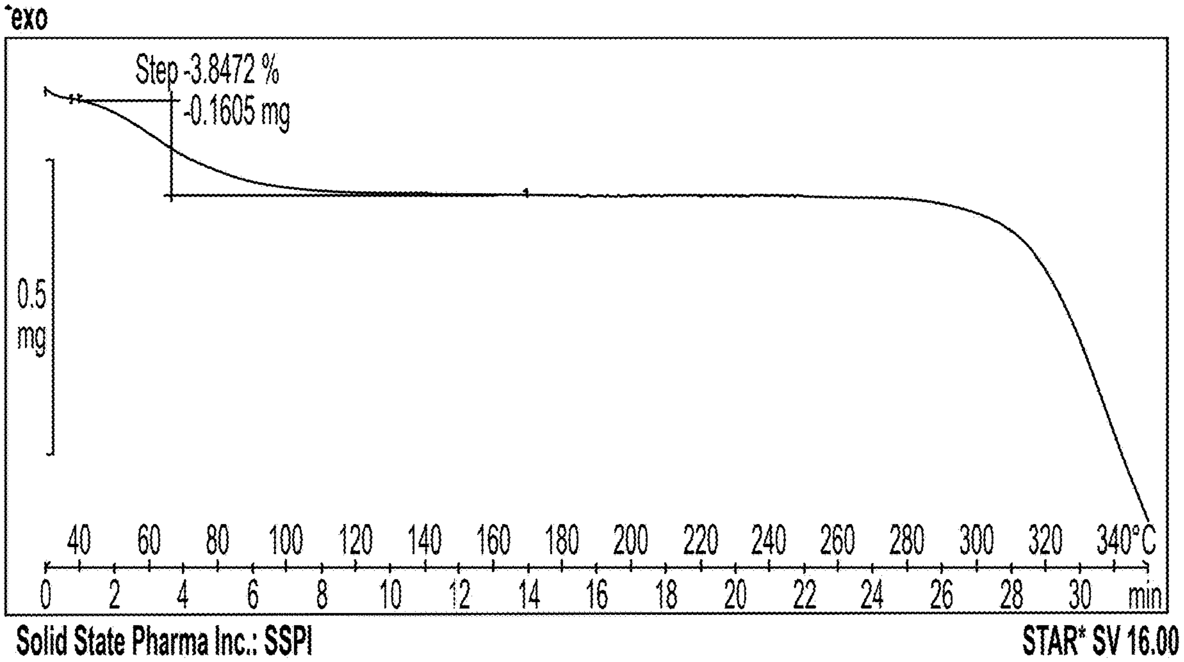
FIG. 2*a* shows the TGA pattern of amorphous Compound A•2MSA.

Provided herein is the amorphous solid form of 3-(4-(4-aminopiperidin-1-yl)-3-(3,5-difluorophenyl)quinolin-6-yl)-2-hydroxybenzonitrile dimesylate. Some embodiments provide a composition comprising the amorphous solid form of 3-(4-(4-aminopiperidin-1-yl)-3-(3,5-difluorophenyl)quinolin-6-yl)-2-hydroxybenzonitrile dimesylate. In some embodiments, the amorphous solid form of 3-(4-(4-aminopiperidin-1-yl)-3-(3,5-difluorophenyl)quinolin-6-yl)-2-hydroxybenzonitrile dimesylate has one of the following properties:

(a) an X-ray powder diffraction (XRPD) pattern showing a lack of crystallinity;

(b) a modulated Differential Scanning Calorimetry thermogram substantially the same as shown in FIG. 1;

(c) a modulated Differential Scanning Calorimetry thermogram with a glass transition temperature having an onset at about 166.6° C. and a midpoint at about 169.3° C.;

(d) a Thermogravimetric Analysis pattern substantially the same as shown in FIG. 2*a;*

(e) a Thermogravimetric Analysis pattern with a 3.85% w/w loss between 40 and 170° C.; or (f) a combination thereof.

In some embodiments, the amorphous solid form of 3-(4-(4-aminopiperidin-1-yl)-3-(3,5-difluorophenyl)quinolin-6-yl)-2-hydroxybenzonitrile dimesylate exhibits an X-ray powder diffraction (XRPD) pattern showing a lack of crystallinity. In some embodiments, the amorphous solid form of 3-(4-(4-aminopiperidin-1-yl)-3-(3,5-difluorophenyl)quinolin-6-yl)-2-hydroxybenzonitrile dimesylate exhibits a modulated Differential Scanning Calorimetry thermogram substantially the same as shown in FIG. 1. In some embodiments, the amorphous solid form of 3-(4-(4-aminopiperidin-1-yl)-3-(3,5-difluorophenyl)quinolin-6-yl)-2-hydroxybenzonitrile dimesylate exhibits a modulated Differential Scanning Calorimetry thermogram with a glass transition temperature having an onset at about 166.6° C. and a midpoint at about 169.3° C. In some embodiments, the amorphous solid form of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 2*a*. In some embodiments, the amorphous solid form of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 3.85% w/w loss between 40 and 170° C.

Crystalline Pattern a of Compound A•2MSA

Figure 3:
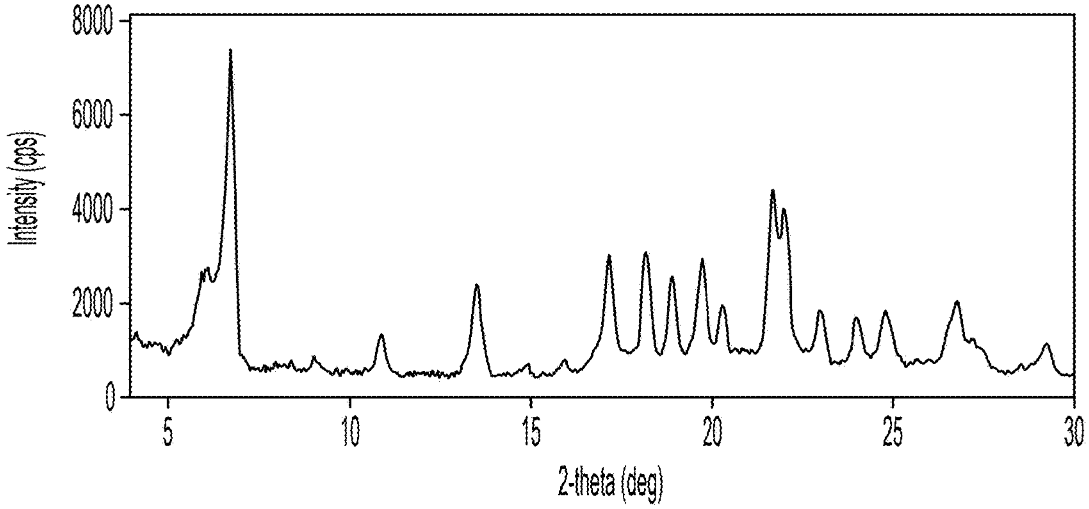
FIG. 3 shows the XRPD pattern of Compound A•2MSA Pattern A.
Figure 4:
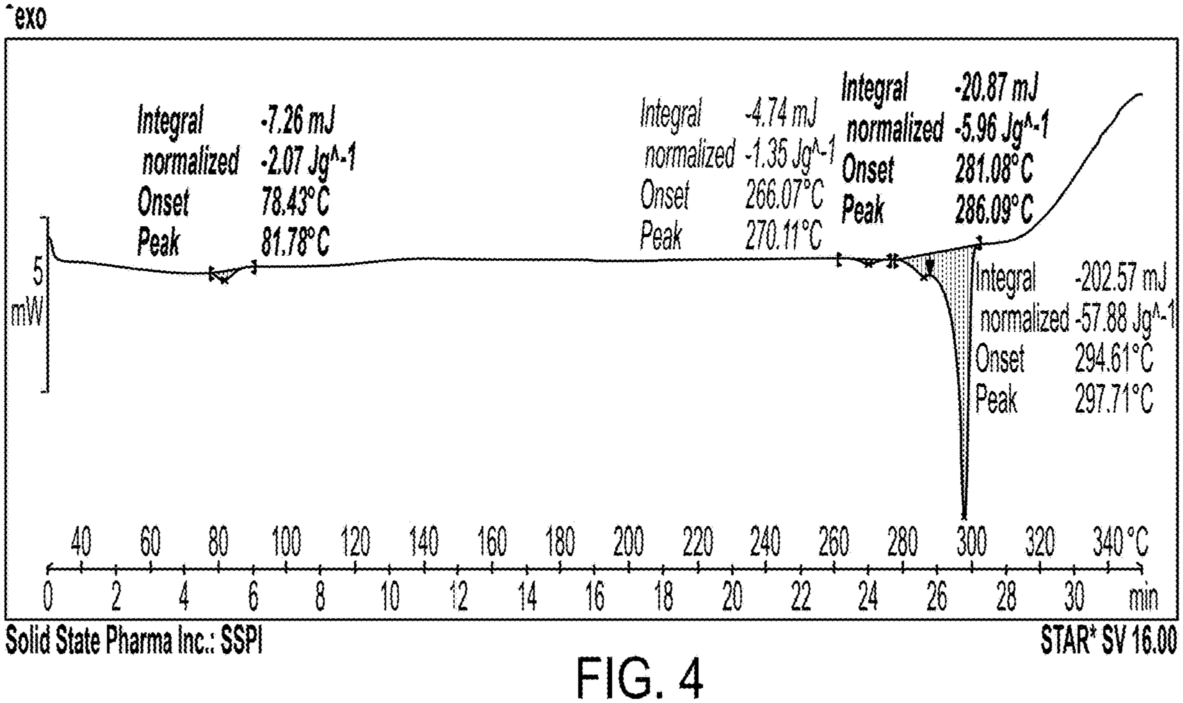
FIG. 4 shows the stand-alone DSC thermogram of Compound A•2MSA Pattern A.
Figure 6:
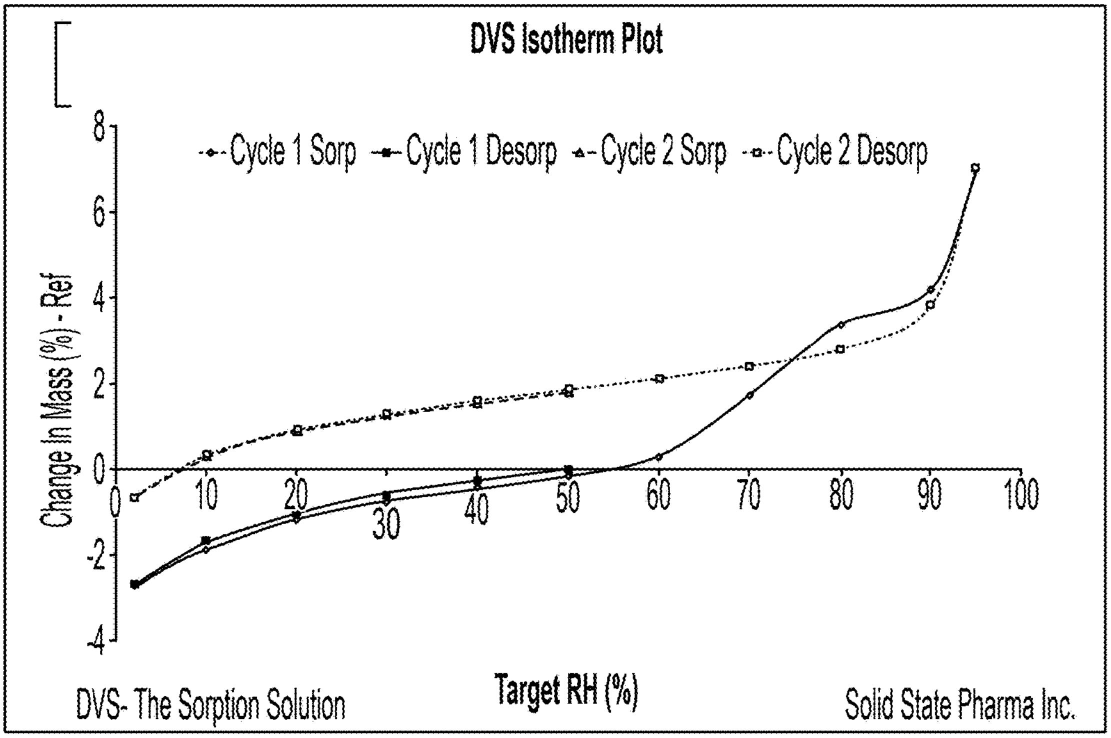
FIG. 6 shows the DVS isotherm plot of Compound A•2MSA Pattern A.

Also provided herein is the crystalline Pattern A of 3-(4-(4-aminopiperidin-1-yl)-3-(3,5-difluorophenyl)quinolin-6-yl)-2-hydroxybenzonitrile dimesylate. Some embodiments provide a composition comprising the crystalline Pattern A of 3-(4-(4-aminopiperidin-1-yl)-3-(3,5-difluorophenyl)quinolin-6-yl)-2-hydroxybenzonitrile dimesylate. In some embodiments, crystalline Pattern A of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 3;

(b) an X-ray powder diffraction pattern with X-ray diffraction pattern reflections at about 6.20° 2-Theta, about 6.76° 2-Theta, about 17.14° 2-Theta, and about 21.70° 2-Theta;

(c) a Differential Scanning Calorimetry thermogram substantially the same as shown in FIG. 4;

(d) a Differential Scanning Calorimetry thermogram with four endothermic events having: an onset at about 78.4° C. and a peak at about 81.8° C.; an onset at about 266.1° C. and a peak at about 270.1° C.; an onset at about 281.1° C. and a peak at about 286.1° C.; and an onset at about 294.6° C. and a peak at about 297.7° C.;

(e) a Thermogravimetric Analysis pattern substantially the same as shown in FIG. 4;

(f) a Thermogravimetric Analysis pattern with a 2.28% w/w loss from 60 to 180° C.;

(g) a Dynamic Vapour Sorption isotherm plot substantially the same as shown in FIG. 6;

(h) a reversible water uptake (9.8% w/w) between 2% and 95% Relative Humidity (RH);

(i) an XRPD that converts to Pattern B on storage at 75% RH and 40° C. for 7 days;

(j) an XRPD that converts to Pattern B on storage at 96% RH and 25° C. for 3 days;

(k) an unchanged XRPD after drying under dynamic vacuum at 50° C. for 2 hours;

(l) an XRPD that converts to Pattern P after heating to 255° C.;

(m) a 1.5% w/w water content; or (n) a combination thereof.

Figure 5A:
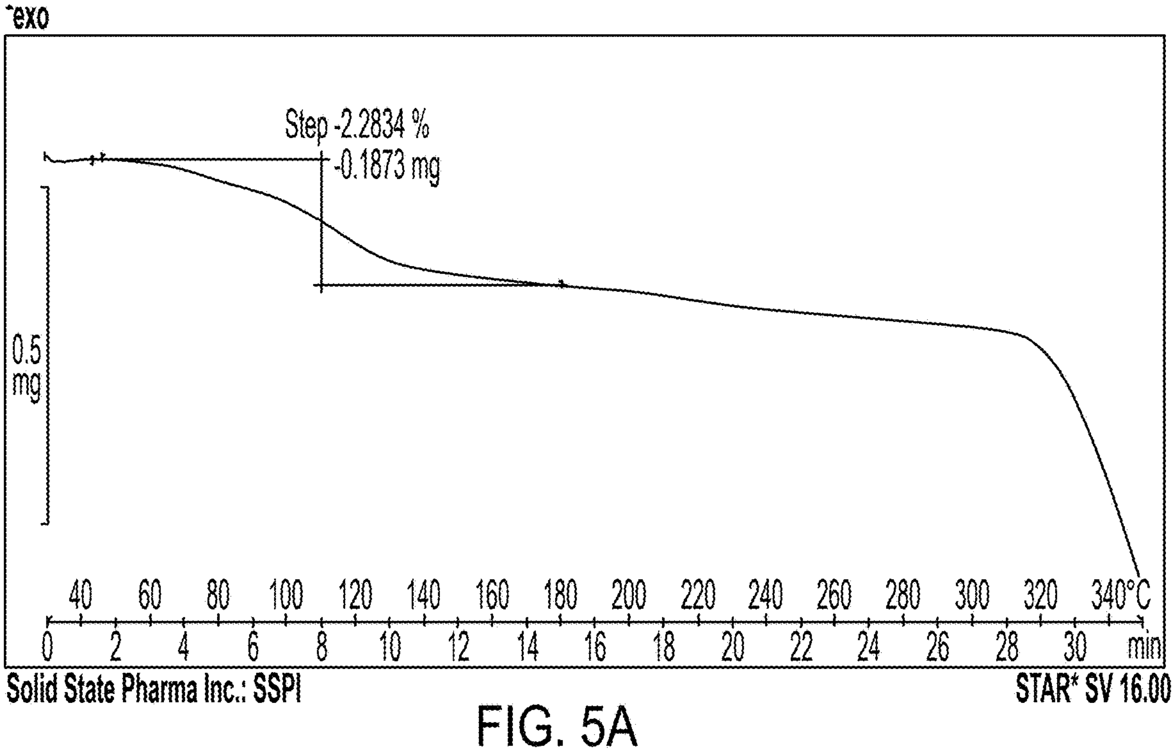
FIG. 5*a* shows the TGA pattern of Compound A•2MSA Pattern A.

In some embodiments, the crystalline Pattern A of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 3. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 6.20° 2-Theta, about 6.76° 2-Theta, about 17.14° 2-Theta, and about 21.70° 2-Theta. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 4. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with four endothermic events having: an onset at about 78.4° C. and a peak at about 81.8° C.; an onset at about 266.1° C. and a peak at about 270.1° C.; an onset at about 281.1° C. and a peak at about 286.1° C.; and an onset at about 294.6° C. and a peak at about 297.7° C. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 5*a*. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 2.28% w/w loss from 60 to 180° C. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits a Dynamic Vapour Sorption isotherm plot substantially the same as shown in FIG. 6. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits a reversible water uptake (9.8% w/w) between 2% and 95% Relative Humidity (RH). In some embodiments, the crystalline Pattern A of 3-(4-(4-aminopiperidin-1-yl)-3-(3,5-difluorophenyl)quinolin-6-yl)-2-hydroxybenzonitrile dimesylate exhibits an XRPD that converts to Pattern B on storage at 75% RH and 40° C. for 7 days. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits an XRPD that converts to Pattern B on storage at 96% RH and 25° C. for 3 days. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits an unchanged XRPD after drying under dynamic vacuum at 50° C. for 2 hours. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits an XRPD that converts to Pattern P after heating to 255° C. In some embodiments, the crystalline Pattern A of 3-(4-(4-aminopiperidin-1-yl)-3-(3,5-difluorophenyl)quinolin-6-yl)-2-hydroxybenzonitrile dimesylate exhibits a 1.5% w/w water content.

In some embodiments, the crystalline Pattern A of 3-(4-(4-aminopiperidin-1-yl)-3-(3,5-difluorophenyl)quinolin-6-yl)-2-hydroxybenzonitrile dimesylate has an X-ray diffraction pattern reflection at about 6.76° 2-Theta. In some embodiments, crystalline Pattern A is further characterized by X-ray diffraction pattern reflections at about 6.20° 2-Theta, about 17.14° 2-Theta, and about 21.70° 2-Theta. In some embodiments, crystalline Pattern A is further characterized by at least one X-ray diffraction pattern reflection selected from about 13.51° 2-Theta, about 18.21° 2-Theta, about 19.73° 2-Theta, about 22.02° 2-Theta, and about 26.77° 2-Theta.

Crystalline Hydrate Pattern B of Compound A•2MSA

Figure 7:
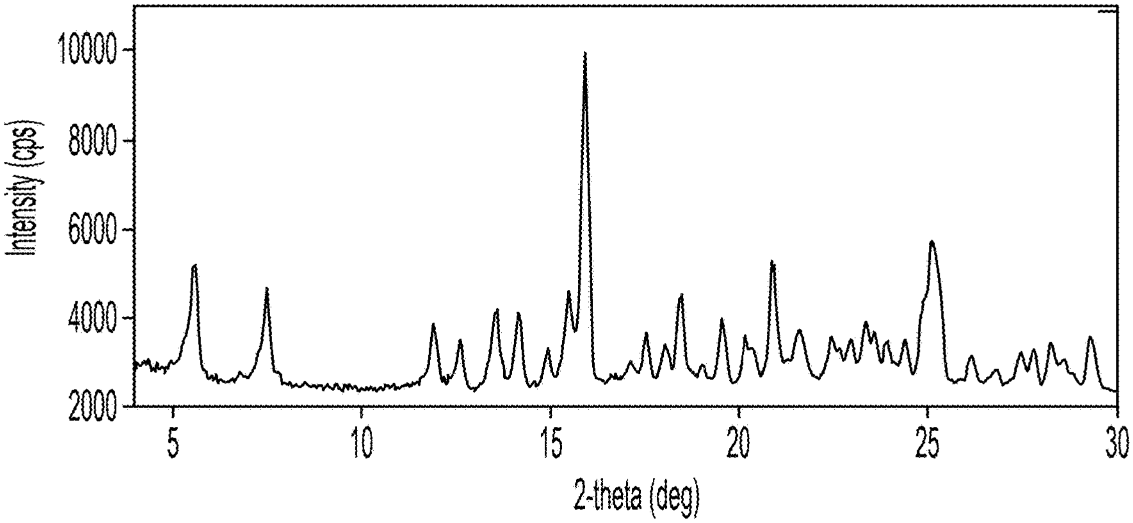
FIG. 7 shows the XRPD pattern of Compound A•2MSA Pattern B.
Figure 8:
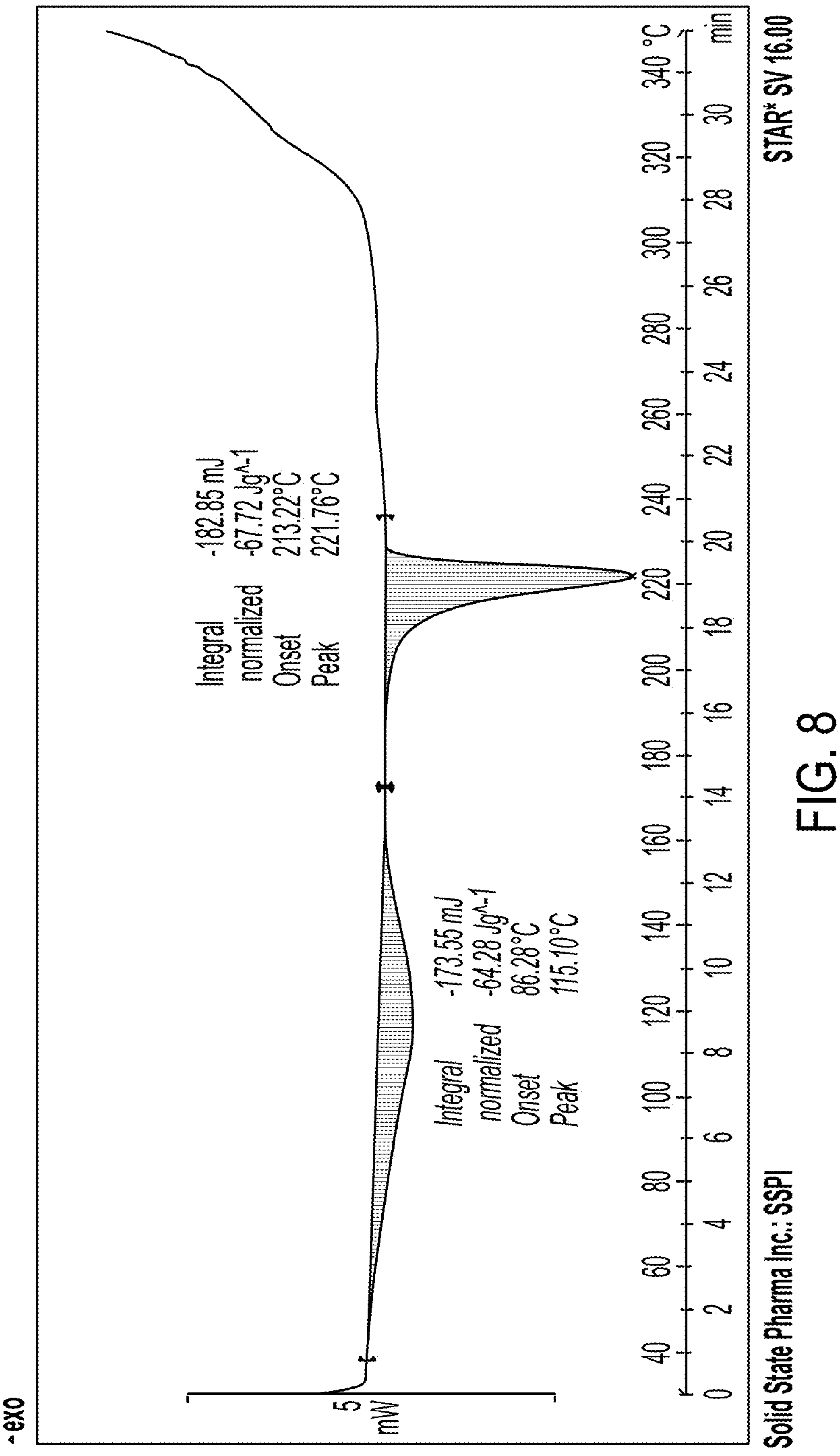
FIG. 8 shows the stand-alone DSC thermogram of Compound A•2MSA Pattern B.
Figure 9A:
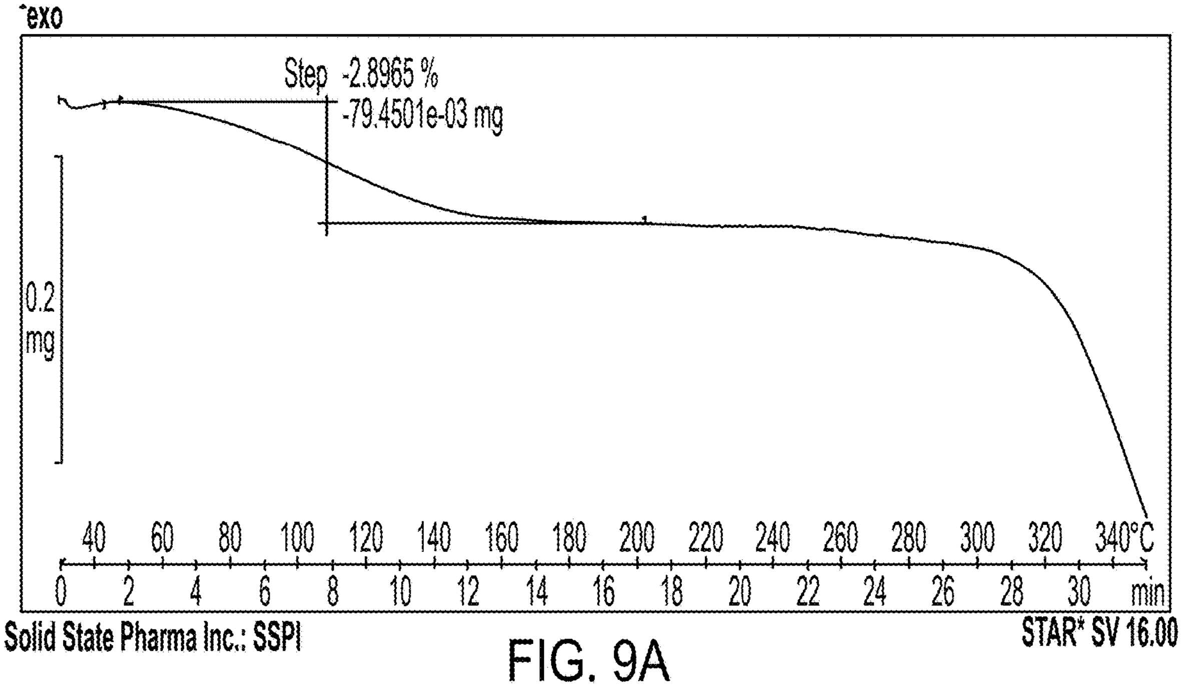
FIG. 9*a* shows the TGA pattern of Compound A•2MSA Pattern B.
Figure 10A:
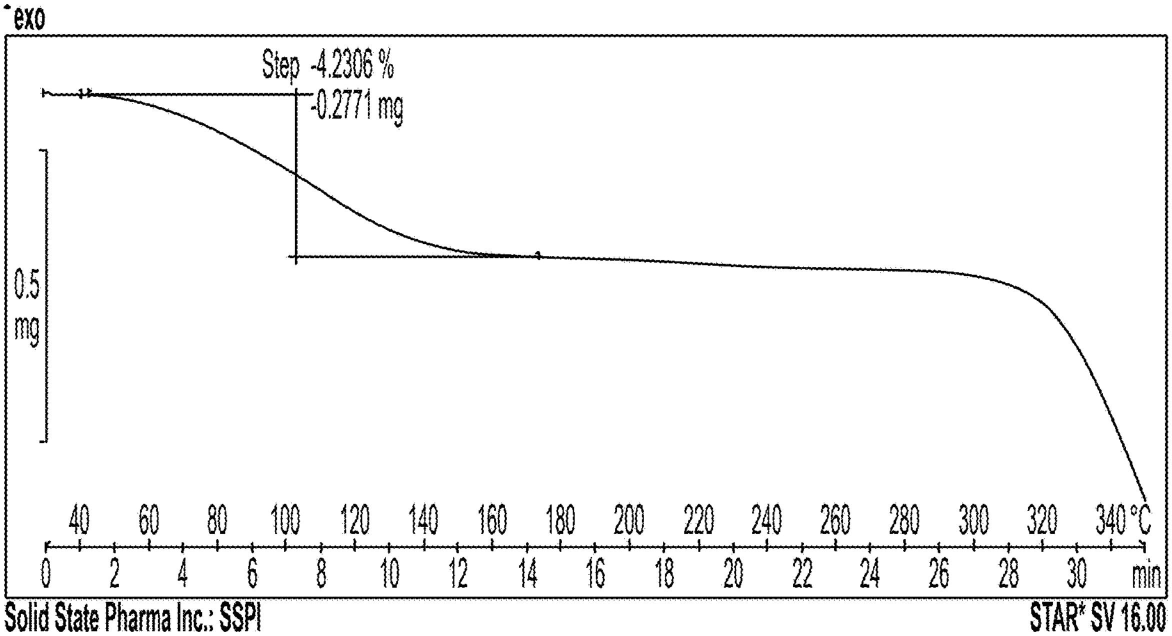
FIG. 10*a* shows the TGA pattern of Compound A•2MSA Pattern B after storage at ambient conditions for one week.
Figure 10B:
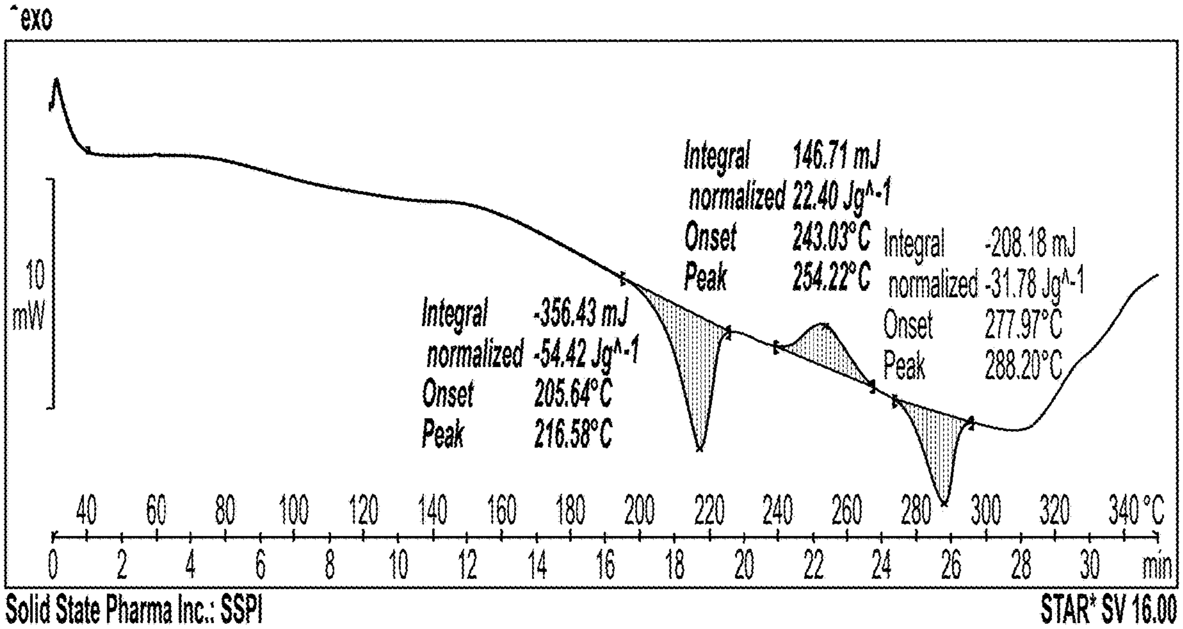
FIG. 10*b* shows the DSC thermogram of Compound A•2MSA Pattern B after storage at ambient conditions for one week.
Figure 11:
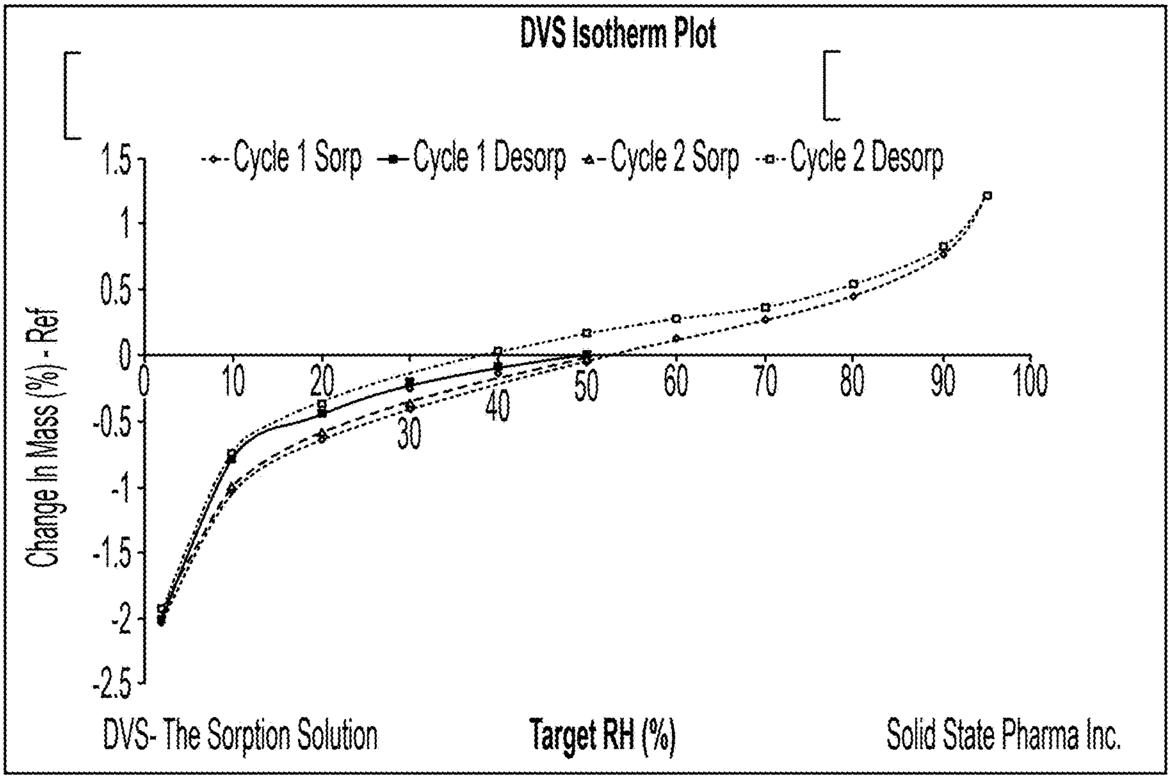
FIG. 11 shows the DVS isotherm plot of Compound A•2MSA Pattern B.

Also provided herein is the crystalline hydrate Pattern B of 3-(4-(4-aminopiperidin-1-yl)-3-(3,5-difluorophenyl)quinolin-6-yl)-2-hydroxybenzonitrile dimesylate. Some embodiments provide a composition comprising the crystalline hydrate Pattern B of 3-(4-(4-aminopiperidin-1-yl)-3-(3,5-difluorophenyl)quinolin-6-yl)-2-hydroxybenzonitrile dimesylate. In some embodiments, crystalline hydrate Pattern B of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 7;
(b) an X-ray powder diffraction pattern with X-ray diffraction pattern reflections at about 5.58° 2-Theta, about 7.48° 2-Theta, about 15.94° 2-Theta, and about 25.13° 2-Theta;
(c) a Differential Scanning Calorimetry thermogram substantially the same as shown in:
  FIG. 8; or FIG. 10*b;*
(d) a Differential Scanning Calorimetry thermogram with:
  a broad endothermic event having an onset at about 86.3° C. and a peak at about 115.1° C.; and an endothermic event having an onset at about 213.2° C. and a peak at about 221.8° C.; or an endothermic event having an onset at about 205.6° C. and a peak at about 221.8° C.; an exothermic event having an onset at about 243.0° C. and a peak at about 254.2° C.;
  and an endothermic event having an onset at about 278.0° C. and a peak at about 288.2° C.;
(e) a Thermogravimetric Analysis pattern substantially the same as shown in:
  FIG. 9*a*; or FIG. 10*a;*
(f) a Thermogravimetric Analysis pattern with:
  a 2.9% w/w loss from 40 to 205° C.; or
  a 4.23% w/w loss from 45 to 175° C.;
(g) a Dynamic Vapour Sorption isotherm plot substantially the same as shown in FIG. 11;
(h) a reversible water uptake (3.2% w/w) between 2% and 95% Relative Humidity (RH);
(i) an unchanged XRPD after DVS analysis at 95% RH and 25° C.;
(j) an unchanged XRPD after storage at 75% RH and 40° C. for 7 days;
(k) an unchanged XRPD after drying under dynamic vacuum at 50° C. for 2 hours;
(l) an unchanged XRPD after storage under static vacuum at 50° C. for 3 days;
(m) an XRPD that converts to Pattern I after heating to 270° C.;
(n) a 4.2% w/w water content; or
(o) a combination thereof.

In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 7. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 5.58° 2-Theta, about 7.48° 2-Theta, about 15.94° 2-Theta, and about 25.13° 2-Theta. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 8. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with a broad endothermic event having an onset at about 86.3° C. and a peak at about 115.1° C.; and an endothermic event having an onset at about 213.2° C. and a peak at about 221.8° C. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 10*b*. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with an endothermic event having an onset at about 205.6° C. and a peak at about 221.8° C.; an exothermic event having an onset at about 243.0° C. and a peak at about 254.2° C.; and an endothermic event having an onset at about 278.0° C. and a peak at about 288.2° C. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 9*a*. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 2.9% w/w loss from 40 to 205° C. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 10*a*. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 4.23% w/w loss from 45 to 175° C. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a Dynamic Vapour Sorption isotherm plot substantially the same as shown in FIG. 11. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a reversible water uptake (3.2% w/w) between 2% and 95% Relative Humidity (RH). In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits an unchanged XRPD after DVS analysis at 95% RH and 25° C. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits an unchanged XRPD after storage at 75% RH and 40° C. for 7 days. In some embodiments, the crystalline hydrate Pattern B of 3-(4-(4-aminopiperidin-1-yl)-3-(3,5-difluorophenyl) quinolin-6-yl)-2-hydroxybenzonitrile dimesylate exhibits an unchanged XRPD after drying under dynamic vacuum at 50° C. for 2 hours. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits an unchanged XRPD after storage under static vacuum at 50° C. for 3 days. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits an XRPD that converts to Pattern I after heating to 270° C. In some embodiments, the crystalline hydrate Pattern B of 3-(4-(4-aminopiperidin-1-yl)-3-(3,5-difluorophenyl)quinolin-6-yl)-2-hydroxybenzonitrile dimesylate exhibits a 4.2% w/w water content.

In some embodiments, the crystalline hydrate Pattern B of 3-(4-(4-aminopiperidin-1-yl)-3-(3,5-difluorophenyl)quinolin-6-yl)-2-hydroxybenzonitrile dimesylate has an X-ray diffraction pattern reflection at about 15.94° 2-Theta. In some embodiments, crystalline hydrate Pattern B is further characterized by X-ray diffraction pattern reflections at about 5.58° 2-Theta, about 7.48° 2-Theta, and about 25.13° 2-Theta. In some embodiments, crystalline hydrate Pattern B is further characterized by at least one X-ray diffraction pattern reflection selected from about 11.91° 2-Theta, about 13.58° 2-Theta, about 14.17° 2-Theta, about 15.51° 2-Theta, about 18.48° 2-Theta, about 20.91° 2-Theta, and about 28.26° 2-Theta.

Crystalline Pattern C of Compound A•2MSA

Figure 12:
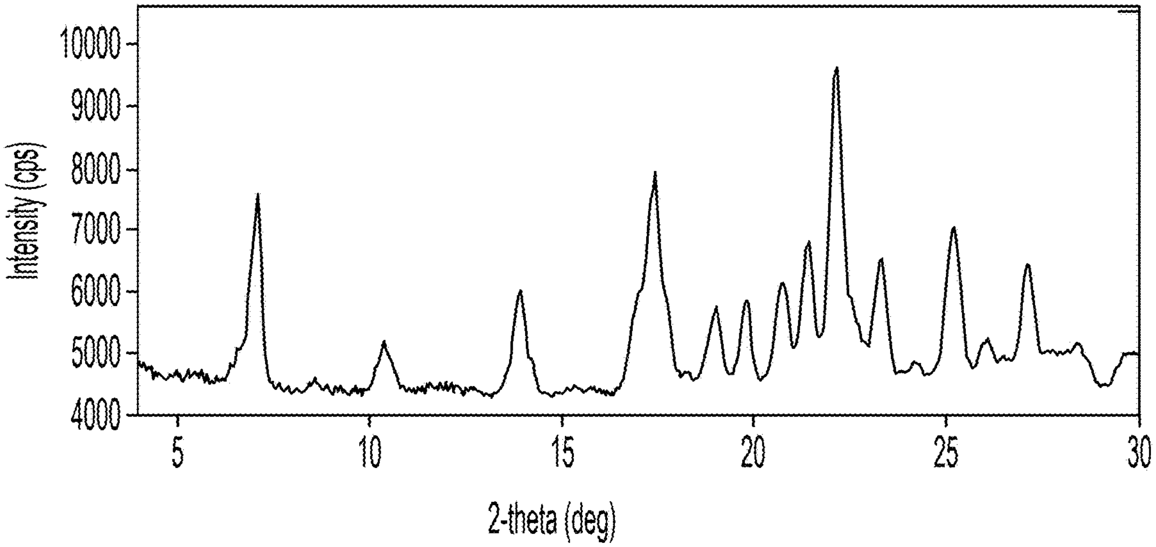
FIG. 12 shows the XRPD pattern of Compound A•2MSA Pattern C.
Figure 13:
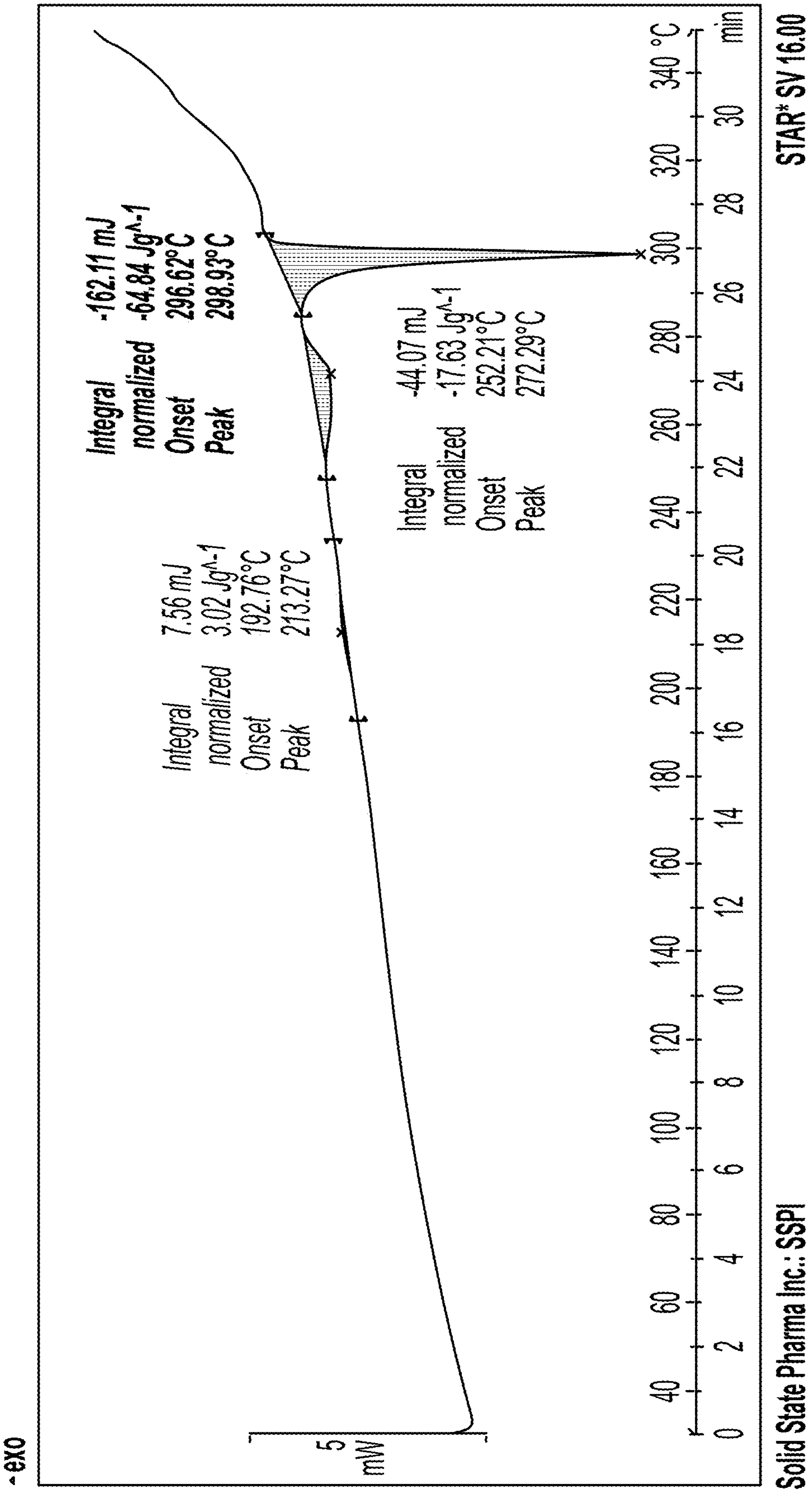
FIG. 13 shows the stand-alone DSC thermogram of Compound A•2MSA Pattern C.
Figure 14A:
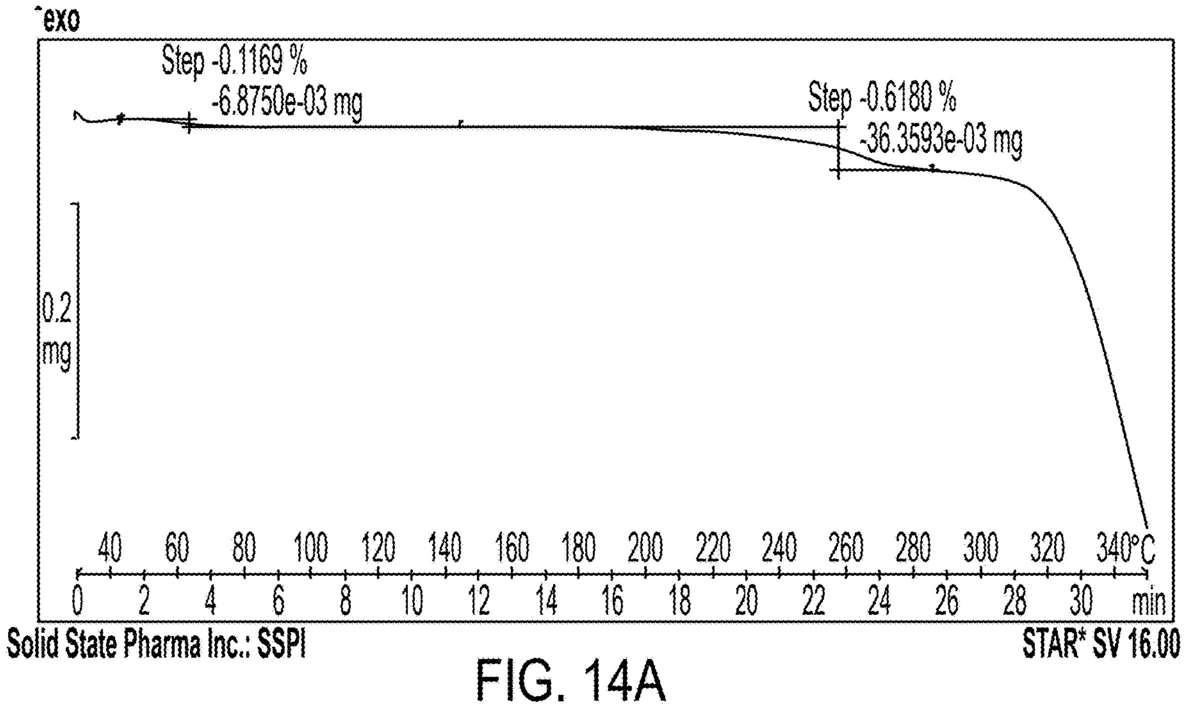
FIG. 14*a* shows the TGA pattern of Compound A•2MSA Pattern C.

Also provided herein is the crystalline Pattern C of 3-(4-(4-aminopiperidin-1-yl)-3-(3,5-difluorophenyl)quinolin-6-yl)-2-hydroxybenzonitrile dimesylate. Some embodiments provide a composition comprising the crystalline Pattern C of 3-(4-(4-aminopiperidin-1-yl)-3-(3,5-difluorophenyl)quinolin-6-yl)-2-hydroxybenzonitrile dimesylate. In some embodiments, crystalline Pattern C of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 12;

(b) an X-ray powder diffraction pattern with X-ray diffraction pattern reflections at about 7.10° 2-Theta, about 17.44° 2-Theta, about 22.18° 2-Theta, and about 25.20° 2-Theta;

(c) a Differential Scanning Calorimetry thermogram substantially the same as shown in FIG. 13;

(d) a Differential Scanning Calorimetry thermogram with an exothermic event having an onset at about 192.8° C. and a peak at about 213.3° C.; an endothermic event having an onset at about 252.2° C. and a peak at about 272.3° C.; and an endothermic event having an onset at about 296.6° C. and a peak at about 298.9° C.;

(e) a Thermogravimetric Analysis pattern substantially the same as shown in FIG. 14*a;*

(f) a Thermogravimetric Analysis pattern with a 0.12% w/w loss from 40 to 140° C. and a further 0.62% w/w loss from 140 to 290° C.;

(g) an unchanged XRPD after storage at 75% RH and 40° C. for 7 days;

(h) an unchanged XRPD after drying under dynamic vacuum at 50° C. for 2 hours;

(i) an XRPD that converts to Pattern I after heating to 240° C.; or (j) a combination thereof.

In some embodiments, the crystalline Pattern C of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 12. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 7.10° 2-Theta, about 17.44° 2-Theta, about 22.18° 2-Theta, and about 25.20° 2-Theta. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 13. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with an exothermic event having an onset at about 192.8° C. and a peak at about 213.3° C.; an endothermic event having an onset at about 252.2° C. and a peak at about 272.3° C.; and an endothermic event having an onset at about 296.6° C. and a peak at about 298.9° C. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 14*a*. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 0.12% w/w loss from 40 to 140° C. and a further 0.62% w/w loss from 140 to 290° C. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits an unchanged XRPD after storage at 75% RH and 40° C. for 7 days. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits an unchanged XRPD after drying under dynamic vacuum at 50° C. for 2 hours. In some embodiments, the crystalline Pattern C of 3-(4-(4-aminopiperidin-1-yl)-3-(3,5-difluorophenyl)quinolin-6-yl)-2-hydroxybenzonitrile dimesylate exhibits an XRPD that converts to Pattern I after heating to 240° C.

In some embodiments, the crystalline Pattern C of 3-(4-(4-aminopiperidin-1-yl)-3-(3,5-difluorophenyl)quinolin-6-yl)-2-hydroxybenzonitrile dimesylate has an X-ray diffraction pattern reflection at about 17.44° 2-Theta. In some embodiments, crystalline Pattern C is further characterized by X-ray diffraction pattern reflections at about 7.10° 2-Theta, about 22.18° 2-Theta, and about 25.20° 2-Theta. In some embodiments, crystalline Pattern C is further characterized by at least one X-ray diffraction pattern reflection selected from about 13.91° 2-Theta, about 19.02° 2-Theta, about 20.79° 2-Theta, about 21.44° 2-Theta, about 23.32° 2-Theta, and about 27.58° 2-Theta.

Crystalline Pattern I of Compound A•2MSA

Figure 15:
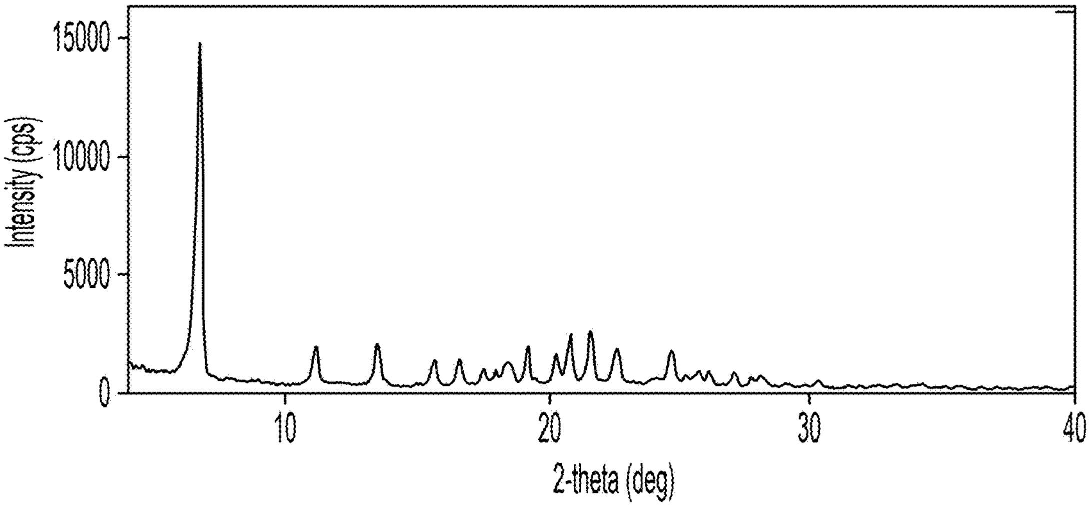
FIG. 15 shows the XRPD pattern of Compound A•2MSA Pattern I.
Figure 16:
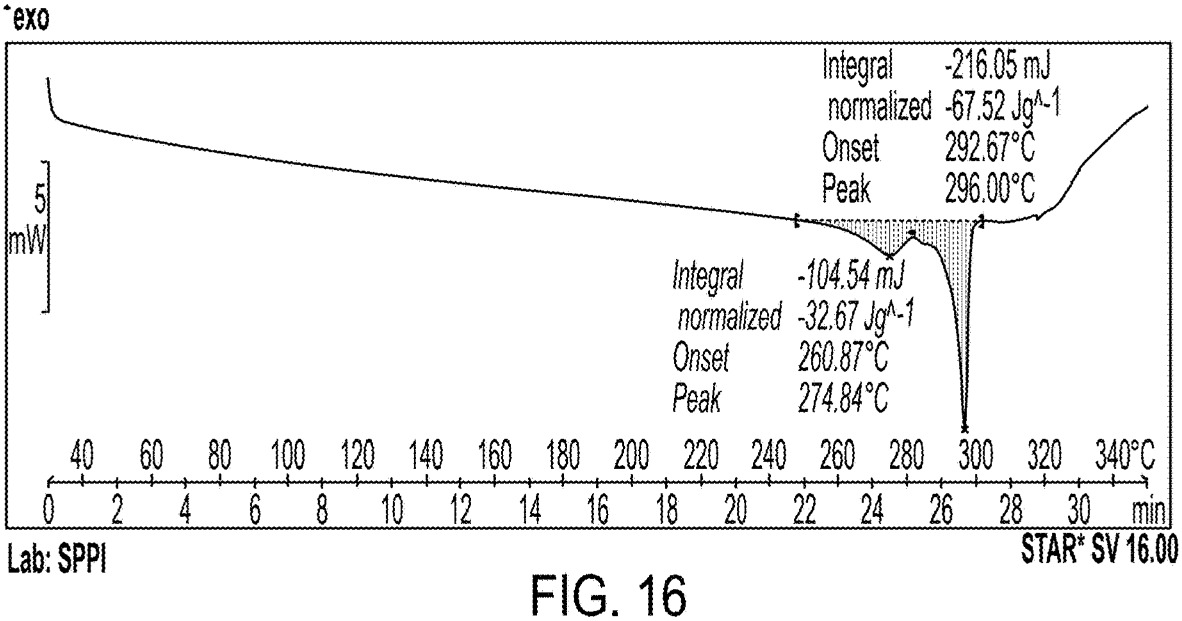
FIG. 16 shows the stand-alone DSC thermogram of Compound A•2MSA Pattern I.
Figure 17A:
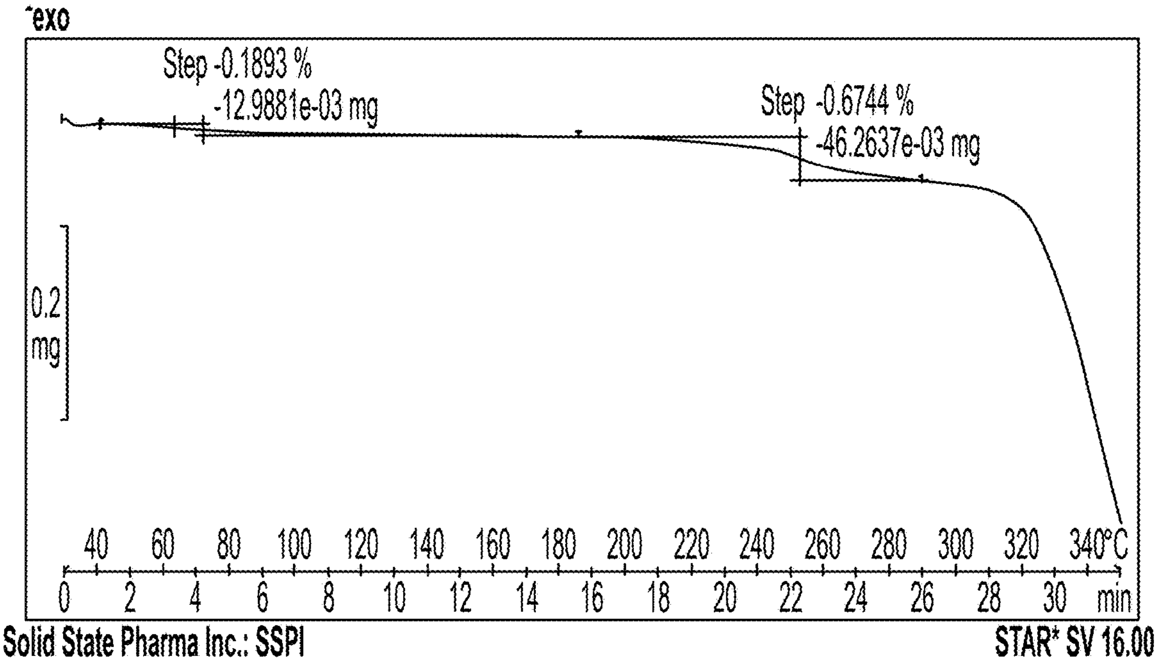
FIG. 17*a* shows the TGA pattern of Compound A•2MSA Pattern I.

Also provided herein is the crystalline Pattern I of 3-(4-(4-aminopiperidin-1-yl)-3-(3,5-difluorophenyl)quinolin-6-yl)-2-hydroxybenzonitrile dimesylate. Some embodiments provide a composition comprising the crystalline Pattern I of 3-(4-(4-aminopiperidin-1-yl)-3-(3,5-difluorophenyl)quinolin-6-yl)-2-hydroxybenzonitrile dimesylate. In some embodiments, crystalline Pattern I of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 15;

(b) an X-ray powder diffraction pattern with X-ray diffraction pattern reflections at about 6.74° 2-Theta, about 11.17° 2-Theta, about 20.83° 2-Theta, and about 21.65° 2-Theta;

(c) a Differential Scanning Calorimetry thermogram substantially the same as shown in FIG. 16;

(d) a Differential Scanning Calorimetry thermogram with an endothermic event having an onset at about 260.9° C. and a peak at about 274.8° C.; and an endothermic event having an onset at about 292.7° C. and a peak at about 296.0° C.;

(e) a Thermogravimetric Analysis pattern substantially the same as shown in FIG. 17*a;*

Figure 18:
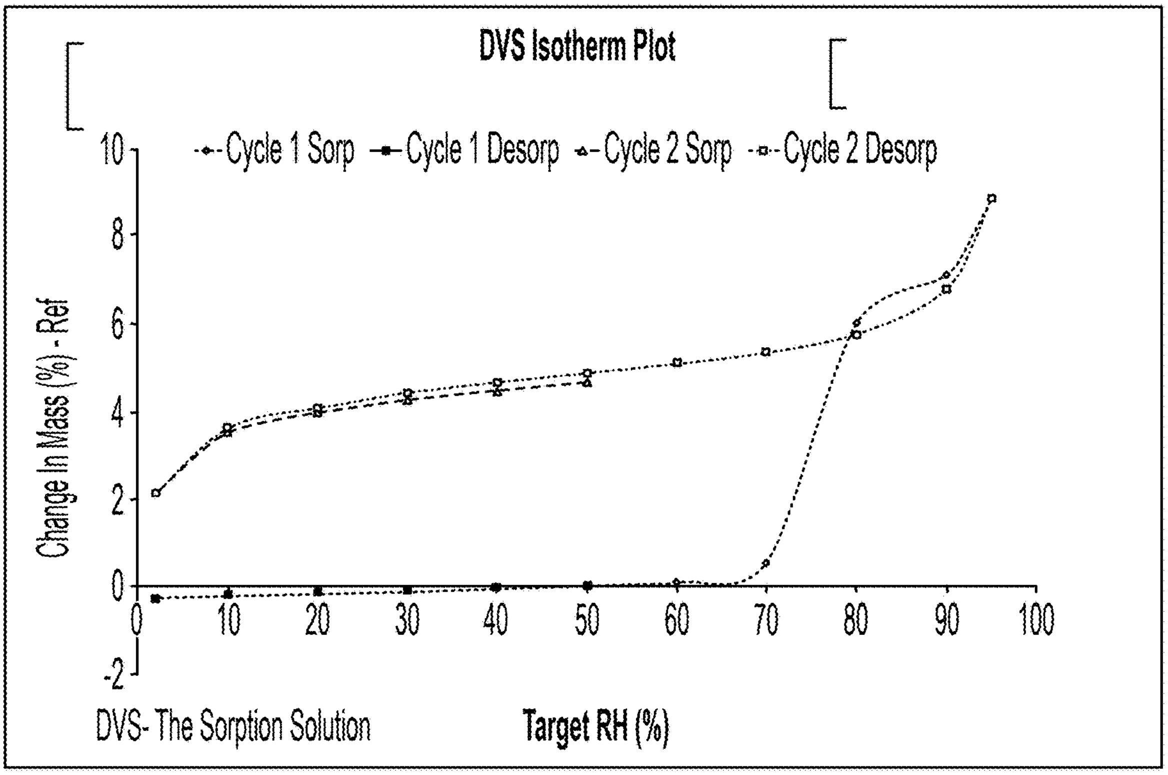
FIG. 18 shows the DVS isotherm plot of Compound A•2MSA Pattern I.

(f) a Thermogravimetric Analysis pattern with a 0.19% w/w loss from 40 to 185° C. and a further 0.67% w/w loss from 185 to 290° C.;

(g) a Dynamic Vapour Sorption isotherm plot substantially the same as shown in FIG. 18;

(h) a reversible water uptake (9.1% w/w) between 2% and 95% Relative Humidity (RH); with a 2.5% w/w water uptake between 15 and 75% RH;

(i) an XRPD that converts to Pattern B after DVS analysis between 2% and 95% RH and 25° C.;

(j) an unchanged XRPD after storage at 75% RH and 40° C. for 7 days;

(k) an unchanged XRPD after drying under dynamic vacuum at 50° C. for 2 hours;

(l) a 0.29% w/w water content; or (m) a combination thereof.

In some embodiments, the crystalline Pattern I of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 15. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 6.74° 2-Theta, about 11.17° 2-Theta, about 20.83° 2-Theta, and about 21.65° 2-Theta. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 16. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with an endothermic event having an onset at about 260.9° C. and a peak at about 274.8° C.; and an endothermic event having an onset at about 292.7° C. and a peak at about 296.0° C. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 17*a*. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 0.19% w/w loss from 40 to 185° C. and a further 0.67% w/w loss from 185 to 290° C. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits a Dynamic Vapour Sorption isotherm plot substantially the same as shown in FIG. 18. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits a reversible water uptake (9.1% w/w) between 2% and 95% Relative Humidity (RH); with a 2.5% w/w water uptake between 15 and 75% RH. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits an XRPD that converts to Pattern B after DVS analysis between 2% and 95% RH and 25° C. In some embodiments, the crystalline Pattern I of 3-(4-(4-aminopiperidin-1-yl)-3-(3,5-difluorophenyl) quinolin-6-yl)-2-hydroxybenzonitrile dimesylate exhibits an unchanged XRPD after storage at 75% RH and 40° C. for 7 days. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits an unchanged XRPD after drying under dynamic vacuum at 50° C. for 2 hours. In some embodiments, the crystalline Pattern I of 3-(4-(4-aminopiperidin-1-yl)-3-(3,5-difluorophenyl)quinolin-6-yl)-2-hydroxybenzonitrile dimesylate exhibits a 0.29% w/w water content.

In some embodiments, the crystalline Pattern I of 3-(4-(4-aminopiperidin-1-yl)-3-(3,5-difluorophenyl)quinolin-6-yl)-2-hydroxybenzonitrile dimesylate has an X-ray diffraction pattern reflection at about 6.74° 2-Theta. In some embodiments, crystalline Pattern I is further characterized by X-ray diffraction pattern reflections at about 11.17° 2-Theta, about 20.83° 2-Theta, and about 21.65° 2-Theta. In some embodiments, crystalline Pattern I is further characterized by at least one X-ray diffraction pattern reflection selected from about 13.50° 2-Theta, about 18.49° 2-Theta, about 19.21° 2-Theta, about 22.58° 2-Theta, and about 24.69° 2-Theta.

Crystalline Isopropanol Solvate Pattern D of Compound A•2MSA

Figure 19:
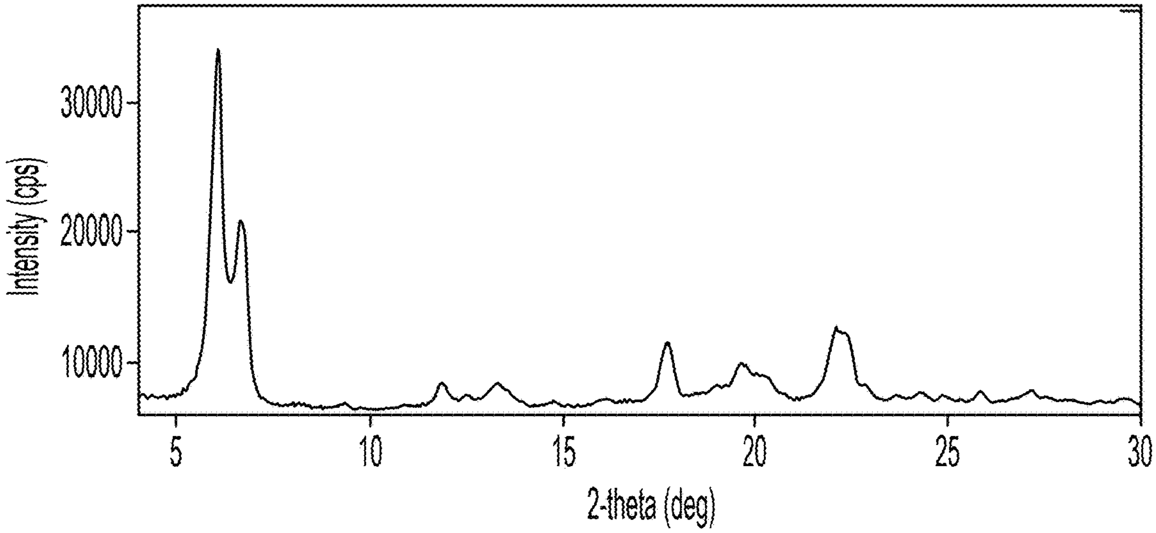
FIG. 19 shows the XRPD pattern of Compound A•2MSA Pattern D.

Also provided herein is the crystalline isopropanol solvate Pattern D of 3-(4-(4-aminopiperidin-1-yl)-3-(3,5-difluorophenyl)quinolin-6-yl)-2-hydroxybenzonitrile dimesylate. Some embodiments provide a composition comprising the crystalline isopropanol solvate Pattern D of 3-(4-(4-aminopiperidin-1-yl)-3-(3,5-difluorophenyl)quinolin-6-yl)-2-hydroxybenzonitrile dimesylate. In some embodiments, crystalline isopropanol solvate Pattern D of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 19;

(b) an X-ray powder diffraction pattern with X-ray diffraction pattern reflections at about 6.10° 2-Theta, about 6.70° 2-Theta, about 17.75° 2-Theta, and about 22.22° 2-Theta;

(c) an XRPD that converts to Pattern A after drying under dynamic vacuum at 50° C. for 2 hours; or (d) a combination thereof.

In some embodiments, the crystalline isopropanol solvate Pattern D of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 19. In some embodiments, the crystalline isopropanol solvate Pattern D of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 6.10° 2-Theta, about 6.70° 2-Theta, about 17.75° 2-Theta, and about 22.22° 2-Theta. In some embodiments, the crystalline isopropanol solvate Pattern D of 3-(4-(4-aminopiperidin-1-yl)-3-(3,5-difluorophenyl)quinolin-6-yl)-2-hydroxybenzonitrile dimesylate exhibits an XRPD that converts to Pattern A after drying under dynamic vacuum at 50° C. for 2 hours.

In some embodiments, the crystalline isopropanol solvate Pattern D of 3-(4-(4-aminopiperidin-1-yl)-3-(3,5-difluorophenyl)quinolin-6-yl)-2-hydroxybenzonitrile dimesylate has an X-ray diffraction pattern reflection at about 6.10° 2-Theta. In some embodiments, crystalline isopropanol solvate Pattern D is further characterized by X-ray diffraction pattern reflections at about 6.70° 2-Theta, about 17.75° 2-Theta, and about 22.22° 2-Theta. In some embodiments, crystalline isopropanol solvate Pattern D is further characterized by at least one X-ray diffraction pattern reflection selected from about 13.31° 2-Theta, about 19.17° 2-Theta, and about 20.21° 2-Theta.

Crystalline Tetrahydrofuran Solvate Pattern E of Compound A•2MSA

Figure 20:
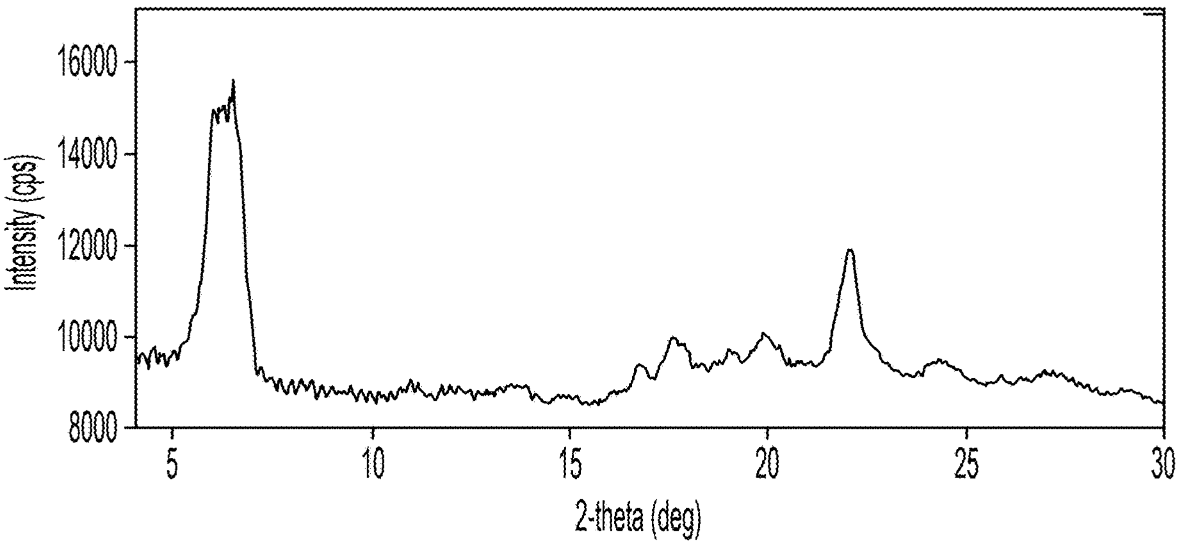
FIG. 20 shows the XRPD pattern of Compound A•2MSA Pattern E.

Also provided herein is the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate. Some embodiments provide a composition comprising the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate. In some embodiments, crystalline tetrahydrofuran solvate Pattern E of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 20;

(b) an X-ray powder diffraction pattern with X-ray diffraction pattern reflections at about 6.42° 2-Theta, about 19.99° 2-Theta, and about 21.12° 2-Theta;

(c) an XRPD that converts to Pattern A after drying under dynamic vacuum at 50° C. for 2 hours; or (d) a combination thereof.

In some embodiments, the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 20. In some embodiments, the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 6.42° 2-Theta, about 19.99° 2-Theta, and about 21.12° 2-Theta. In some embodiments, the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate exhibits an XRPD that converts to Pattern A after drying under dynamic vacuum at 50° C. for 2 hours.

In some embodiments, the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate has an X-ray diffraction pattern reflection at about 6.42° 2-Theta. In some embodiments, crystalline tetrahydrofuran solvate Pattern E is further characterized by X-ray diffraction pattern reflections at about 19.99° 2-Theta, and about 21.12° 2-Theta. In some embodiments, crystalline tetrahydrofuran solvate Pattern E is further characterized by an X-ray diffraction pattern reflection at about 17.76° 2-Theta.

Crystalline Methyl Isobutyl Ketone Solvate Pattern F of Compound A•2MSA

Figure 21:
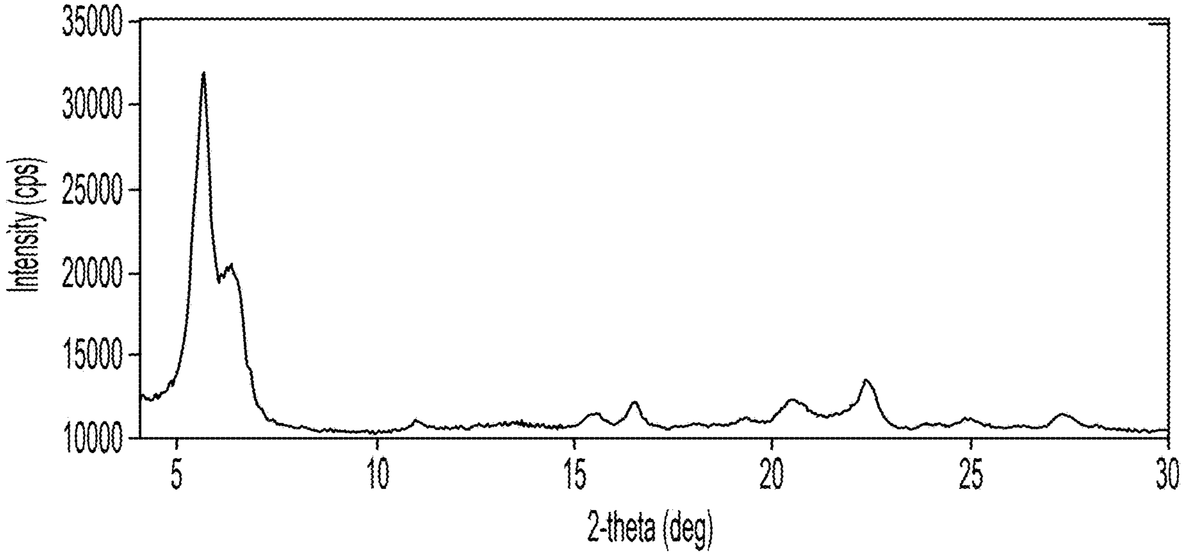
FIG. 21 shows the XRPD pattern of Compound A•2MSA Pattern F.

Also provided herein is the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate. Some embodiments provide a composition comprising the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate. In some embodiments, crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 21;

(b) an X-ray powder diffraction pattern with X-ray diffraction pattern reflections at about 5.63° 2-Theta, about 6.27° 2-Theta, about 20.55° 2-Theta, and about 22.33° 2-Theta;

(c) an XRPD that converts to Pattern I after drying under dynamic vacuum at 50° C. for 2 hours; or (d) a combination thereof.

In some embodiments, the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 21. In some embodiments, the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 5.63° 2-Theta, about 6.27° 2-Theta, about 20.55° 2-Theta, and about 22.33° 2-Theta. In some embodiments, the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate exhibits an XRPD that converts to Pattern I after drying under dynamic vacuum at 50° C. for 2 hours.

In some embodiments, the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate has an X-ray diffraction pattern reflection at about 6.27° 2-Theta. In some embodiments, crystalline tetrahydrofuran solvate Pattern E is further characterized by X-ray diffraction pattern reflections at about 5.63° 2-Theta, about 20.55° 2-Theta, and about 22.33° 2-Theta. In some embodiments, crystalline methyl isobutyl ketone solvate Pattern F is further characterized by at least one X-ray diffraction pattern reflection selected from about 16.51° 2-Theta, and about 27.25° 2-Theta.

Crystalline Ethyl Acetate Solvate Pattern G of Compound A•2MSA

Figure 22:
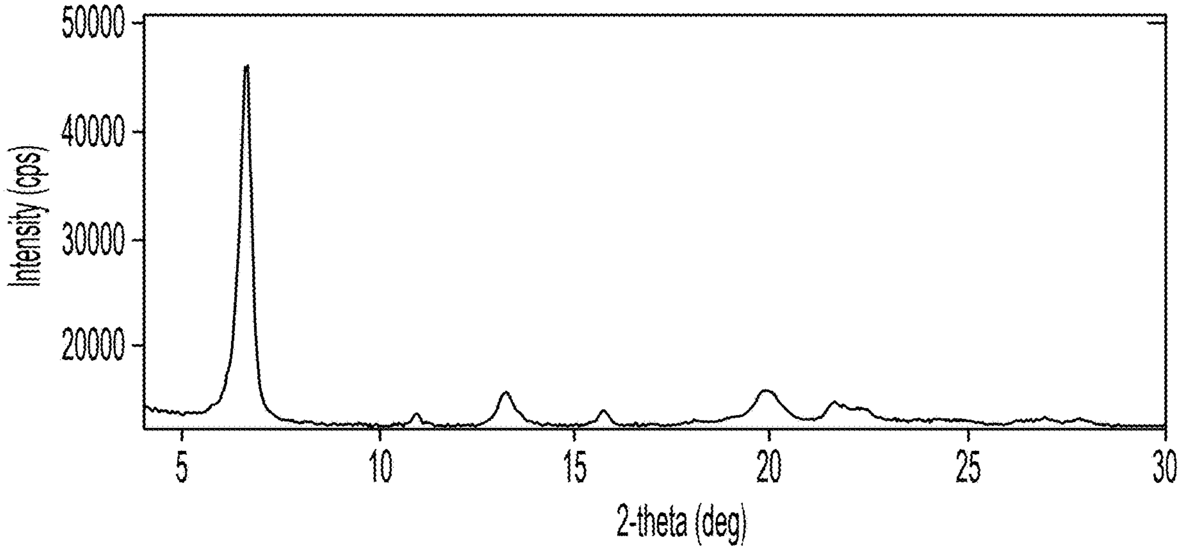
FIG. 22 shows the XRPD pattern of Compound A•2MSA Pattern G.

Also provided herein is the crystalline ethyl acetate solvate Pattern G of 3-(4-(4-aminopiperidin-1-yl)-3-(3,5-difluorophenyl)quinolin-6-yl)-2-hydroxybenzonitrile dimesylate. Some embodiments provide a composition comprising the crystalline ethyl acetate solvate Pattern G of 3-(4-(4-aminopiperidin-1-yl)-3-(3,5-difluorophenyl)quinolin-6-yl)-2-hydroxybenzonitrile dimesylate. In some embodiments, crystalline ethyl acetate solvate Pattern G of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 22;

(b) an X-ray powder diffraction pattern with X-ray diffraction pattern reflections at about 6.62° 2-Theta, about 13.21° 2-Theta, about 19.79° 2-Theta, and about 21.72° 2-Theta;

(c) an XRPD that converts to Pattern I after drying under dynamic vacuum at 50° C. for 2 hours; or (d) a combination thereof.

In some embodiments, the crystalline ethyl acetate solvate Pattern G of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 22. In some embodiments, the crystalline ethyl acetate solvate Pattern G of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 6.62° 2-Theta, about 13.21° 2-Theta, about 19.79° 2-Theta, and about 21.72° 2-Theta. In some embodiments, the crystalline ethyl acetate solvate Pattern G of 3-(4-(4-aminopiperidin-1-yl)-3-(3,5-difluorophenyl)quinolin-6-yl)-2-hydroxybenzonitrile dimesylate exhibits an XRPD that converts to Pattern I after drying under dynamic vacuum at 50° C. for 2 hours.

In some embodiments, the crystalline ethyl acetate solvate Pattern G of 3-(4-(4-aminopiperidin-1-yl)-3-(3,5-difluorophenyl)quinolin-6-yl)-2-hydroxybenzonitrile dimesylate has an X-ray diffraction pattern reflection at about 6.62° 2-Theta. In some embodiments, crystalline ethyl acetate solvate Pattern G is further characterized by X-ray diffraction pattern reflections at about 13.21° 2-Theta, about 19.79° 2-Theta, and about 21.72° 2-Theta.

Crystalline Isopropyl Acetate Solvate Pattern H of Compound A•2MSA

Figure 23:
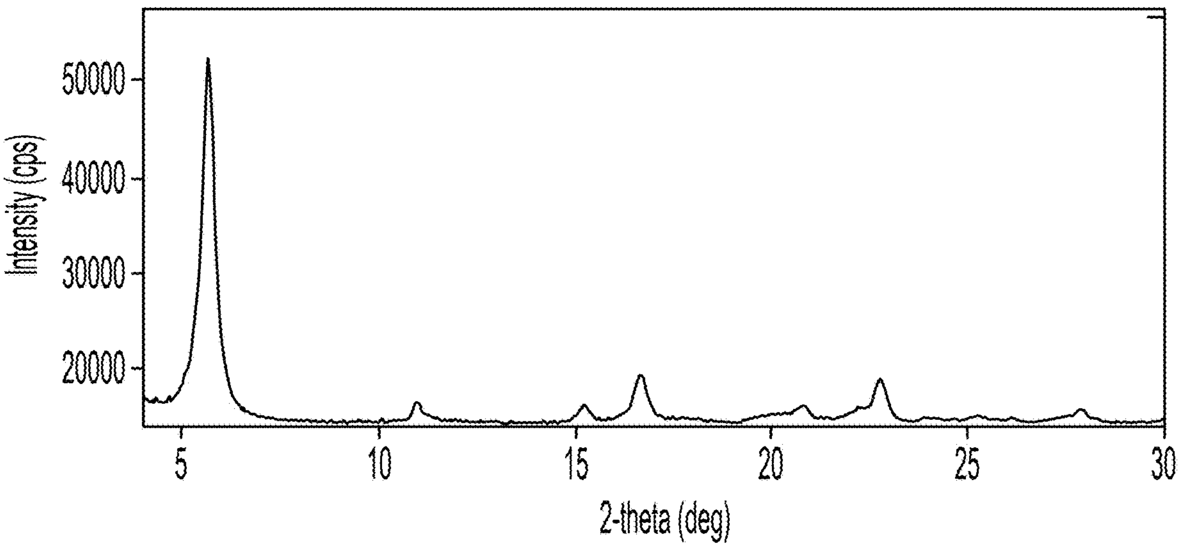
FIG. 23 shows the XRPD pattern of Compound A•2MSA Pattern H.

Also provided herein is the crystalline isopropyl acetate solvate Pattern H of 3-(4-(4-aminopiperidin-1-yl)-3-(3,5-difluorophenyl)quinolin-6-yl)-2-hydroxybenzonitrile dimesylate. Some embodiments provide a composition comprising the crystalline isopropyl acetate solvate Pattern H of 3-(4-(4-aminopiperidin-1-yl)-3-(3,5-difluorophenyl)quinolin-6-yl)-2-hydroxybenzonitrile dimesylate. In some embodiments, crystalline isopropyl acetate solvate Pattern H of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 23;

(b) an X-ray powder diffraction pattern with X-ray diffraction pattern reflections at about 5.66° 2-Theta, about 16.77° 2-Theta, and about 22.78° 2-Theta;

(c) an XRPD that converts to Pattern I after drying under dynamic vacuum at 50° C. for 2 hours; or (d) a combination thereof.

In some embodiments, the crystalline isopropyl acetate solvate Pattern H of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 23. In some embodiments, the crystalline isopropyl acetate solvate Pattern H of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 5.66° 2-Theta, about 16.77° 2-Theta, and about 22.78° 2-Theta. In some embodiments, the crystalline isopropyl acetate solvate Pattern H of 3-(4-(4-aminopiperidin-1-yl)-3-(3,5-difluorophenyl)quinolin-6-yl)-2-hydroxybenzonitrile dimesylate exhibits an XRPD that converts to Pattern I after drying under dynamic vacuum at 50° C. for 2 hours.

In some embodiments, the crystalline isopropyl acetate solvate Pattern H of 3-(4-(4-aminopiperidin-1-yl)-3-(3,5-difluorophenyl)quinolin-6-yl)-2-hydroxybenzonitrile dimesylate has an X-ray diffraction pattern reflection at about 5.66° 2-Theta. In some embodiments, crystalline isopropyl acetate solvate Pattern H is further characterized by X-ray diffraction pattern reflections at about 16.77° 2-Theta, and about 22.78° 2-Theta. In some embodiments, crystalline methyl isobutyl ketone solvate Pattern F is further characterized by at least one X-ray diffraction pattern reflection selected from about 10.93° 2-Theta, and about 20.83° 2-Theta.

Crystalline Pattern J of Compound A•2MSA

Figure 24:
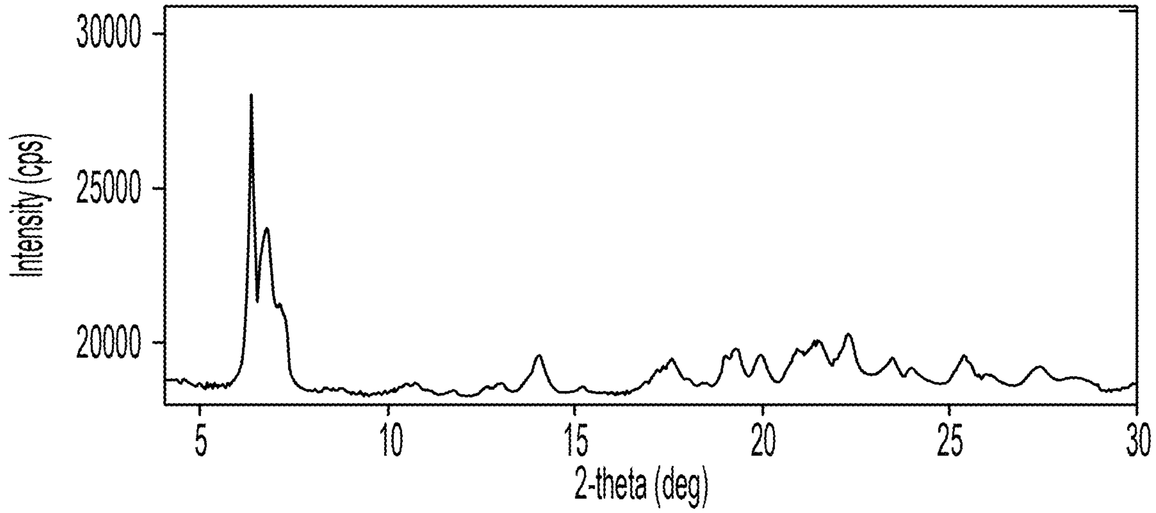
FIG. 24 shows the XRPD pattern of Compound A•2MSA Pattern J.

Also provided herein is the crystalline Pattern J of 3-(4-(4-aminopiperidin-1-yl)-3-(3,5-difluorophenyl)quinolin-6-yl)-2-hydroxybenzonitrile dimesylate. Some embodiments provide a composition comprising the crystalline Pattern J of 3-(4-(4-aminopiperidin-1-yl)-3-(3,5-difluorophenyl)quinolin-6-yl)-2-hydroxybenzonitrile dimesylate. In some embodiments, crystalline Pattern J of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 24;

(b) an X-ray powder diffraction pattern with X-ray diffraction pattern reflections at about 6.32° 2-Theta, about 6.72° 2-Theta, about 12.33° 2-Theta, and about 21.47° 2-Theta; or (c) a combination thereof.

In some embodiments, the crystalline Pattern J of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 24. In some embodiments, the crystalline Pattern J of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 6.32° 2-Theta, about 6.72° 2-Theta, about 12.33° 2-Theta, and about 21.47° 2-Theta.

In some embodiments, the crystalline Pattern J of 3-(4-(4-aminopiperidin-1-yl)-3-(3,5-difluorophenyl)quinolin-6-yl)-2-hydroxybenzonitrile dimesylate has an X-ray diffraction pattern reflection at about 6.72° 2-Theta. In some embodiments, crystalline Pattern J is further characterized by X-ray diffraction pattern reflections at about 6.32° 2-Theta, about 12.33° 2-Theta, and about 21.47° 2-Theta. In some embodiments, crystalline Pattern J is further characterized by at least one X-ray diffraction pattern reflection selected from about 14.07° 2-Theta, about 17.50° 2-Theta, and about 22.31° 2-Theta.

Crystalline Pattern K of Compound A•2MSA

Figure 25:
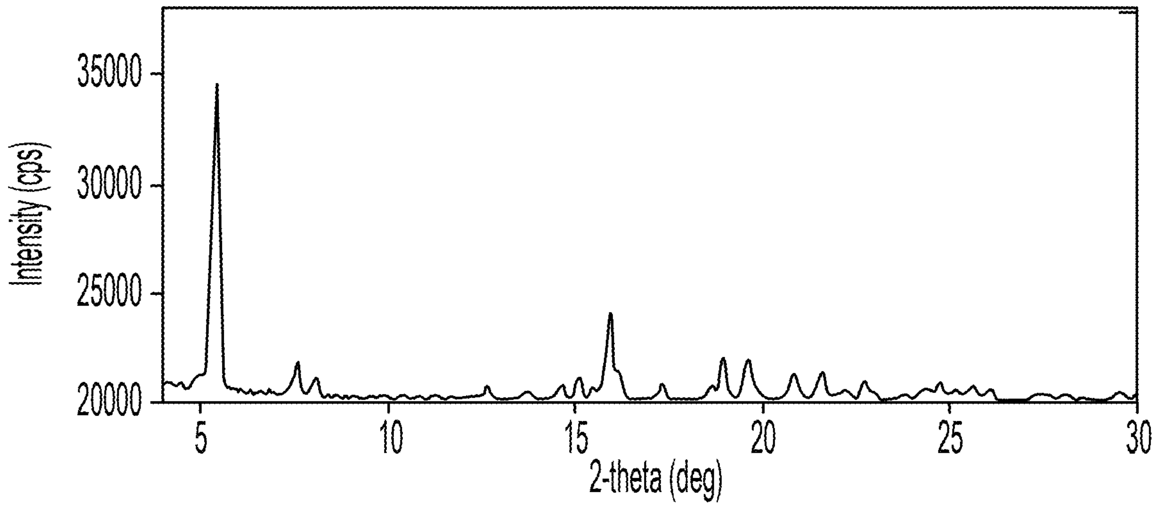
FIG. 25 shows the XRPD pattern of Compound A•2MSA Pattern K.
Figure 26A:
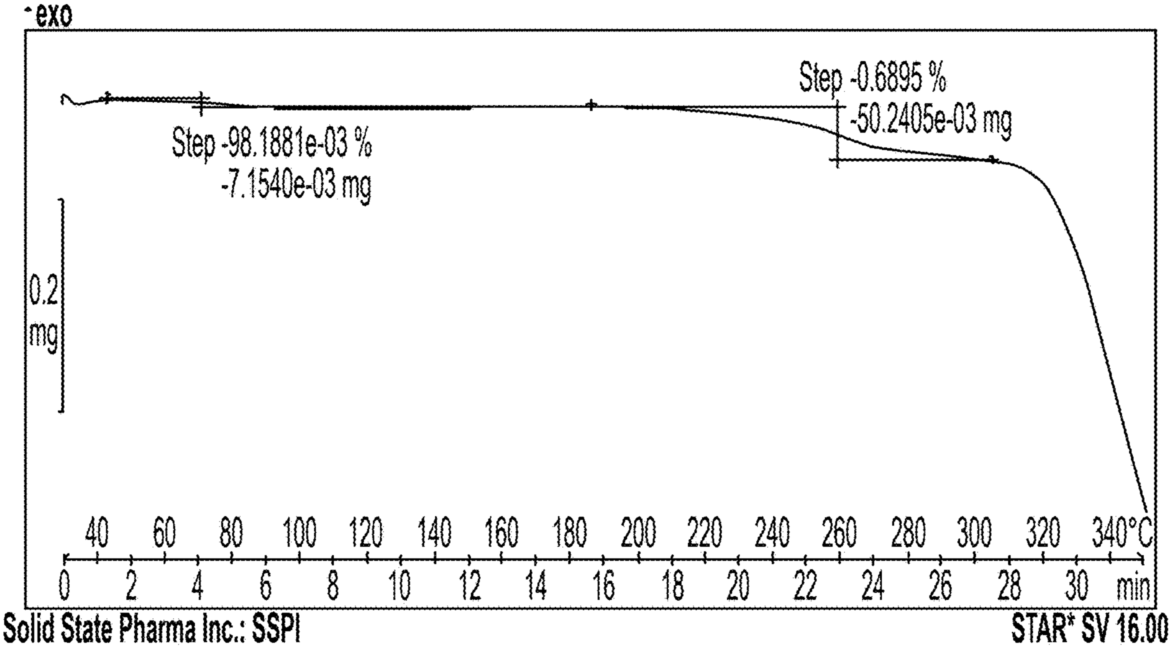
FIG. 26*a* shows the TGA pattern of Compound A•2MSA Pattern K.
Figure 26B:
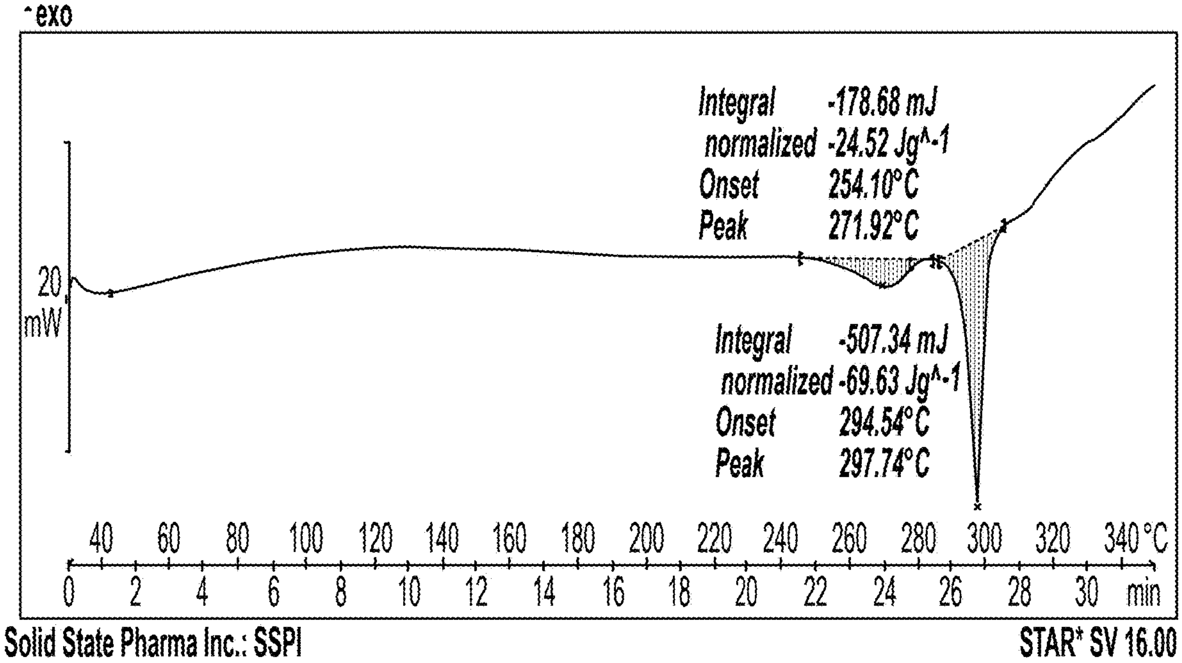
FIG. 26*b* shows the DSC thermogram of Compound A•2MSA Pattern K.

Also provided herein is the crystalline Pattern K of 3-(4-(4-aminopiperidin-1-yl)-3-(3,5-difluorophenyl)quinolin-6-yl)-2-hydroxybenzonitrile dimesylate. Some embodiments provide a composition comprising the crystalline Pattern K of 3-(4-(4-aminopiperidin-1-yl)-3-(3,5-difluorophenyl)quinolin-6-yl)-2-hydroxybenzonitrile dimesylate. In some embodiments, crystalline Pattern K of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 25;

(b) an X-ray powder diffraction pattern with X-ray diffraction pattern reflections at about 5.42° 2-Theta, about 15.90° 2-Theta, about 19.59° 2-Theta, and about 21.52° 2-Theta;

(c) a Differential Scanning Calorimetry thermogram substantially the same as shown in FIG. 26*b;*

(d) a Differential Scanning Calorimetry thermogram with an endothermic event having an onset at about 254.1° C. and a peak at about 271.9° C.; and an endothermic event having an onset at about 294.5° C. and a peak at about 297.7° C.;

(e) a Thermogravimetric Analysis pattern substantially the same as shown in FIG. 26*a;*

(f) a Thermogravimetric Analysis pattern with a 0.1% w/w loss from 40 to 190° C. and a further 0.69% w/w loss from 190 to 310° C.;

(g) an unchanged XRPD after drying under dynamic vacuum at 50° C. for 2 hours; or (h) a combination thereof.

In some embodiments, the crystalline Pattern K of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 25. In some embodiments, the crystalline Pattern K of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 5.42° 2-Theta, about 15.90° 2-Theta, about 19.59° 2-Theta, and about 21.52° 2-Theta. In some embodiments, the crystalline Pattern K of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 26*b*. In some embodiments, the crystalline Pattern K of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with an endothermic event having an onset at about 254.1° C. and a peak at about 271.9° C.; and an endothermic event having an onset at about 294.5° C. and a peak at about 297.7° C. In some embodiments, the crystalline Pattern K of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 26*a*. In some embodiments, the crystalline Pattern K of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 0.1% w/w loss from 40 to 190° C. and a further 0.69% w/w loss from 190 to 310° C. In some embodiments, the crystalline Pattern K of 3-(4-(4-aminopiperidin-1-yl)-3-(3,5-difluorophenyl)quinolin-6-yl)-2-hydroxybenzonitrile dimesylate exhibits an unchanged XRPD after drying under dynamic vacuum at 50° C. for 2 hours.

In some embodiments, the crystalline Pattern K of 3-(4-(4-aminopiperidin-1-yl)-3-(3,5-difluorophenyl)quinolin-6-yl)-2-hydroxybenzonitrile dimesylate has an X-ray diffraction pattern reflection at about 5.42° 2-Theta. In some embodiments, crystalline Pattern K is further characterized by X-ray diffraction pattern reflections at about 15.90° 2-Theta, about 19.59° 2-Theta, and about 21.52° 2-Theta. In some embodiments, crystalline Pattern K is further characterized by at least one X-ray diffraction pattern reflection selected from about 7.57° 2-Theta, about 8.05° 2-Theta, about 12.62° 2-Theta, about 15.09° 2-Theta, about 18.64° 2-Theta, about 18.92° 2-Theta, about 20.82° 2-Theta, about 22.69° 2-Theta, and about 29.48° 2-Theta.

Crystalline Acetone Solvate Pattern M of Compound A•2MSA

Figure 27:
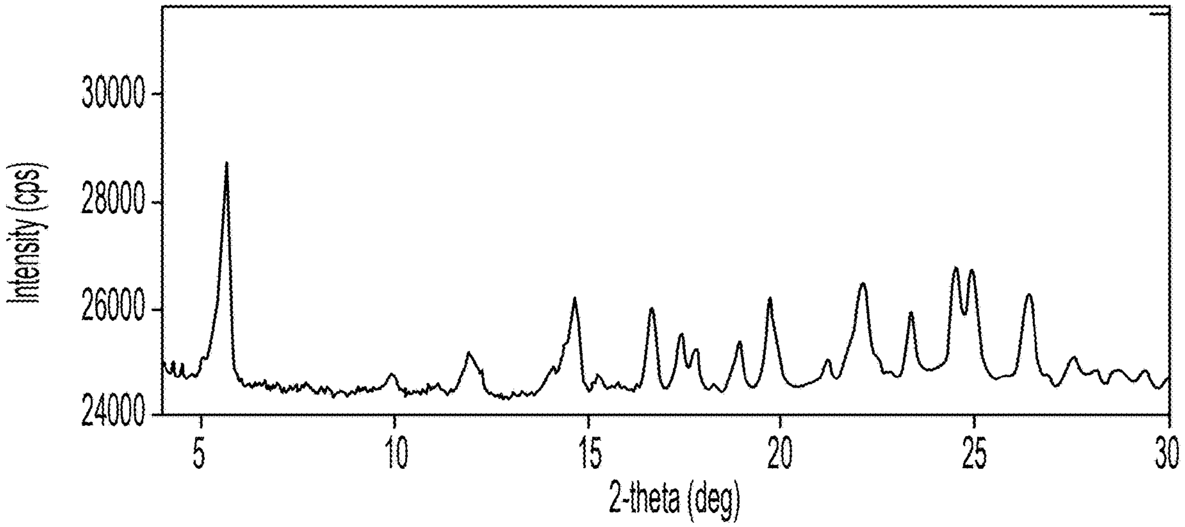
FIG. 27 shows the XRPD pattern of Compound A•2MSA Pattern M.

Also provided herein is the crystalline acetone solvate Pattern M of 3-(4-(4-aminopiperidin-1-yl)-3-(3,5-difluorophenyl)quinolin-6-yl)-2-hydroxybenzonitrile dimesylate. Some embodiments provide a composition comprising the crystalline acetone solvate Pattern M of 3-(4-(4-aminopiperidin-1-yl)-3-(3,5-difluorophenyl)quinolin-6-yl)-2-hydroxybenzonitrile dimesylate. In some embodiments, crystalline acetone solvate Pattern M of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 27;

(b) an X-ray powder diffraction pattern with X-ray diffraction pattern reflections at about 5.67° 2-Theta, about 14.63° 2-Theta, about 22.14° 2-Theta, and about 24.91° 2-Theta; or (c) a combination thereof.

In some embodiments, the crystalline acetone solvate Pattern M of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 27. In some embodiments, the crystalline acetone solvate Pattern M of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 5.67° 2-Theta, about 14.63° 2-Theta, about 22.14° 2-Theta, and about 24.91° 2-Theta.

In some embodiments, the crystalline acetone solvate Pattern M of 3-(4-(4-aminopiperidin-1-yl)-3-(3,5-difluorophenyl)quinolin-6-yl)-2-hydroxybenzonitrile dimesylate has an X-ray diffraction pattern reflection at about 5.67° 2-Theta. In some embodiments, crystalline acetone solvate Pattern M is further characterized by X-ray diffraction pattern reflections at about 14.63° 2-Theta, about 22.14° 2-Theta, and about 24.91° 2-Theta. In some embodiments, crystalline acetone solvate Pattern M is further characterized by at least one X-ray diffraction pattern reflection selected from about 11.94° 2-Theta, about 16.67° 2-Theta, about 19.70° 2-Theta, about 23.33° 2-Theta, about 24.46° 2-Theta, and about 26.35° 2-Theta.

Crystalline Acetonitrile Solvate Pattern N of Compound A•2MSA

Figure 28:
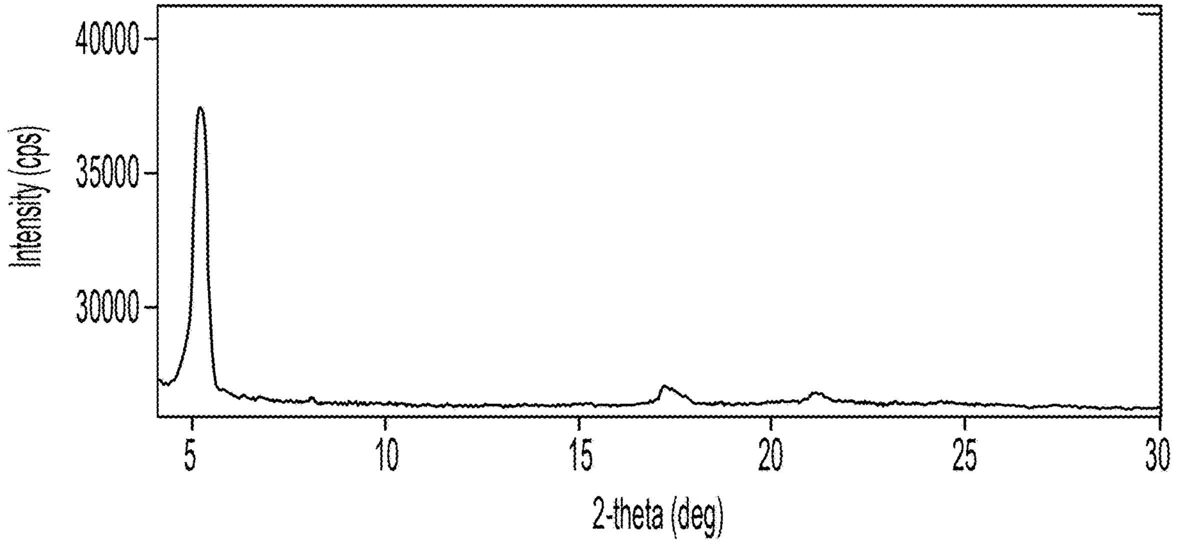
FIG. 28 shows the XRPD pattern of Compound A•2MSA Pattern N.
Figure 29A:
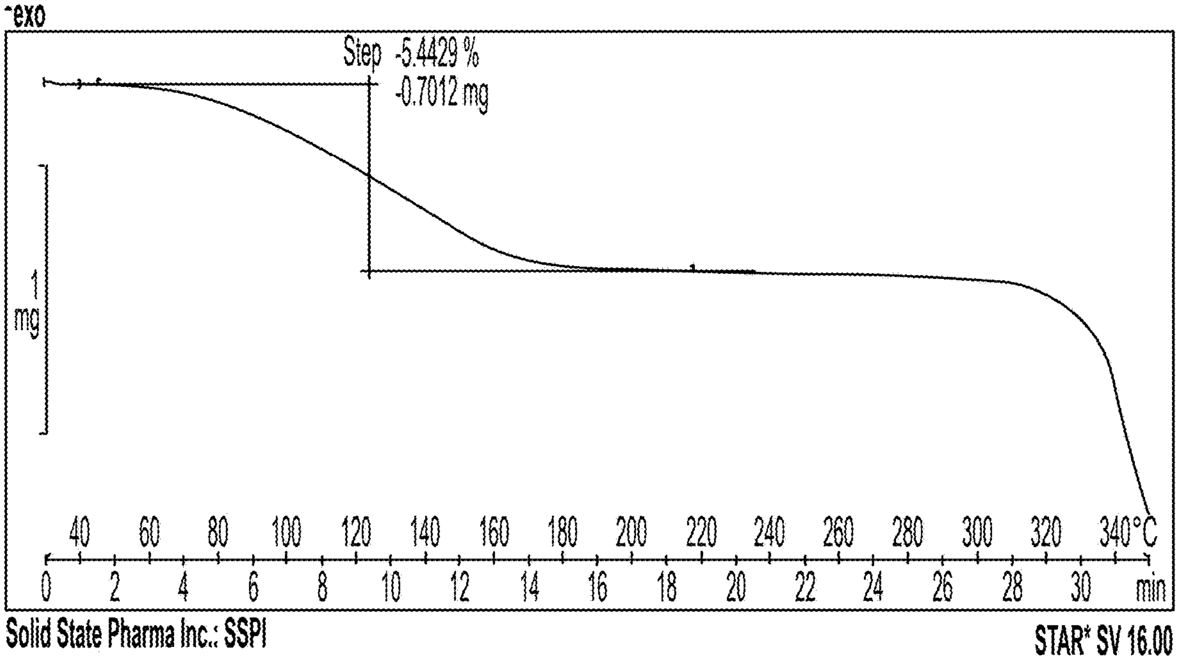
FIG. 29*a* shows the TGA pattern of Compound A•2MSA Pattern N.
Figure 29B:
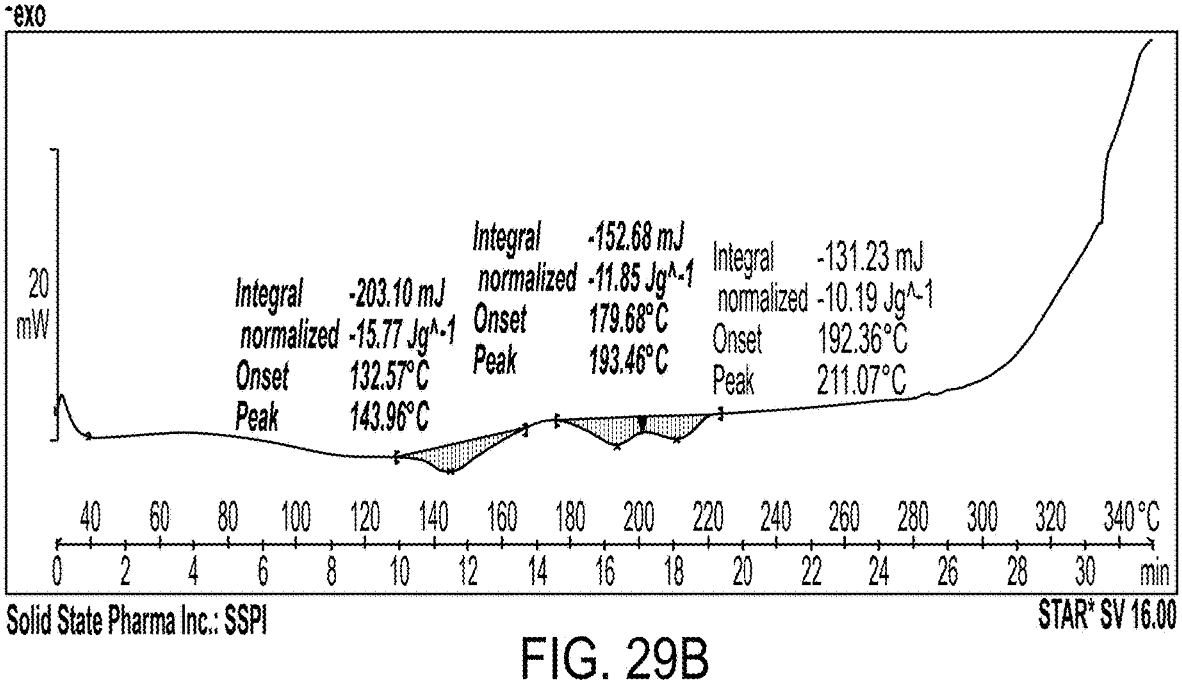
FIG. 29*b* shows the DSC thermogram of Compound A•2MSA Pattern N.

Also provided herein is the crystalline acetonitrile solvate Pattern N of 3-(4-(4-aminopiperidin-1-yl)-3-(3,5-difluorophenyl)quinolin-6-yl)-2-hydroxybenzonitrile dimesylate. Some embodiments provide a composition comprising the crystalline acetonitrile solvate Pattern N of 3-(4-(4-aminopiperidin-1-yl)-3-(3,5-difluorophenyl)quinolin-6-yl)-2-hydroxybenzonitrile dimesylate. In some embodiments, crystalline acetonitrile solvate Pattern N of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 28;

(b) an X-ray powder diffraction pattern with X-ray diffraction pattern reflections at about 5.18° 2-Theta, and about 17.21° 2-Theta;

(c) a Differential Scanning Calorimetry thermogram substantially the same as shown in FIG. 29*b;*

(d) a Differential Scanning Calorimetry thermogram with an endothermic event having an onset at about 132.6° C. and a peak at about 144.0° C.; an endothermic event having an onset at about 179.7° C. and a peak at about 193.5° C.; and an endothermic event having an onset at about 192.4° C. and a peak at about 211.1° C.;

(e) a Thermogravimetric Analysis pattern substantially the same as shown in FIG. 29*a;*

(f) a Thermogravimetric Analysis pattern with a 5.44% w/w loss from 40 to 220° C.;

(g) an unchanged XRPD after drying under dynamic vacuum at 50° C. for 2 hours; or (h) a combination thereof.

In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 28. In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 5.18° 2-Theta, and about 17.21° 2-Theta. In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 29*b*. In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with an endothermic event having an onset at about 132.6° C. and a peak at about 144.0° C.; an endothermic event having an onset at about 179.7° C. and a peak at about 193.5° C.; and an endothermic event having an onset at about 192.4° C. and a peak at about 211.1° C. In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 29*a*. In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 5.44% w/w loss from 40 to 220° C. In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate exhibits an unchanged XRPD after drying under dynamic vacuum at 50° C. for 2 hours.

In some embodiments, the crystalline acetonitrile solvate Pattern N of 3-(4-(4-aminopiperidin-1-yl)-3-(3,5-difluorophenyl)quinolin-6-yl)-2-hydroxybenzonitrile dimesylate has an X-ray diffraction pattern reflection at about 5.18° 2-Theta. In some embodiments, crystalline acetonitrile solvate Pattern N is further characterized by an X-ray diffraction pattern reflection at about 17.21° 2-Theta. In some embodiments, crystalline acetonitrile solvate Pattern N is further characterized by an X-ray diffraction pattern reflection at about 21.11° 2-Theta.

Crystalline Hydrate Pattern 0 of Compound A•2MSA

Figure 30:
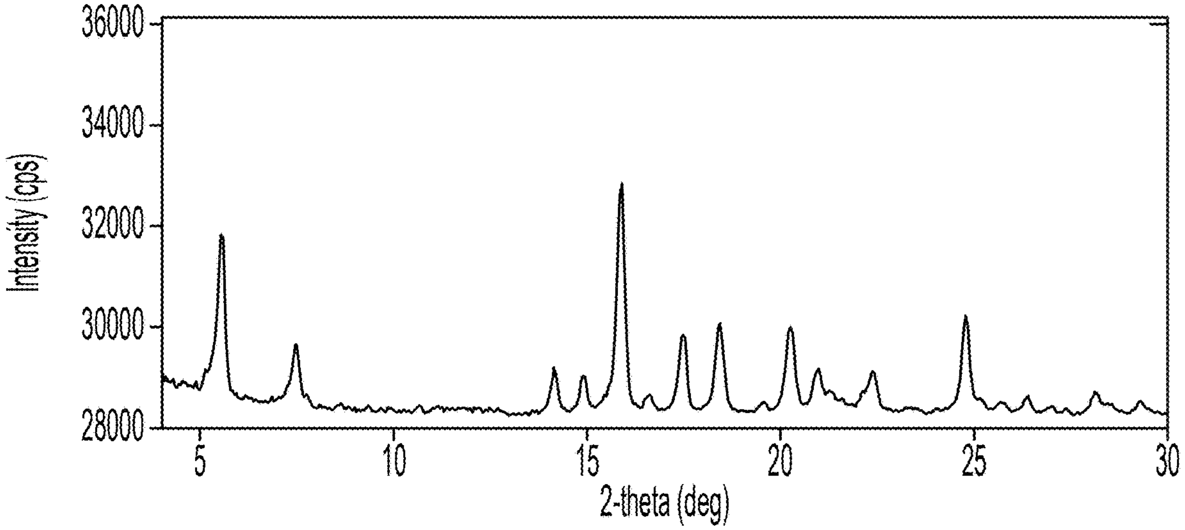
FIG. 30 shows the XRPD pattern of Compound A•2MSA Pattern 0.
Figure 31A:
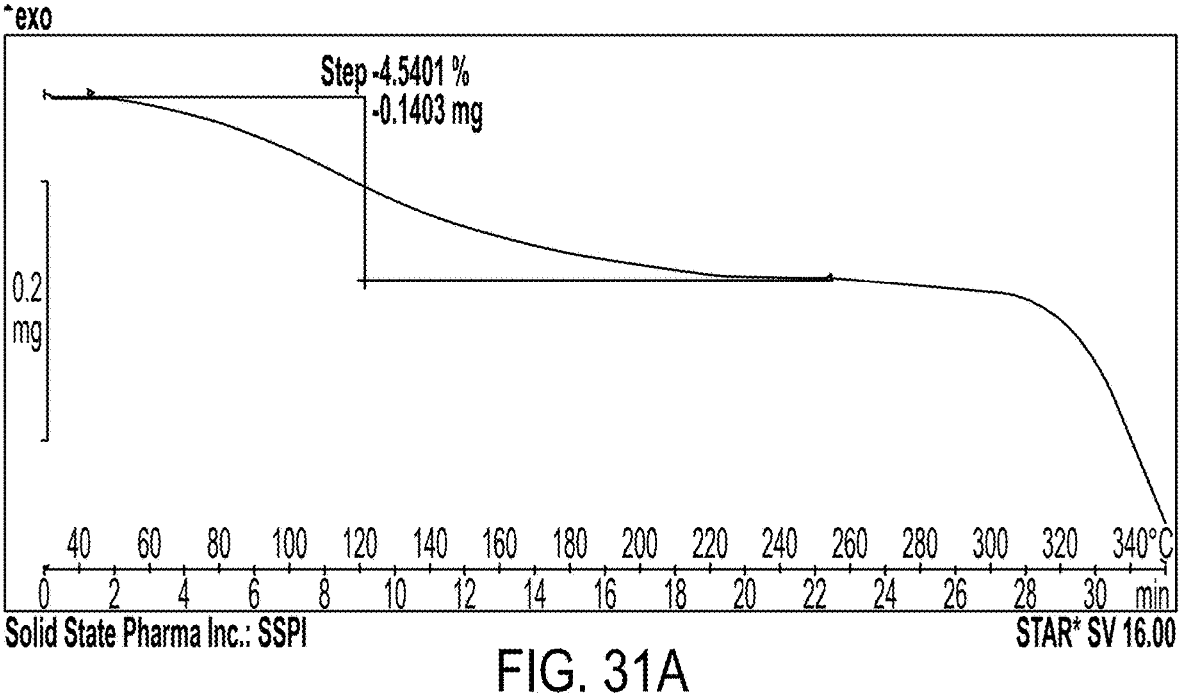
FIG. 31*a* shows the TGA pattern of Compound A•2MSA Pattern 0.
Figure 31B:
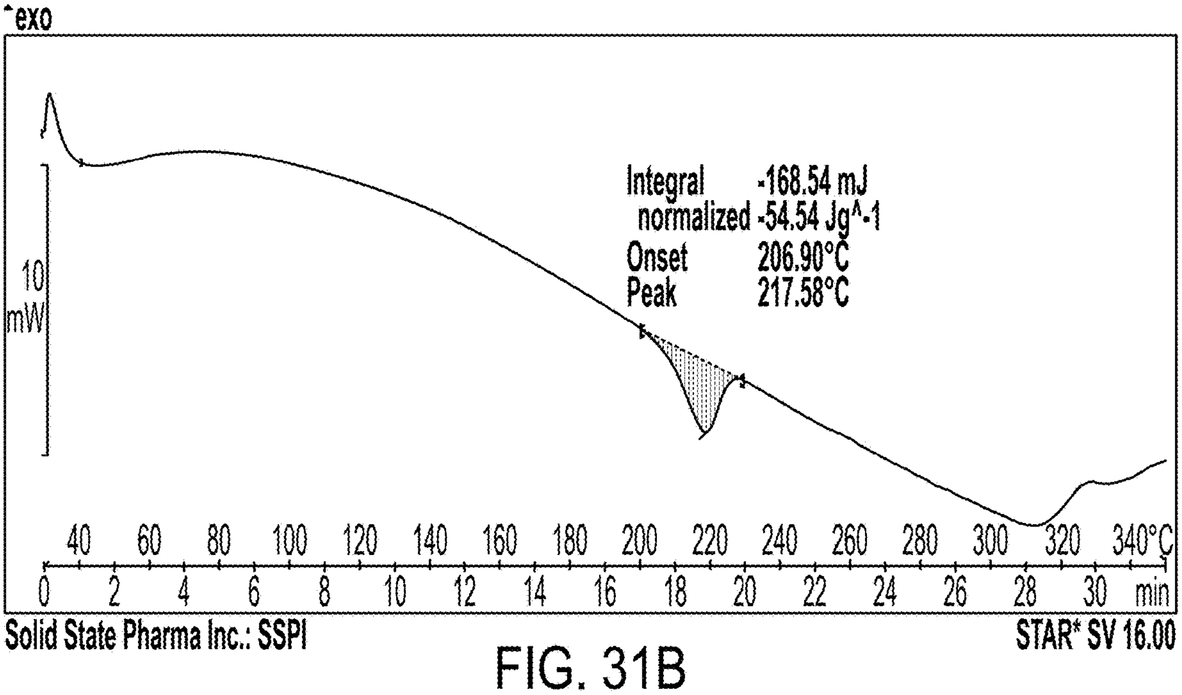
FIG. 31*b* shows the DSC thermogram of Compound A•2MSA Pattern 0.

Also provided herein is the crystalline hydrate Pattern O of 3-(4-(4-aminopiperidin-1-yl)-3-(3,5-difluorophenyl)quinolin-6-yl)-2-hydroxybenzonitrile dimesylate. Some embodiments provide a composition comprising the crystalline hydrate Pattern O of 3-(4-(4-aminopiperidin-1-yl)-3-(3,5-difluorophenyl)quinolin-6-yl)-2-hydroxybenzonitrile dimesylate. In some embodiments, crystalline hydrate Pattern O of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 30;

(b) an X-ray powder diffraction pattern with X-ray diffraction pattern reflections at about 5.56° 2-Theta, 15.87° 2-Theta, 18.43° 2-Theta, and about 24.80° 2-Theta;

(c) a Differential Scanning Calorimetry thermogram substantially the same as shown in FIG. 31*b;*

(d) a Differential Scanning Calorimetry thermogram with an endothermic event having an onset at about 206.9° C. and a peak at about 217.6° C.;

(e) a Thermogravimetric Analysis pattern substantially the same as shown in FIG. 31*a;*

(f) a Thermogravimetric Analysis pattern with a 4.54% w/w loss from 40 to 260° C.;

(g) an unchanged XRPD after drying under dynamic vacuum at 50° C. for 2 hours; or (h) a combination thereof.

In some embodiments, the crystalline hydrate Pattern O of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 30. In some embodiments, the crystalline hydrate Pattern O of 3-(4-(4-aminopiperidin-1-yl)-3-(3,5- difluorophenyl)quinolin-6-yl)-2-hydroxybenzonitrile dimesylate exhibits an X-ray powder diffraction pattern with X-ray diffraction pattern reflections at about 5.56° 2-Theta, 15.87° 2-Theta, 18.43° 2-Theta, and about 24.80° 2-Theta. In some embodiments, the crystalline hydrate Pattern O of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram substantially the same as shown in FIG. 31*b*. In some embodiments, the crystalline hydrate Pattern O of 3-(4-(4-aminopiperidin-1-yl)-3-(3,5-difluorophenyl)quinolin-6-yl)-2-hydroxybenzonitrile dimesylate exhibits a Differential Scanning Calorimetry thermogram with an endothermic event having an onset at about 206.9° C. and a peak at about 217.6° C. In some embodiments, the crystalline hydrate Pattern O of 3-(4-(4-aminopiperidin-1-yl)-3-(3,5-difluorophenyl)quinolin-6-yl)-2-hydroxybenzonitrile dimesylate exhibits a Thermogravimetric Analysis pattern substantially the same as shown in FIG. 31*a*. In some embodiments, the crystalline hydrate Pattern O of 3-(4-(4-aminopiperidin-1-yl)-3-(3,5-difluorophenyl)quinolin-6-yl)-2-hydroxybenzonitrile dimesylate exhibits a Thermogravimetric Analysis pattern with a 4.54% w/w loss from 40 to 260° C. In some embodiments, the crystalline hydrate Pattern O of 3-(4-(4-aminopiperidin-1-yl)-3-(3,5-difluorophenyl)quinolin-6-yl)-2-hydroxybenzonitrile dimesylate exhibits an unchanged XRPD after drying under dynamic vacuum at 50° C. for 2 hours.

In some embodiments, the crystalline hydrate Pattern O of 3-(4-(4-aminopiperidin-1-yl)-3-(3,5-difluorophenyl)quinolin-6-yl)-2-hydroxybenzonitrile dimesylate has an X-ray diffraction pattern reflection at about 15.87° 2-Theta. In some embodiments, crystalline hydrate Pattern 0 is further characterized by X-ray diffraction pattern reflections at about 5.56° 2-Theta, 18.43° 2-Theta, and about 24.80° 2-Theta. In some embodiments, crystalline hydrate Pattern 0 is further characterized by an X-ray diffraction pattern reflection at about 7.43° 2-Theta, about 17.50° 2-Theta, about 20.22° 2-Theta, about 20.96° 2-Theta, and about 22.38° 2-Theta.

Crystalline Pattern P of Compound A•2MSA

Figure 32:
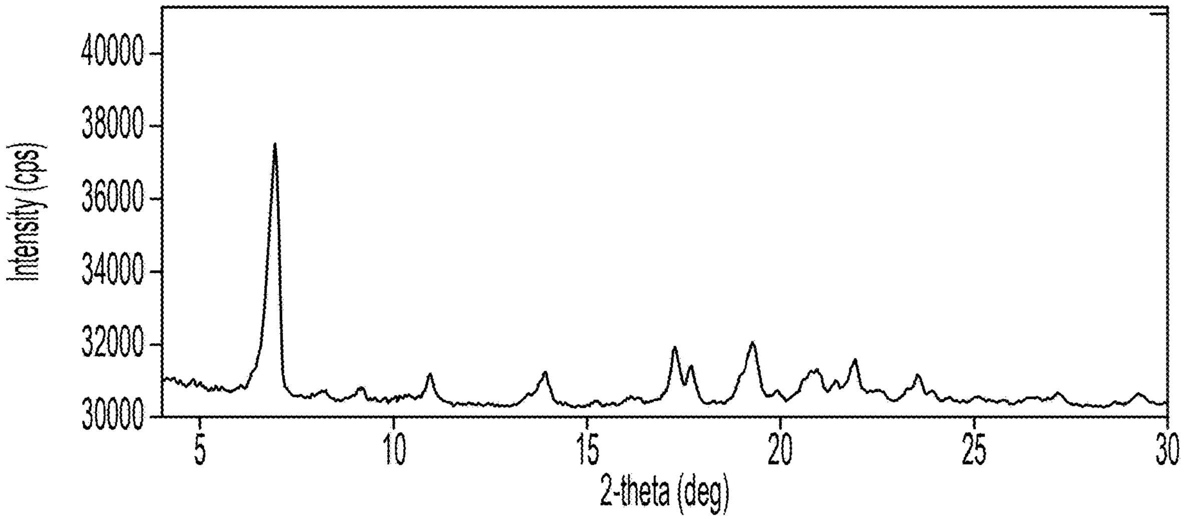
FIG. 32 shows the XRPD pattern of Compound A•2MSA Pattern P.

Also provided herein is the crystalline Pattern P of 3-(4-(4-aminopiperidin-1-yl)-3-(3,5-difluorophenyl)quinolin-6-yl)-2-hydroxybenzonitrile dimesylate. Some embodiments provide a composition comprising the crystalline Pattern P of 3-(4-(4-aminopiperidin-1-yl)-3-(3,5-difluorophenyl)quinolin-6-yl)-2-hydroxybenzonitrile dimesylate. In some embodiments, crystalline Pattern P of 3-(4-(4-aminopiperidin-1-yl)-3-(3,5-difluorophenyl)quinolin-6-yl)-2-hydroxybenzonitrile dimesylate is characterized as having:

(a) an X-ray powder diffraction pattern substantially the same as shown in FIG. 32;
(b) an X-ray powder diffraction pattern with X-ray diffraction pattern reflections at about 6.97° 2-Theta, about 17.26° 2-Theta, about 19.33° 2-Theta, and about 20.94° 2-Theta;
(c) an unchanged XRPD after drying under dynamic vacuum at 50° C. for 2 hours; an XRPD that converts to Pattern B on storage at 96% RH and 25° C. for 3 days; or
(d) a combination thereof.

In some embodiments, the crystalline Pattern P of 3-(4-(4-aminopiperidin-1-yl)-3-(3,5-difluorophenyl)quinolin-6-yl)-2-hydroxybenzonitrile dimesylate exhibits an X-ray powder diffraction pattern substantially the same as shown in FIG. 32. In some embodiments, the crystalline Pattern P of 3-(4-(4-aminopiperidin-1-yl)-3-(3,5-difluorophenyl)quinolin-6-yl)-2-hydroxybenzonitrile dimesylate exhibits an X-ray powder diffraction pattern with X-ray diffraction pattern reflections at about 6.97° 2-Theta, about 17.26° 2-Theta, about 19.33° 2-Theta, and about 20.94° 2-Theta. In some embodiments, the crystalline Pattern P of 3-(4-(4-aminopiperidin-1-yl)-3-(3,5-difluorophenyl)quinolin-6-yl)-2-hydroxybenzonitrile dimesylate exhibits an unchanged XRPD after drying under dynamic vacuum at 50° C. for 2 hours. In some embodiments, the crystalline Pattern P of 3-(4-(4-aminopiperidin-1-yl)-3-(3,5-difluorophenyl)quinolin-6-yl)-2-hydroxybenzonitrile dimesylate exhibits an XRPD that converts to Pattern B on storage at 96% RH and 25° C. for 3 days.

In some embodiments, the crystalline Pattern P of 3-(4-(4-aminopiperidin-1-yl)-3-(3,5-difluorophenyl)quinolin-6-yl)-2-hydroxybenzonitrile dimesylate has an X-ray diffraction pattern reflection at about 6.97° 2-Theta. In some embodiments, crystalline Pattern P is further characterized by X-ray diffraction pattern reflections at about 17.26° 2-Theta, about 19.33° 2-Theta, and about 20.94° 2-Theta. In some embodiments, crystalline Pattern P is further characterized by an X-ray diffraction pattern reflection at about 10.97° 2-Theta, about 13.88° 2-Theta, about 17.67° 2-Theta, about 21.94° 2-Theta, and about 29.32° 2-Theta.

Synthesis of Compound A•2MSA

Compounds described herein are synthesized using standard synthetic techniques or using methods known in the art in combination with methods described herein. Unless otherwise indicated, conventional methods of mass spectroscopy, NMR, HPLC are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In the reactions described, it may be necessary to protect reactive functional groups, for example hydroxy or amino groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure).

Disclosed herein are methods for the preparation of Compound A•2MSA, as outlined in Scheme A.

Scheme A

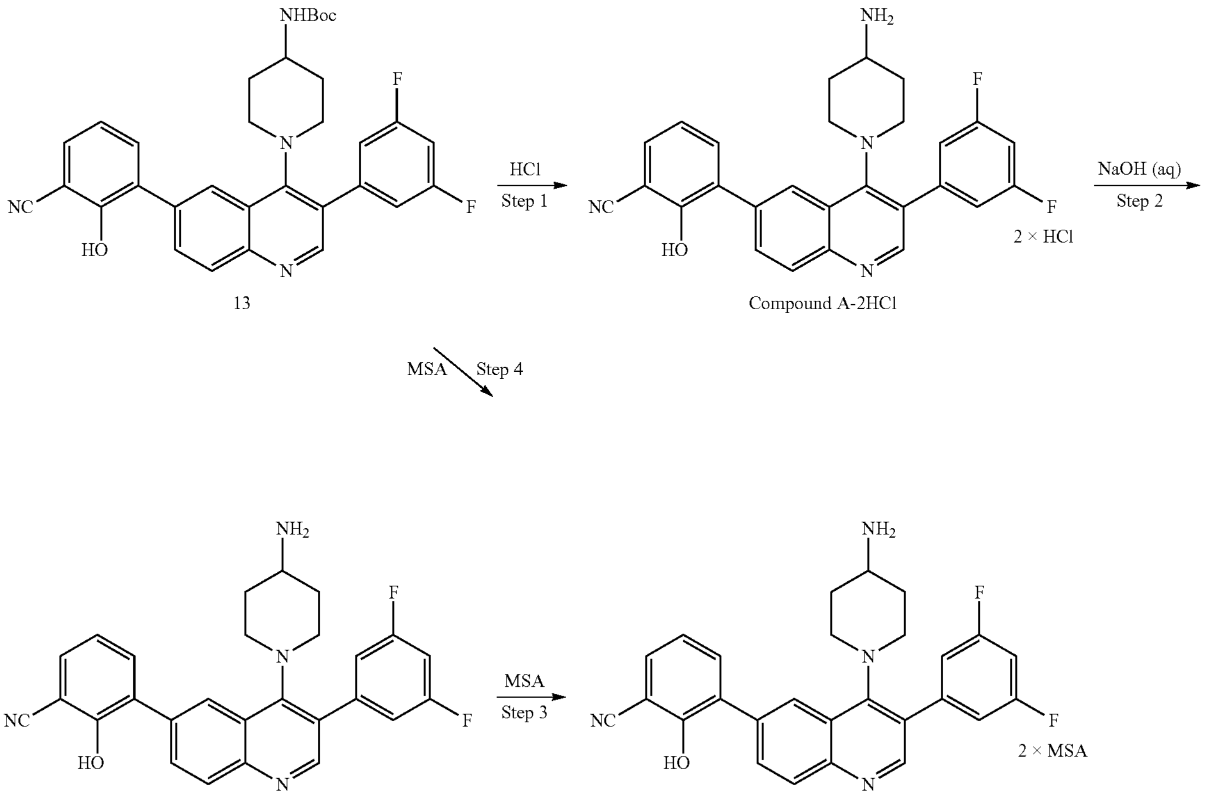

13

Compound A-2HCl

Compound A

Compound A-2MSA

Briefly, in some embodiments, deprotection of the Boc group of compound 13 and treatment with HCl yields Compound A•2HC1. In some embodiments, Compound A•2HC1 is treated with an appropriate base, such as sodium hydroxide, in order to yield Compound A (free base). In some embodiments, Compound A (free base) is then treated with methanesulfonic acid (MSA) to yield Compound A•2MSA. In alternative embodiments, compound 13 treated with MSA to directly yield Compound A•2MSA.

In some embodiments, compound 13 is synthesized as previously disclosed in U.S. Pat. No. 9,896,432, and in U.S. patent application Ser. No. 16/249,729. Briefly, compound 13 is synthesized from compound 11 by two successive Suzuki reactions: first with boronic acid 7 or trifluoroborate 5; then with 3,5-difluorophenylboronic acid. In some embodiments, compound 12 is isolated before the second Suzuki reaction. In some embodiments, compound 12 is not isolated between the two Suzuki reactions. In some embodiments, the two Suzuki reactions are performed in a single reaction vessel. In some embodiments, the two Suzuki reactions are performed with the same catalyst system. In some embodiments, the two Suzuki reactions are performed in a single reaction vessel and with the same catalyst system. In some embodiments, the two Suzuki reactions are performed in a single reaction vessel and with the same catalyst system without additional catalyst being added between the Suzuki reactions.

Scheme B

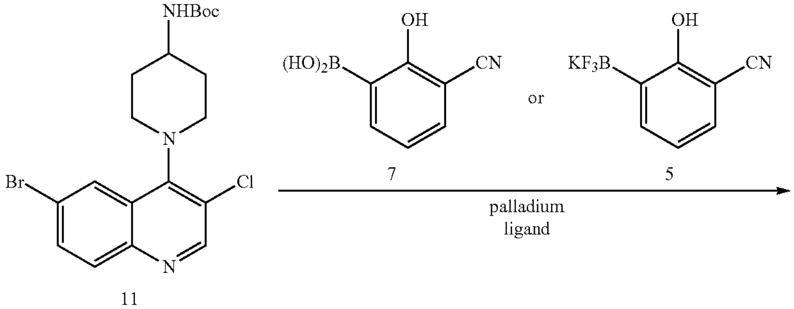

or

7

5

11

-continued

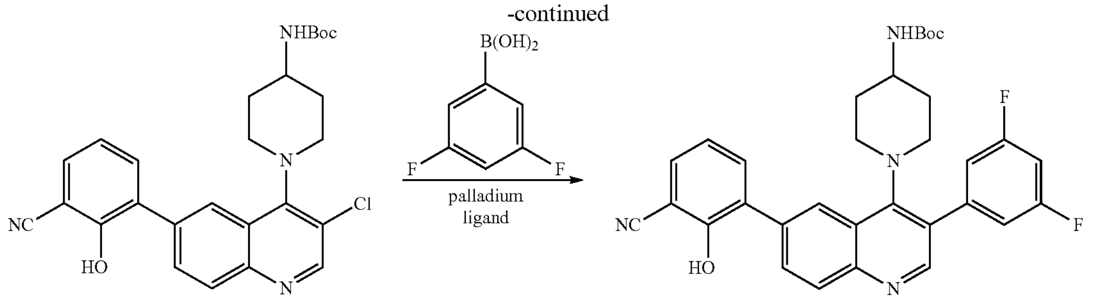

12 13

In some embodiments, residual Palladium is removed from compound 13 via a palladium scavenger, such as $SiO_2$, charcoal, L-cysteine, N-acetyl-L-cysteine, SilicaBond Cysteine, Si-Thiol, SilicaBond DMT, or the like.

In some embodiments, compound 13 contains a detectable amount of unreacted starting materials. In some embodiments, a sample of compound 13 contains a detectable amount of an impurity selected from:

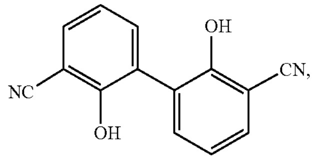

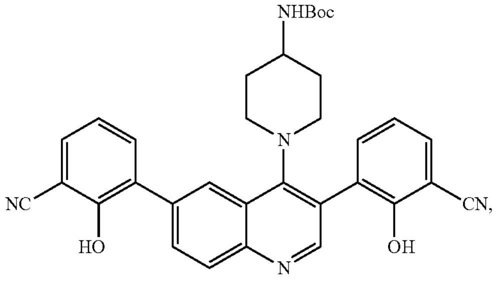

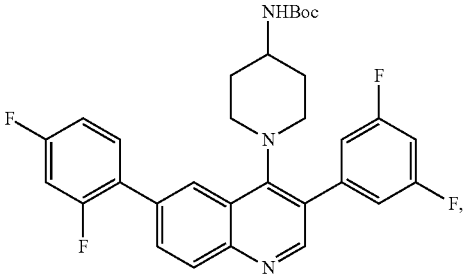

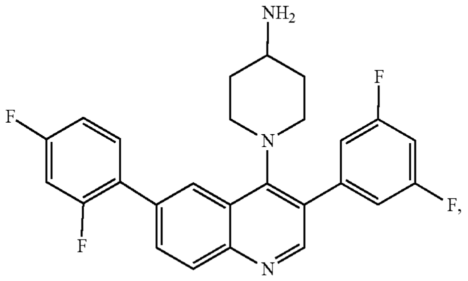

-continued

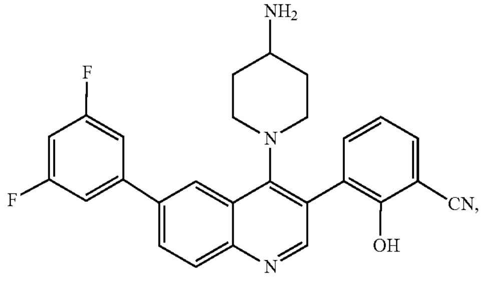

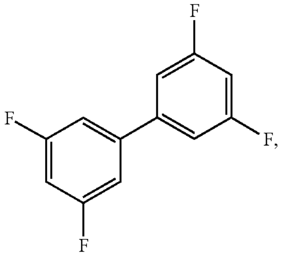

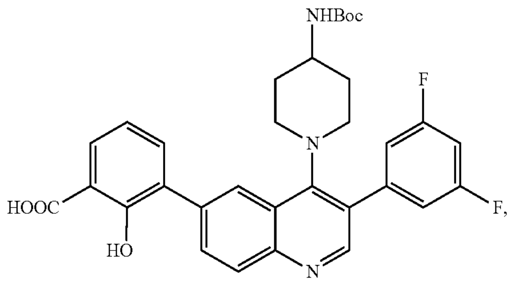

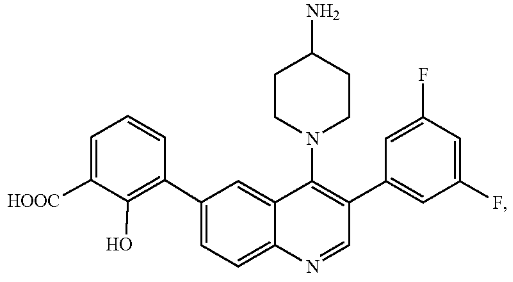

-continued
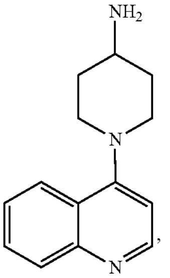
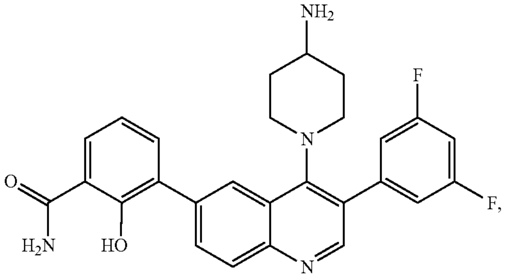
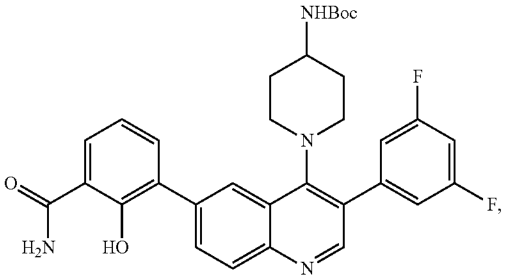
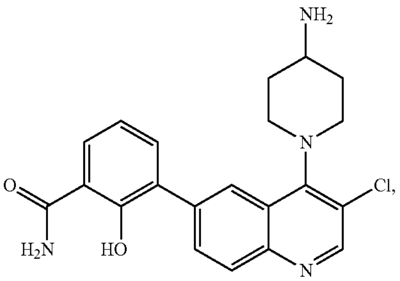
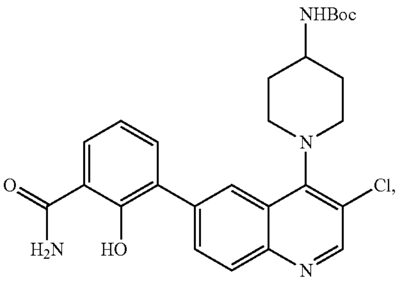
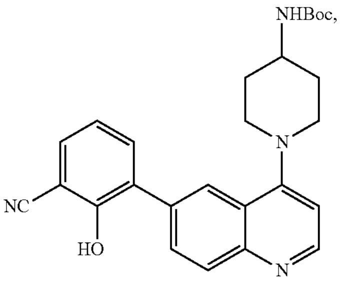
-continued
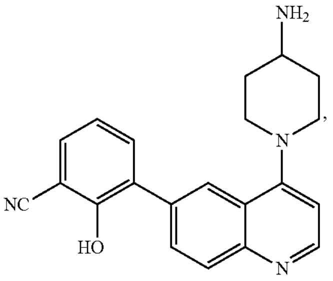
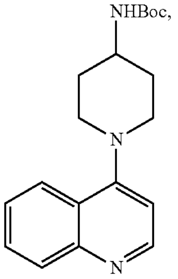
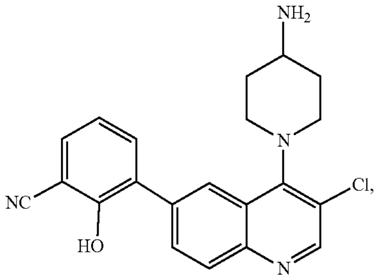
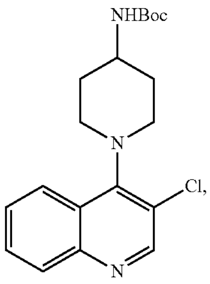
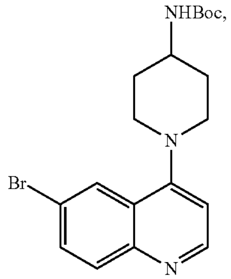
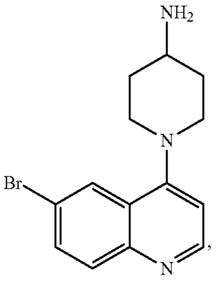

-continued

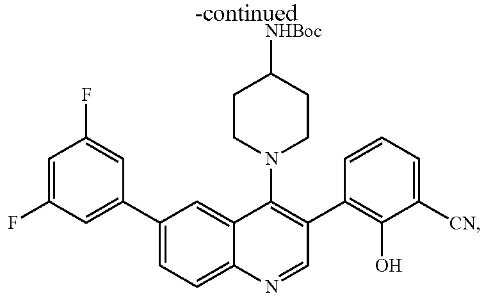

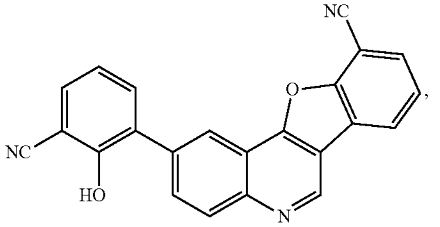

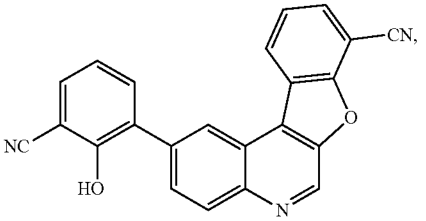

and

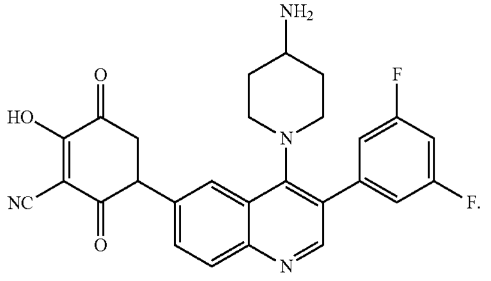

In some embodiments, samples of Compound A, or a pharmaceutically acceptable salt thereof (i.e., Compound A•2MSA), are substantially free of structurally related impurities. Structurally related impurities include, but are not limited to, those compounds that are used at any step of the synthesis of Compound A, or a pharmaceutically acceptable salt thereof (i.e., Compound A•2MSA), as well as those compounds described in the preceding paragraph.

In some embodiments, compound 13 is purified by recrystallization. In some embodiments, compound 13 is heated in a suitable solvent or solvent mixture for an appropriate amount of time. In some embodiments, the purity of compound 13 is improved by this process. In some embodiments, this process of recrystallization/slurrying removes or reduces the amount of residual palladium in samples of Compound 13.

Purification steps are performed to reduce the amount of palladium in the product. Purification steps to reduce the amount of palladium in a product are conducted so that active pharmaceutical ingredients meet palladium specification guidelines. ("Guideline on the Specification Limits for Residues of Metal Catalysts" European Medicines Agency *Pre-authorisation Evaluation of Medicines for Human Use*, London, January 2007, Doc. Ref. CPMP/SWP/QWP/4446/00 corr.). In some embodiments, purification steps to reduce the amount of palladium in a product includes, but is not limited to, treatment with solid trimercaptotriazine (TMT), polystyrene-bound TMT, mercapto-porous polystyrene-bound TMT, polystyrene-bound ethylenediamine, activated carbon, glass bead sponges, Smopex™, silica bound scavengers, thiol-derivatized silica gel, N-acetyl-L-cysteine, n-$Bu_3P$, crystallization, extraction, L-cysteine, n-$Bu_3P$/lactic acid (Garrett et al., Adv. Synth. Catal. 2004, 346, 889-900). In some embodiments, activated carbon includes but is not limited to DARCO® KB-G, DARCO® KB-WJ. In one aspect silica bound scavengers include but are not limited to

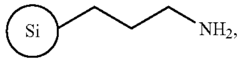

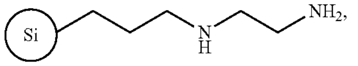

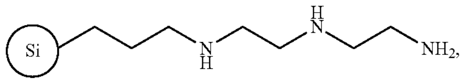

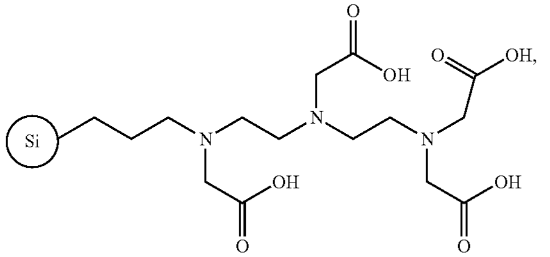

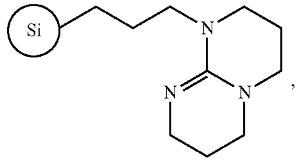

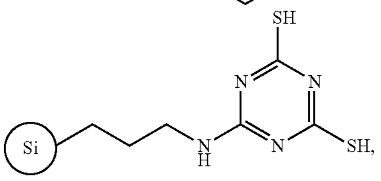

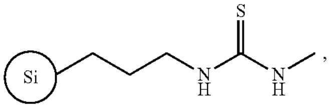

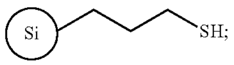

where

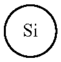

denotes silica gel. In some embodiments, the purification steps to reduce the amount of palladium include the use of activated carbon, derivatized silica gel (e.g., thiol derivatized silica gel), or combinations thereof.

In some embodiments, 13 is further treated with a metal scavenger to remove residual palladium. In some embodiments, the metal scavenger comprises $SiO_2$, charcoal, aqueous solution of L-cysteine, N-acetyl-L-cysteine, a Silicycle metal scavenger, Si-thiol, SiliaBond DMT or SiliaBond Cysteine. In some embodiments, the scavenger loading (w/w) is 1:3, 1:2, or 1:1. In some embodiments, the metal scavenger is Si-thiol.

In some embodiments, crude 13 as isolated from the reaction is treated with a metal scavenger. In some other embodiments, recrystallized 13 is treated with a metal scavenger. In some of these embodiments, palladium levels are reduced sufficiently to be undetectable.

In some embodiments, the presence of residual heavy metal (e.g. palladium) impurities is determined by utilizing methods known in the art. In some embodiments, the presence of residual heavy metal (e.g. palladium) impurities is determined by the use of inductively coupled plasma mass spectrometry (ICP-MS). In some embodiments, the presence of residual heavy metal (e.g. palladium) impurities is determined by the use of techniques described in U.S. Pharmacopeia General Chapter <231> Heavy Metals.

Preparation of Compound A•2HC1 from Compound 13

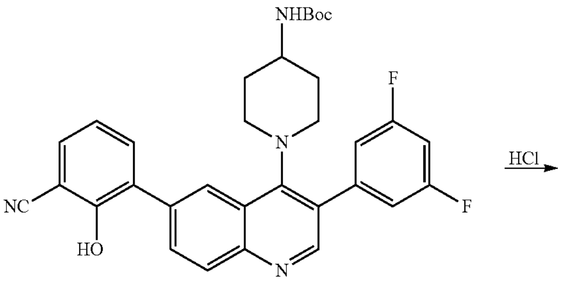

13

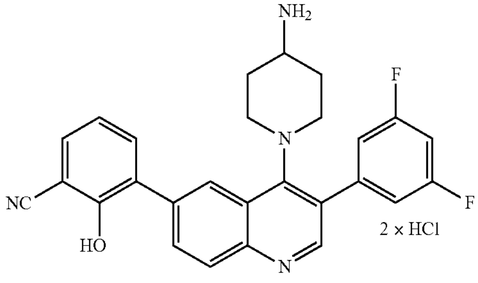

Compound A-2HCl

In some embodiments, 13 is treated with hydrochloric acid in a suitable solvent to yield Compound A•2HC1. In some embodiments, the suitable solvent is isopropyl alcohol (IPA), methyl tert-butyl ether (MTBE), toluene, ethyl acetate, isopropyl acetate, water, or mixtures thereof. In some embodiments, the suitable solvent is isopropyl alcohol, ethyl acetate, or isopropyl acetate. In some embodiments, the suitable solvent is IPA. In some embodiments, the suitable solvent is isopropyl acetate.

Preparation of Compound A (free base) from Compound A•2HC1

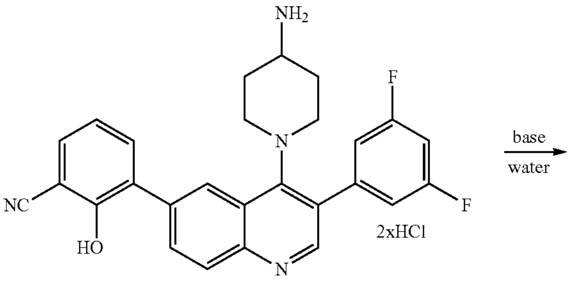

Compound A-2HCl

-continued

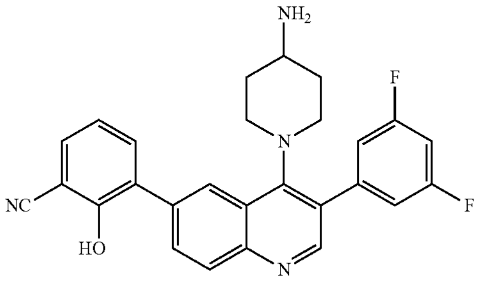

Compound A

In some embodiments, the free base of Compound A is made by treating Compound A•2HC1 with a suitable base in a suitable solvent. In some embodiments, the suitable base is sodium hydroxide, sodium bicarbonate, or the like. In some embodiments, the suitable base is sodium hydroxide. In some embodiments, the suitable solvent is water. In some embodiments, the solid is filtered from the mixture to isolate the free base of Compound A.

Preparation of Compound A-2MSA from Compound A (free base)

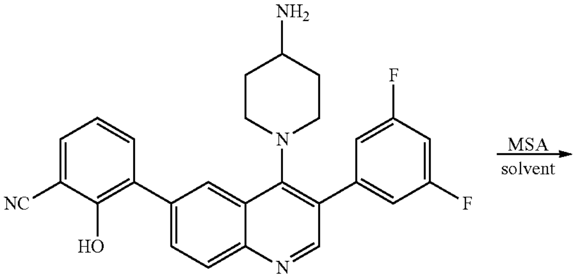

Compound A

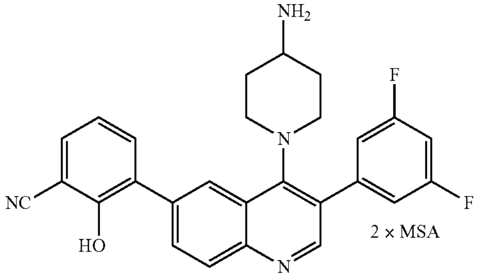

Compound A-2MSA

In some embodiments, Compound A•2MSA is generated by treating the free base with methanesulfonic acid in a suitable solvent. In some embodiments, the suitable solvent is methanol, ethanol, isopropyl alcohol, acetone, methyl acetate, ethyl acetate, isopropyl acetate, tetrahydrofuran, tetrahydropyran, water, or combinations thereof. In some embodiments, the suitable solvent is a mixture of acetone and water. In some embodiments, Compound A•2MSA is isolated by filtering the solids from the reaction mixture. In some embodiments, the isolated Compound A•2MSA exhibits an XRPD pattern consistent with Pattern B.

Preparation of Compound A•2MSA directly from Compound 13

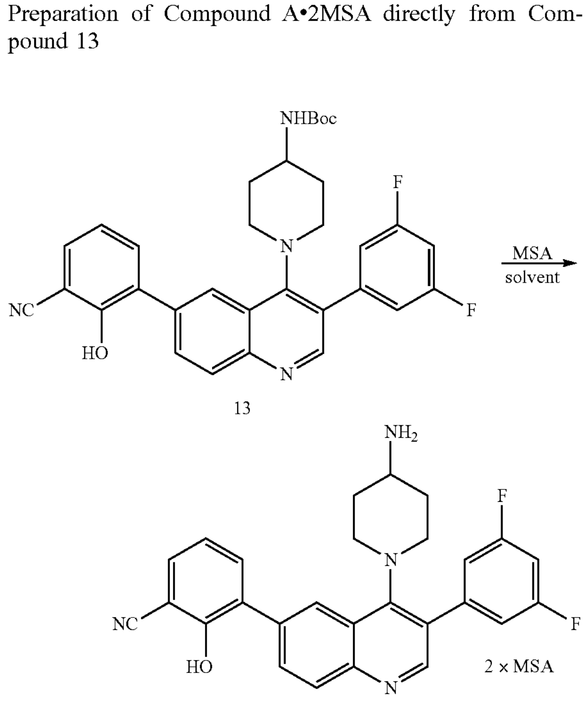

13

Compound A-2MSA

In some embodiments, Compound A•2MSA is formed directly from 13. In some embodiments, 13 is treated with methanesulfonic acid in a suitable solvent to yield Compound A•2MSA. In some embodiments, the suitable solvent is isopropyl alcohol (IPA), methyl tert-butyl ether (MTBE), tetrahydrofuran, toluene, ethyl acetate, methyl acetate, isopropyl acetate, acetone, N-methyl-2-pyrrolidone (NMP), water, or mixtures thereof. In some embodiments, the suitable solvent is a mixture of acetone and water. In some embodiments, the suitable solvent is NMP. In some embodiments, the isolated Compound A•2MSA exhibits an XRPD pattern consistent with Pattern B. In some embodiments, the isolated Compound A•2MSA is stored in a humid environment to form Compound A•2MSA that exhibits an XRPD pattern consistent with Pattern B.

Preparations of Compound A•2MSA

In one aspect, disclosed herein is a method of making 3-(4-(4-aminopiperidin-1-yl)-3-(3,5-difluorophenyl)quinolin-6-yl)-2-hydroxybenzonitrile dimesylate, or solvate thereof, comprising the steps of: (i) reacting tert-butyl (1-(6-(3-cyano-2-hydroxyphenyl)-3-(3,5-difluorophenyl)quinolin-4-yl)piperidin-4-yl)carbamate with hydrochloric acid in a suitable solvent; (ii) optionally, adding additional solvent to the reaction mixture of step (i), and purging the reaction mixture with argon or nitrogen gas to remove excess hydrochloric acid; (iii) filtering the slurry of step (ii) to provide 3-[4-(4-amino-piperidin-1-yl)-3-(3,5-difluoro-phenyl)-quinolin-6-yl]-2-hydroxy-benzonitrile dihydrochloride; (iv) adding a suitable amount of water to the solid of step (iii); (v) adding ammonium hydroxide solution, sodium bicarbonate solution, or sodium hydroxide solution to the slurry of step (iv) to achieve a pH of about 9-10; (vi) filtering the slurry of step (vi) to provide 3-[4-(4-amino-piperidin-1-yl)-3-(3,5-difluoro-phenyl)-quinolin-6-yl]-2-hydroxy-benzonitrile (free base); (vii) contacting the solid of step (vi) with methanesulfonic acid in a suitable solvent at a suitable temperature; and (viii) cooling the suspension of step (vii) and filtering the solids to provide 3-[4-(4-amino-piperidin-1-yl)-3-(3,5-difluoro-phenyl)-quinolin-6-yl]-2-hydroxy-benzonitrile dimesylate, or a solvate thereof. In some embodiments, the suitable solvent in step (i) is the suitable solvent is isopropyl alcohol (IPA), methyl tert-butyl ether (MTBE), toluene, ethyl acetate, isopropyl acetate, water, or a combination thereof the additional solvent in step (ii) is isopropyl alcohol (IPA), methyl tert-butyl ether (MTBE), toluene, ethyl acetate, isopropyl acetate, water, or a combination thereof; the suitable solvent in step (vii) is methanol, ethanol, isopropyl alcohol, acetone, methyl acetate, ethyl acetate, isopropyl acetate, tetrahydrofuran, tetrahydropyran, water, or a combination thereof; or a combination thereof. In some embodiments, the suitable solvent in step (i) is isopropyl acetate, water, or a combination thereof; the additional solvent in step (ii) is isopropyl acetate; argon gas is used in step (ii); sodium hydroxide solution is used in step (v); the suitable solvent in step (vii) is acetone, water, or a mixture thereof the suitable temperature in step (vii) is about 50° C.; or a combination thereof.

In one aspect, disclosed herein is a method of making 3-(4-(4-aminopiperidin-1-yl)-3-(3,5-difluorophenyl)quinolin-6-yl)-2-hydroxybenzonitrile dimesylate, or solvate thereof, comprising the steps of: (i) reacting tert-butyl (1-(6-(3-cyano-2-hydroxyphenyl)-3-(3,5-difluorophenyl)quinolin-4-yl)piperidin-4-yl)carbamate with methanesulfonic acid in a suitable solvent at a suitable temperature; and (ii) optionally, adding additional solvent to the reaction mixture of step (i), cooling the suspension of step (i) and filtering the solids to provide 3-[4-(4-amino-piperidin-1-yl)-3-(3,5-difluoro-phenyl)-quinolin-6-yl]-2-hydroxy-benzonitrile dimesylate, or a solvate thereof. In some embodiments, the suitable solvent in step (i) is isopropyl alcohol (IPA), methyl tert-butyl ether (MTBE), tetrahydrofuran, toluene, ethyl acetate, methyl acetate, isopropyl acetate, acetone, N-methyl-2-pyrrolidone (NMP), water, or mixtures thereof the suitable temperature in step (ii) is about 40° C. to about 110° C.; the additional solvent in step (ii) is isopropyl alcohol (IPA), methyl tert-butyl ether (MTBE), tetrahydrofuran, toluene, ethyl acetate, methyl acetate, isopropyl acetate, acetone, N-methyl-2-pyrrolidone (NMP), water, or mixtures thereof or a combination thereof. In some embodiments, the suitable solvent in step (i) is acetone, water, or mixtures thereof; the suitable temperature in step (ii) is about 45° C.; the additional solvent in step (ii) acetone; or a combination thereof. In some embodiments, the suitable solvent in step (i) is N-methyl-2-pyrrolidone (NMP), water, or mixtures thereof; the suitable temperature in step (ii) is about 100° C.; no additional solvent is added in step (ii); or a combination thereof.

In one aspect, disclosed herein is a method of making 3-(4-(4-aminopiperidin-1-yl)-3-(3,5-difluorophenyl)quinolin-6-yl)-2-hydroxybenzonitrile dimesylate, or solvate thereof, comprising the steps of: (i) slurrying 3-[4-(4-amino-piperidin-1-yl)-3-(3,5-difluoro-phenyl)-quinolin-6-yl]-2-hydroxy-benzonitrile (free base) in a suitable solvent; (ii) heating the slurry of step (i) to about 50° C.; (iii) adding methanesulfonic acid to the hot slurry of step (ii); (iv) cooling the hot slurry of step (iii); and (v) filtering the solids to provide 3-[4-(4-amino-piperidin-1-yl)-3-(3,5-difluoro-phenyl)-quinolin-6-yl]-2-hydroxy-benzonitrile dimesylate, or a solvate thereof. In some embodiments, the suitable solvent of step (i) is isopropanol, acetone, water, or a mixture thereof. In some embodiments, the suitable solvent of step (i) is isopropanol. In some embodiments, the amount of isopropanol is 15 volumes. In some embodiments, the hot slurry of step (ii) is stirred for 30 minutes prior to the addition of methanesulfonic acid in step (iii). In some embodiments, the methanesulfonic acid of step (iii) is added as a solution in water. In some embodiments, the methanesulfonic acid of step (iii) is added neat and not as a solution. In some embodiments, hot slurry of step (iii) is stirred for 10 minutes to 3 hours before cooling in step (iv). In some embodiments, the hot slurry of step (iii) is stirred for 30 minutes before cooling in step (iv). In some embodiments, the slurry of step (iv) is stirred at room temperature for about 10 hours before filtering in step (v). In some embodiments, the isolated solids step (v) are washed with a suitable solvent after isolation. In some embodiments, the suitable solvent is acetone or isopropanol. In some embodiments, the suitable solvent is isopropanol. In some embodiments, the isolated solid of step (v) is vacuum dried. In some embodiments, the isolated solid of step (v) is vacuum dried at about 50° C. for about 5 h.

In some embodiments, compounds described herein are synthesized as outlined in the Examples.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound A, or a pharmaceutically acceptable salt thereof (i.e., Compound A•2MSA), comprise an organic solvent(s). In some embodiments, compositions comprising Compound A, or a pharmaceutically acceptable salt thereof (i.e., Compound A•2MSA), include a residual amount of an organic solvent(s). In some embodiments, compositions comprising Compound A, or a pharmaceutically acceptable salt thereof (i.e., Compound A•2MSA), comprise a residual amount of a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising Compound A, or a pharmaceutically acceptable salt thereof (i.e., Compound A•2MSA), include a detectable amount of an organic solvent. In some embodiments, the pharmaceutically acceptable salt of Compound A is an MSA salt (i.e., Compound A•2MSA). In some embodiments, the organic solvent is a Class 3 solvent.

In other embodiments are compositions comprising Compound A, or a pharmaceutically acceptable salt thereof (i.e., Compound A•2MSA), wherein the composition comprises a detectable amount of solvent that is less than about 1%, wherein the solvent is selected from acetone, 1,2-dimethoxyethane, acetonitrile, ethyl acetate, tetrahydrofuran, methanol, ethanol, heptane, and 2-propanol. In a further embodiment are compositions comprising Compound A, or a pharmaceutically acceptable salt thereof (i.e., Compound A•2MSA), wherein the composition comprises a detectable amount of solvent which is less than about 5000 ppm. In yet a further embodiment are compositions comprising Compound A, or a pharmaceutically acceptable salt thereof (i.e., Compound A•2MSA), wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

In some embodiments, Compound A, or a pharmaceutically acceptable salt thereof (i.e., Compound A•2MSA), is free of impurities. In some embodiments, Compound A, or a pharmaceutically acceptable salt thereof (i.e., Compound A•2MSA), is free of structurally related impurities. In some embodiments, Compound A, or a pharmaceutically acceptable salt thereof (i.e., Compound A•2MSA), is essentially free of impurities. In some embodiments, Compound A, or a pharmaceutically acceptable salt thereof (i.e., Compound A•2MSA), is essentially free of structurally related impurities. In some embodiments, the amount of impurities is less than 1% (w/w). In some embodiments, the amount of impurities is less than 0.5% (w/w). In some embodiments, the amount of impurities is less than 0.4% (w/w). In some embodiments, the amount of impurities is less than 0.3% (w/w). In some embodiments, the amount of impurities is less than 0.25% (w/w). In some embodiments, the amount of impurities is less than 0.20% (w/w). In some embodiments, the amount of impurities is less than 0.15% (w/w). In some embodiments, the amount of impurities is less than 0.10% (w/w). In some embodiments, the amount of impurities is less than 0.08% (w/w). In some embodiments, the amount of impurities is less than 0.05% (w/w). In some embodiments, the amount of impurities is not detectable.

In some embodiments, Compound A, or a pharmaceutically acceptable salt thereof (i.e., Compound A•2MSA), is substantially free of impurities. In some embodiments, Compound A, or a pharmaceutically acceptable salt thereof (i.e., Compound A•2MSA), is substantially free of structurally related impurities. In some embodiments, substantially free means less than about 5% (w/w), less than about 3% (w/w), less than about 1% (w/w), less than about 0.5% (w/w), or less than about 0.2% (w/w). In some embodiments, substantially free means less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.10% (w/w), less than about 0.08% (w/w), or less than about 0.05% (w/w). In some embodiments, substantially free means an undetectable amount.

The methods and formulations described herein include the use of N-oxides (if appropriate), or pharmaceutically acceptable salts of compounds having the structure disclosed herein, as well as active metabolites of these compounds having the same type of activity.

In some embodiments, sites on the organic radicals (e.g. alkyl groups, aromatic rings) of compounds disclosed herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or altered metabolic pathways to reduce undesirable metabolites or reduced dosage requirements.

In some embodiments, one or more hydrogen atoms on Compound A are replaced with deuterium. In some embodiments, substitution with deuterium affords certain therapeutic advantages resulting from greater metabolic stability, such as, for example, increased in vivo half-life or reduced dosage requirements.

In one aspect, described is a methanesulfonic acid salt of a compound with the following structure:

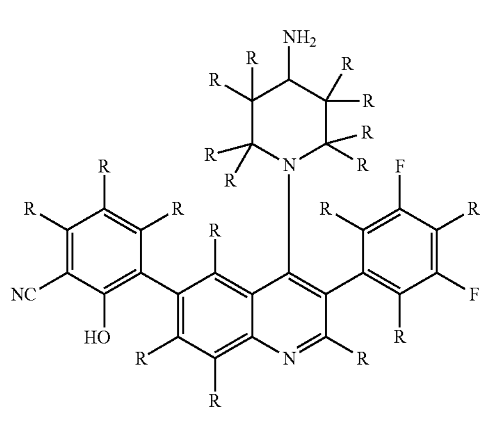

wherein, each R is independently selected from hydrogen or deuterium.

In some embodiments, the methanesulfonic salt is a dimethanesulfonic acid salt.

In some embodiments, the compounds disclosed herein possess one or more stereocenters and each stereocenter exists independently in either the R or S configuration. For example, in some embodiments, the compound disclosed herein exists in the R configuration when one stereocenter is present. In other embodiments, the compound disclosed herein exists in the S configuration when one stereocenter is present. In some embodiments, the compound disclosed herein exists in the RR configuration when two stereocenters are present. In some embodiments, the compound disclosed herein exists in the RS configuration when two stereocenters are present. In some embodiments, the compound disclosed herein exists in the SS configuration when two stereocenters are present. In some embodiments, the compound disclosed herein exists in the SR configuration when two stereocenters are present.

The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds disclosed herein are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers of compounds disclosed herein is carried out using covalent diastereomeric derivatives of the compounds described herein. In another embodiment, diastereomers of compounds disclosed herein are separated by separation/resolution techniques based upon differences in solubility. In other embodiments, separation of stereoisomers of compounds disclosed herein is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

Separation of individual enantiomers from a racemic mixture is possible by the use of chiral supercritical fluid chromatography (SFC) or chiral high performance liquid chromatography (HPLC). In some embodiments, enantiomers described herein are separated from each other by the use of chiral SFC or chiral HPLC. In some embodiments, compounds disclosed herein that include one or more chiral centers (e.g. compounds disclosed herein that include the moiety trans-octahydro-1H-pyrido[3,4-b]morpholin-6-yl) are separated into individual enantiomers using chiral SFC or chiral HPLC. A wide variety of conditions and suitable columns are available.

Daicel polysaccharide chiral stationary phases (CSPs) are among the columns used for chiral SFC separations. In some embodiments, Daicel analytical immobilised and coated CHIRALPAK and CHIRALCEL HPLC columns can be used for SFC analysis.

In some embodiments, screening for the suitability of using a SFC column is performed on the four main immobilised phases (CHIRALPAK IA, IB, IC and ID) and the four main coated columns (CHIRALPAK AD and AS and CHIRALCEL OD and OJ), with varying concentrations of organic modifier. A variety of column phases are available, including but not limited to OD and OJ, OX and OZ chlorinated phases, and a range of complementary cellulose based CHIRALCEL phases including OA, OB, OC, OF, OG and OK.

Non-limiting examples of chiral selectors contemplated for use in the separation of enantiomers include amylose tris (3, 5-dimethylphenylcarbamate), cellulose tris (3, 5-dimethylphenylcarbamate), cellulose tris (3, 5-dichlorophenylcarbamate), amylose tris (3-chlorophenylcarbamate), amylose tris (3, 5-dichlorophenylcarbamate), amylose tris (3-chloro, 4-methylphenylcarbamate), amylose tris ((S)-alpha-methylbenzylcarbamate), amylose tris (5-chloro-2-methylphenyl carbamate), cellulose tris (4-methylbenzoate), cellulose tris (4-chloro-3-methylphenylcarbamate), and cellulose tris (3-chloro-4-methylphenylcarbamate).

Non-limiting examples of chiral columns contemplated for use in the separation of enantiomers include CHIRALPAK IA SFC, CHIRALPAK AD-H SFC, CHIRALPAK IB SFC, CHIRALCEL OD-H SFC, CHIRALPAK IC SFC, CHIRALPAK ID SFC, CHIRALPAK IE SFC, CHIRALPAK IF SFC, CHIRALPAK AZ-H SFC, CHIRALPAK AS-H SFC, CHIRALPAK AY-H SFC, CHIRALCEL OJ-H SFC, CHIRALCEL OX-H SFC, and CHIRALCEL OZ-H SFC.

In some embodiments, the identity of and placement of substituents on the compounds described herein help to minimize undesired activity. For example, in some embodiments undesired activity includes undesired hERG inhibition. In some embodiments, the presence of a hydroxyl group and an adjacent cyano group on an aromatic ring reduces undesired hERG inhibition significantly as compared to the lack of both groups, the presence of a hydroxyl group without an adjacent cyano group, or the presence of a cyano group without an adjacent hydroxyl group. For example, in some embodiments significant reduction of undesired hERG inhibition is observed when $R^B$ is a substituted or unsubstituted 2-hydroxy-3-cyanophenyl.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "halo" or, alternatively, "halogen" or "halide" means fluoro, chloro, bromo or iodo. In some embodiments, halo is fluoro, chloro, or bromo.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound disclosed herein, or a pharmaceutically acceptable salt thereof, and a co-agent, are both administered to a patient simultaneously in the form of a single entity or dosage. The term "non-fixed combination" means that the active ingredients, e.g. a compound disclosed herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed.

(Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds disclosed herein, or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound disclosed herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound disclosed herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound disclosed herein, or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound disclosed herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

EXAMPLES

Abbreviations:
ACN: acetonitrile;
AcOH: acetic acid;
Amphos: di-tert-butyl(4-dimethylaminophenyl)phosphine;
Boc or BOC: tert-butyloxycarbonyl;
DCM: dichloromethane;
DI: deionized;
DIEA or DIPEA: diisopropylethylamine;
DMAP: 4-dimethylaminopyridine;
DMF: N,N-dimethylformamide;
DMSO: dimethyl sulfoxide;
DSC: differential scanning calorimetry;
DVS: dynamic vapour sorption;
EtOAc: ethyl acetate;
EtOH: ethanol;
equiv: equivalents, typically molar equivalents;
HPLC: high performance liquid chromatography;
hrs: hours;
h or hr: hour;
IPA: isopropylalcohol;
IPAc: isopropyl acetate;
IPC: ion pair chromatography;
KF: Karl-Fischer titration;
MeOAc: methyl acetate;
MeOH: methanol;
MIBK: methyl isobutyl ketone;
MOMCl: methoxymethyl chloride
MSA: methanesulfonic acid;
MTBE: methyl tert-butyl ether;
NCS: N-chlorosuccinimide;
NMP: N-methyl-2-pyrrolidone;
NMR: nuclear magnetic resonance;
$Pd(dppf)Cl_2$: [1,1'-bis(diphenylphosphino)ferrocene]dichloropalladium(II);
$(pinB)_2$: bis(pinacolato)diboron;
PPh: triphenylphosphine;
rt or RT: room temperature;
Rt: retention time;
SFC: supercritical fluid chromatography;
SST: somatostatin;
SSTR: somatostatin receptor;
TEA: trimethylamine;
TFA: trifluoroacetic acid;
TGA: thermogravimetric analysis;
THF: tetrahydrofuran;
TLC: thin layer chromatography;
vol: volume, typically used for reaction volume or ratio of solvents;
XRPD: x-ray powder diffraction.

The following examples are provided for illustrative purposes only and not to limit the scope of the claims provided herein.

Preparation of Compounds

Example 1: Synthesis of Potassium (3-cyano-2-hydroxyphenyl)trifluoroborate (Compound 5)

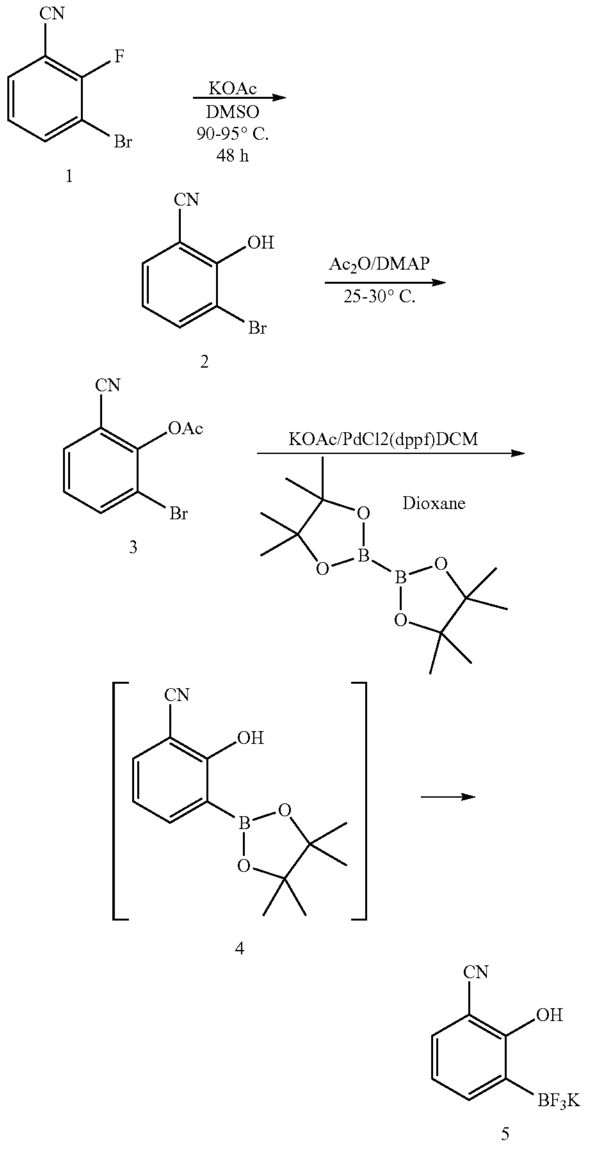

Step 1: 3-Bromo-2-fluro-benzonitrile (1, 25 g, 1.0 equiv), potassium acetate (5 equiv) was mixed in DMSO (7 vol) and heated to 90-95° C. for 48 h. IPC showed 0.38% of 1 and 96.5% of compound 2. Reaction mixture was cooled to 25-30° C. and quenched with purified water (25 vol water). Then pH was adjusted pH to 3-4 using 6N HCl solution. The obtained resulting mixture was diluted with MTBE (10 vol). The organic layer was separated, and aqueous layer was extracted with 10 vol MTBE. Combined organic layers were washed with water (10 vol×3) and concentrated to 2 vol level, chased with DCM (3 vol) and concentrated down to 2 vol again before diluted with DCM (8 vol) to afford crude solution of compound 2. This solution was used in the subsequent process without further purification.

Step 2: Crude solution of compound 2 was mixed with acetic anhydride (1.3 equiv), DMAP (0.1 equiv) at 25-30 C for 2 h with stirring. IPC showed 0.8% compound 2 and 94.8% compound 3. Reaction mass was diluted with purified water (10 vol), stirred for 30 mins. Organic layer was separated. Aqueous layer was extracted with 2 vol DCM. The combined organic layer was washed with water (8 vol×2). Charcoal (10%) was added to organic layer and stirred for 1 h before filtered through celite bed. The filtrate was then concentrated to 2 vol level, chased with 3 vol and 2 vol of n-heptane subsequently before cooled to RT and stirred for 1 hr at 5-10° C. The product was isolated via filtration as solid (25.5 g, 85% yield over two steps, HPLC purity 96.8%).

Step 3: Compound 3 (20 g, 1.0 equiv) was mixed with KOAc (3.0 equiv), bis(pinacolato)diboron (1.2 equiv) in 2-methyl-THF. The mixture was stirred and degassed with $N_2$ bubbling before addition of Pd(dppf)$Cl_2$·DCM (0.025 equiv). The resulting mixture was heated to 80-85° C. for 16 h. IPC showed 0.3% of starting material and 92% compound 4. Reaction mixture was cooled to 25-30° C. and filtered through celite pad. The celite pad was washed with MTBE (5 vol). The combined filtrate was concentrated to 2 vol and chased with MTBE to 2 vol. The resulting solution was diluted with MTBE (10 vol) and stirred for 1 h at ambient temperature. The suspension was again filtered through celite pad and the celite pad was rinsed with MTBE. The combined filtrate was washed with water (500 mL, 5 vol). The aqueous layer was extracted with MTBE. Combined organic layers were washed with 5% N-Acetyl-L-cysteine solution twice (each time 300 mL, 3 vol) and water (300 mL, 3 vol). Then the organic layer was separated, treated with 10% active charcoal, filtered through celite pad. The celite pad was rinsed with MTBE. The combined filtrate was concentrated to 2 vol level, chased with methanol twice (2×4 vol) to 3 vol, and cooled to ambient temperature before used in the next step.

Step 4: Compound 4 solution was added with $KHF_2$ (5.0 equiv), purified water (2.6 vol), and MeOH (1 vol) before heated to 65° C. for 1 h. The reaction mixture was diluted with MTBE (15 vol) before cooled to 10±5° C. The resulting suspension was stirred for 1 h before filtration. The solid was transferred to reaction flask, added with 20 vol acetone, stirred at 25±5° C. for 1 h, treated with 10% charcoal, and stirred for another 1 h. The resulting reaction mixture was then filtered through celite pad. Filtrate was concentrated to 2 vol level, chased with MTBE (3 vol×2), concentrate to 2 vol level, and diluted with MTBE (4 vol). The suspension was stirred for 1 h at 25±5° C. before filtered to afford the desired product compound 5 as off-white solid (11.5 g, 49.5%, HPLC purity 97.8%). $^1$H NMR (400 MHz, DMSO-$d_6$): δ 8.2 (s, 1H), 7.41 (m, 1H), 7.34 (m, 1H), 6.80 (m, 1H); $^{13}$C NMR (100 MHz, DMSO-$d_6$): 161.8, 138.0, 138.0, 130.8, 119.4, 118.0, 96.6.

Example 2: Synthesis of (3-cyano-2-hydroxyphenyl)boronic acid (Compound 7)

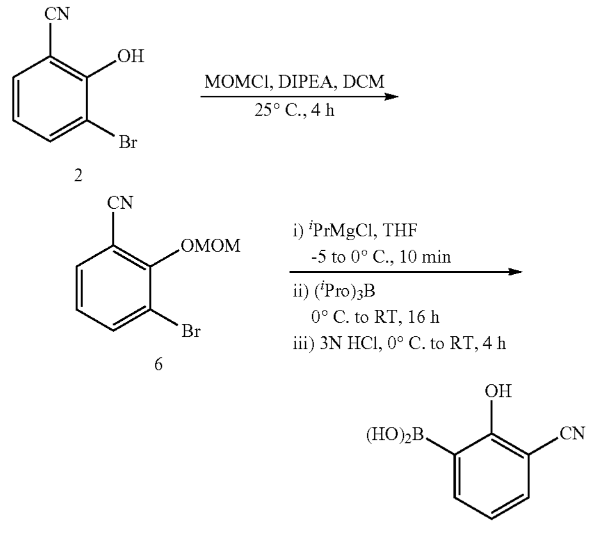

2

6

7

Step 1: Diisoproylethylamine (114 mL, 1.3 equiv) was slowly added to a solution of 3-bromo-2-hydroxybenzonitrile (Compound 2, 100 g, 1 equiv) in $CH_2Cl_2$ (1 L, 10 vol) at 0° C. and stirred for 30 min. Chloromethyl methyl ether (MOMCl) (46 mL, 1.2 equiv) was then added slowly while maintaining the internal temperature at 0 to 5° C. The reaction was then allowed to warm to RT and stirred for 4 h, until TLC showed complete reaction. The reaction was cooled to 0° C. and quenched with DI-water (300 mL, 3 vol) and the layers were separated. The aqueous layer was extracted with $CH_2Cl_2$ (300 mL, 3 vol) and the combined organic layer was washed with water and brine, concentrated on a rotavap to afford 115 g of crude product as a brown oil. The crude product was purified on a plug of $SiO_2$ and eluted with 10% ethyl acetate and pet-ether (20 vol). Only one fraction was collected, evaporated under vacuum, and dried under high vacuum to afford 86 g (70%) of compound 6 as colorless oil, which was 99.96% pure (HPLC-AUC).

Step 2: A solution of $^i$PrMgCl in THF (2 M in THF, 340 mL, 2.2 equiv) was added slowly to a solution of compound 6 (75 g, 1 equiv) in THF (1.12 L, 15 vol) while maintaining the internal temperature at −5 to 5° C. and stirred for 10 min. Triisopropyl borate (180 mL, 2.5 equiv) was then added while maintaining the internal temperature at −5 to 3° C. The reaction was then allowed to warm to room temperature and stirred for 18 h until TLC showed complete reaction. The reaction was then cooled to −10° C. and quenched by slow addition of 3N HCl (620 mL, 6 equiv) at −10° C. The mixture was stirred for 3 h at RT and extracted with ethyl acetate (525 ml, 5 vol) and the aqueous layer was extracted with ethyl acetate (225 mL, 3 vol). The combined organic layer was successively washed with DI-water (3×3 vol), brine (525 mL, 3 vol) and concentrated under vacuum to afford the crude material as a gummy solid. The crude was stirred in pet-ether (525 mL, 5 vol) for 30 min and resulting solids were filtered, washed with pet-ether (150 mL, 2 vol)

and dried under vacuum to afford 35 g (70%) of boronic acid compound 7 as an off white solid, which was 97.91% pure (HPLC-AUC).

Example 3: Synthesis of tert-Butyl (1-(6-bromo-3-chloroquinolin-4-yl)piperidin-4-yl)carbamate (11)

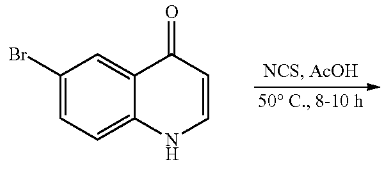

8

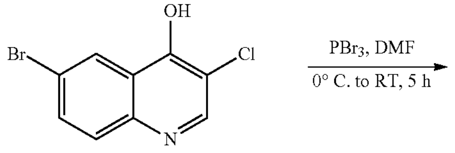

9

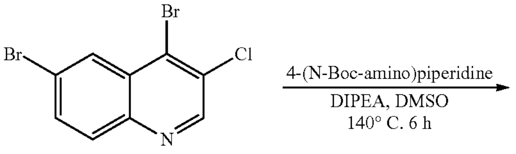

10

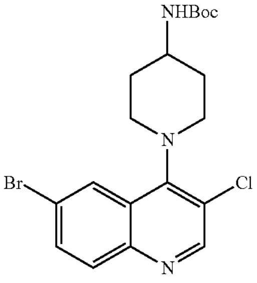

11

Step 1: N-Chlorosuccinimide (377 g, 1.05 equiv) was added to a suspension of 6-bromoquinolin-4(1H)-one (8, 600 g, 1 equiv) in acetic acid (12 L, 20 vol) at RT. The reaction was then heated to 50° C. and stirred for 8 h. The reaction was cooled to 20° C., filtered, successively washed with AcOH (1.8 L, 3 vol), water (2.4 L, 4 vol), and MTBE (1.2 L, 2 vol), and dried under vacuum on a filter to afford crude 9. The crude material was stirred in MTBE (7.2 L, 12 vol) for 2 h, filtered, washed with MTBE (0.6 L, 1 vol) and dried under vacuum to afford 541 g (78%) of 9 as an off white solid, which was determined to be 97.35% pure (HPLC-AUC).

Step 2: Phosphorus tribromide (317 mL, 1.6 equiv) was slowly added to a solution of 9 (540 g, 1 equiv) in DMF (7 L, 13 vol) at 0-5° C. The reaction was allowed to warm to RT and stirred for 4 h. The reaction was cooled to 0° C. and quenched by sat. aqueous solution of $NaHCO_3$ to pH-8 (10.8 L, 20 vol) and diluted with water (5.4 L, 10 vol). The mixture was stirred for 2 h at RT and the solids were filtered, washed with water (2.7 L, 5 vol), and dried on the filter under vacuum. The wet cake was slurried in water (5.4 L, 10 vol) for 2 h and filtered, washed with water (980 mL, 2 vol) and dried on the filter under vacuum to afford crude 10 as a solid. The crude material was stirred in MTBE (2.7 L, 5 vol) for 2 h, filtered, washed with MTBE (980 mL, 2 vol) and dried under vacuum to afford 434 g (65%) of 10 as an off white solid, which was determined to be 97.95% pure (HPLC-AUC).

Step 3: Diisopropylethylamine (932 mL, 4 equiv) and 4-(N-Boc-amino)piperidine (430 g, 1.6 equiv) were successively added to a solution of 10 (430 g, 1 equiv) in DMSO (4.3 L, 10 vol) at RT. The suspension was then heated to 140° C. and stirred for 3 h. The reaction was allowed to cool to RT, diluted with water (12.9 L, 30 vol), and stirred for 2 h. The resulting solids were filtered and dried on a filter. The wet cake was dissolved in DCM (3 L, 7 vol), and the aqueous layer was extracted with DCM (860 mL, 2 vol). The combined organic layer was washed with water (2×2.1 L, 5 vol each), brine (2.1 L, 5 vol), and dried under vacuum to afford crude 11 as a solid. The crude material was stirred in MTBE (2.21 L, 5 vol) for 1 h, filtered, washed with MTBE (860 mL, 2 vol), and dried under vacuum to afford 412 g (70%) of 11 as an off-white solid, which was determined to be 98.26% pure (HPLC-AUC).

Example 4: Alternative Synthesis of tert-Butyl (1-(6-bromo-3-chloroquinolin-4-yl)piperidin-4-yl)carbamate (11)

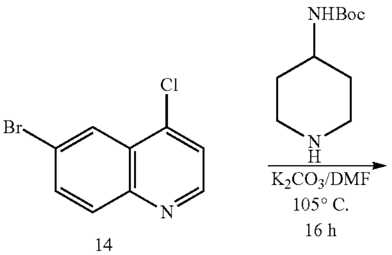

14

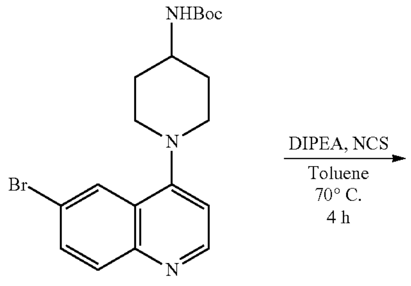

15

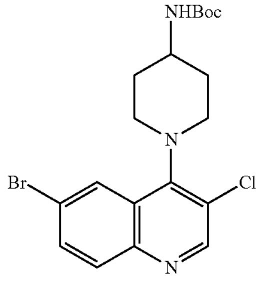

11

A mixture of 6-bromo-4-chloro-quinoline (14, 25 g, 1.0 equiv), DMF (6.0 vol.), 4-(tert-butoxy carbonylamino)piperidine (2.0 equiv), and $K_2CO_3$ (2.5 equiv) was stirred and heated to 105° C. for 16 h. Reaction was monitored by IPC-HPLC and showed 93.5% of 15 and 0.12% of 14. The reaction mixture was cooled to 25-30° C., diluted with purified water (30 vol.), and stirred for 2 h. The solid was filtered and washed with purified water. The crude solid was slurred with n-heptane (5 vol.), filtered, and washed with n-heptane (2 vol.). The solid was dried at 55° C. provided 15 (35.3 g, 84% yield). $^{1}$H NMR (400 MHz, DMSO-$d_6$): δ 8.69 (d, 1H), 8.02 (d, 1H), 7.88 (m, 1H), 7.80 (m, 1H), 7.02 (d, 1H), 6.97 (d, 1H), 3.44 (m, 3H), 2.87 (m, 2H), 1.94 (d, 2H), 1.68 (m, 2H), 1.38 (s, 9H).

Compound 15 (25 g, 1 equiv), DIPEA (0.078 equiv), NCS (1.5 equiv), and Toluene (10 vol.) were mixed and heated at 70° C. for 4 h. The reaction mixture was concentrated to 3 vol level at 45±5° C., cooled to rt, diluted with MTBE (10 vol.), and washed with purified water (10 vol.). After layer separation, the aqueous layer was extracted with MTBE (5.0 vol.). Combined organic layers were washed with purified water twice (2×5 vol.) followed by brine. The organic layer was dried over sodium sulfate, concentrated to 2 vol. level, and the aqueous layer was washed with MTBE twice (2×2 vol.). The combined organic layer was cooled and added with MTBE (1 vol.) before warmed to 50±5° C. and stirred for 1 h. The resulting suspension was cooled to 5±5° C. and stirred for 1 h. Solid was collected by filtration and washed with pre-cooled MTBE (1 vol.). The solid was taken in MTBE (2 vol.) and heated to 55±5° C. again, stirred for 1 h, cooled to 5±5° C., and stirred for another 1 h. The solid was collected by filtration and washed with pre-cooled MTBE (1 vol.). The collected solid was dried under reduced pressure at 45±5° C. for 8 h to provide 11 with 98.9% HPLC purity and 66% (18 g) isolated yield. $^{1-}$EINMR (400 MHz, DMSO-$d_6$): δ 8.65 (s, 1H), 8.25 (d, 1H), 7.92 (m, 1H), 7.73 (m, 1H), 3.76 (s, 1H), 3.51 (m, 2H), 3.37 (d, 2H), 2.14 (d, 2H), 1.69 (m, 2H), 1.46 (s, 9H).

Example 5: Synthesis of tert-Butyl (1-(6-(3-cyano-2-hydroxyphenyl)-3-(3,5-difluorophenyl)quinolin-4-yl)piperidin-4-yl)carbamate (13)

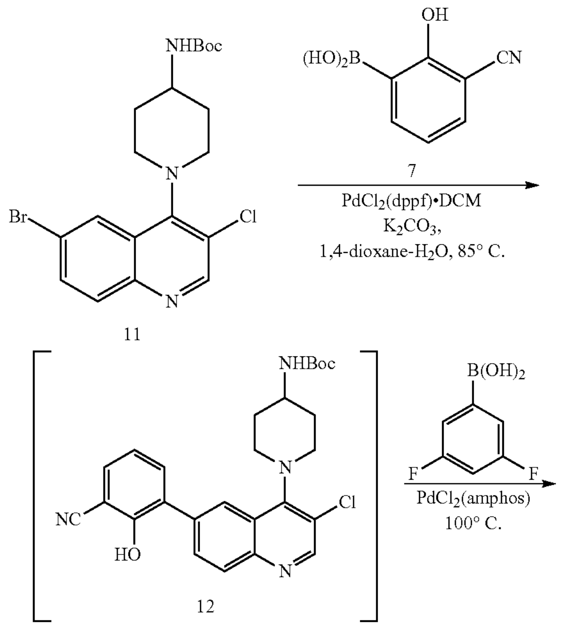

-continued

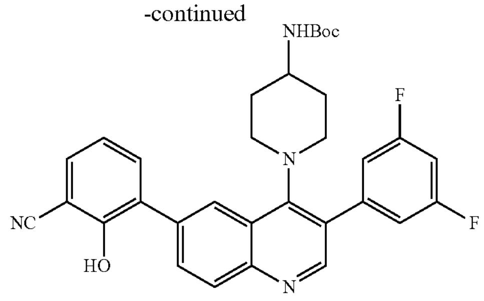

13

Quinoline 11 (350 g, 1 equiv), (3-cyano-2-hydroxyphenyl)boronic acid (Compound 7) (155 g, 1.2 equiv), and $K_2CO_3$ (438 g, 4 equiv) were charged to the round bottomed flask. 1,4-Dioxane (3.5 L, 10 vol) and DI-water (350 mL, 1 vol) were added to the flask and the resulting reaction mixture was degassed with argon for 30 min. $PdCl_2$(dppf)·$CH_2Cl_2$ (32.5 g, 0.05 equiv) was added to the reaction under argon and the mixture was degassed further for 10 min. The reaction was stirred at 80-85° C. and monitored by TLC and HPLC. After complete reaction (6 h), it was allowed to cool to 25-30° C. and 3,5-difluorophenylboronic acid (346 g, 3 equiv) was added to the reaction mixture which was then degassed with argon for 10 min. $PdCl_2$ (amphos) (25.9 g, 0.05 equiv) was added to the flask under argon atmosphere and the reaction mixture was degassed further for 10 min. The reaction was then heated to 90-100° C. and stirred for 19 h (monitored by TLC and HPLC). HPLC showed 82.04% of 13 along with 1.95% of un-reacted 12 and 0.94% of another impurity at 8.2 min. The reaction was allowed to cool to 25-30° C. and filtered through a pad of Celite and washed with ethyl acetate (1350 mL, 3 vol). The filtrate was concentrated under vacuum until ~10% solvent remained and the resulting residue was diluted with ethyl acetate (6.3 L, 18 vol), washed with water (2×3.5 L, 10 vol each), brine (3.5 L, 10 vol), and dried over anhydrous $Na_2SO_4$. The organic layer was concentrated under vacuum to dryness and was then slurried in ethyl acetate (2.1 L, 6 vol) for 4 h at RT (after 2.5 h of stirring at RT, free solid formation was observed). Resulting free solids were filtered, washed with ethyl acetate (700 mL, 2 vol) and dried under vacuum until constant weight to afford 200 g (45%) of 13 as an off white solid, which was 98.4% pure (HPLC-AUC) with approx. 3500 ppm of trace Palladium.

Example 6: Additional Purification of Compound 13

Compound 13 (200 g, 98.40% pure) was taken in IPAc (1 L, 5 vol) and refluxed for 1 h. The mixture was then allowed to cool to RT and then cooled to 15° C., filtered, washed with IPAc (600 mL, 3 vol), and dried to afford 170 g of 13 as an off white solid, which was 98.71% pure (HPLC-AUC) with approx. 50 ppm of trace Palladium.

Example 7: Removal of Residual Palladium from 13

Compound 13 (150 g, 98.71% pure) was dissolved in THF (3.4 L, 20 vol). Si-Thiol (240 g) was added and the solution stirred overnight at RT. The mixture was filtered through a Celite bed, washed with THF (510 mL, 3 vol), and concentrated under vacuum to afford a solid. The crude solid was then diluted with IPAc (1 L, 5 vol) and the slurry was refluxed for 2 h. The mixture was then allowed to cool to RT, then was cooled to 15° C., filtered, washed with IPAc (510 mL, 3 vol), and dried to afford 150 g of 13 as an off-white solid, which was 100% pure (HPLC-AUC) with no detectable residual Palladium.

Example 8: Alternative Synthesis of tert-Butyl (1-(6-(3-cyano-2-hydroxyphenyl)-3-(3,5-difluorophenyl)quinolin-4-yl)piperidin-4-yl)carbamate (13)

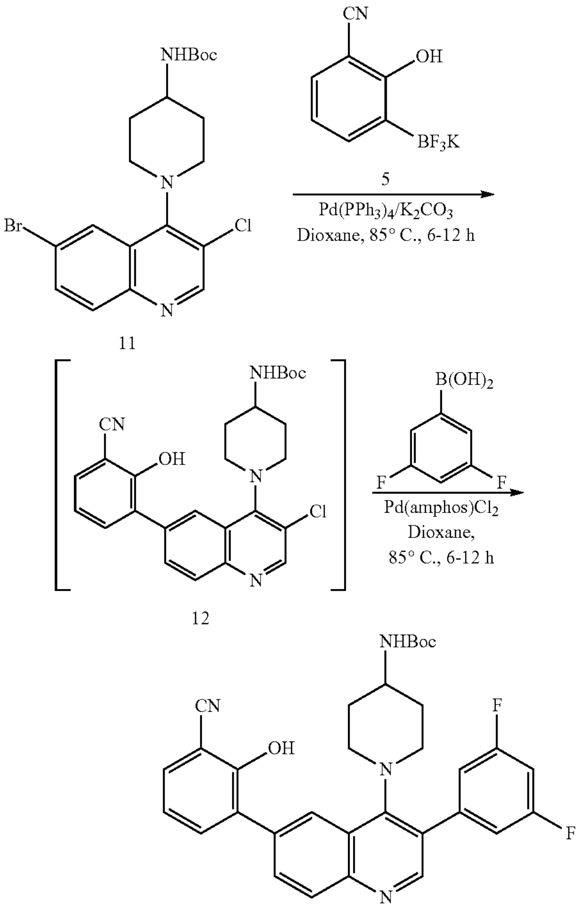

11

12

13

Compound 11 (25.0 g, 1 equiv), compound 5 (1.2 equiv), $K_2CO_3$ (3.0 equiv), 1,4-dioxane (9 vol), and purified water (0.75 vol) was added to the reaction flask. The mixture was degassed with $N_2$ bubbling before addition of $Pd(PPh_3)_4$ (0.017 equiv). Then the reaction mixture was heated to 80-85° C. for 12 h. IPC at 12 h showed <1% of Compound 11. Then 3,5 diflurophenylboronic acid (2.0 equiv), Pd(amphos)$Cl_2$ (0.03 equiv) was added and the reaction mixture was degassed again before heated up to at 90-95° C. for 6 h. IPC showed <2% of remaining Compound 11. Pure Compound 13 sample was isolated and characterized by $^1$H NMR (400 MHz, DMSO-$d_6$): δ 8.63 (s, 1H), 8.27 (bs, 1H), 7.94 (m, 2H), 7.53 (d, 1H, J=7.2 Hz), 7.47 (d, 1H, J=6.0 Hz), 6.99 (d, 1H, J=7.6 Hz), 6.77 (bs, 1H), 3.50 (m, 1H), 3.41 (m, 2H), 3.34 (m, 2H), 1.87 (m, 2H), 1.65 (m, 2H), 1.39 (s, 9H).

Workup and Pd removal: The reaction mixture was cooled to 25-30° C., filtered through celite pad. The celite pad was washed with IPAc (2.0 vol). The filtrate was combined, concentrated to 3 vol, chased with IPAc (5 vol) twice to 4 vol. The resulting solution was diluted with IPAc (8 vol) and washed with water (2×10 vol). Organic layer was separated and washed with 1% N-Acetyl L-cysteine (2×10 vol) before concentrated to 6 vol. The resulting suspension was stirred at reflux for 2 h and cooled to ambient temperature. The suspension is further cooled to 10±5° C., stirred for 2 h, and filtered. The filter cake was washed with 1 vol IPAc and dried to provide the desired crude product as pale-yellow solid.

Isolated compound 13 crude solid was dissolved in 2-methyl-THF (15 vol), added with Si-Thiol (0.25% w/w), and stirred at ambient temperature for 3 h. The suspension was filtered through celite bed, washed with 2-methyl-THF (2 vol). The above process was repeated again. The final filtrate was concentrated to 2 vol, chased with n-heptane twice (2×3 vol). The resultant suspension was filtered. The solid was dried under vacuum at 45±5° C. to afford the purified compound 13 as solid (HPLC purity 96% with Pd level of 13 ppm).

Example 9a: Alternative Synthesis of tert-Butyl (1-(6-(3-cyano-2-hydroxyphenyl)-3-(3,5-difluorophenyl)quinolin-4-yl)piperidin-4-yl)carbamate (13)

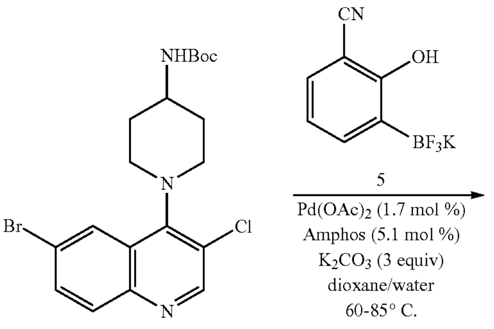

11

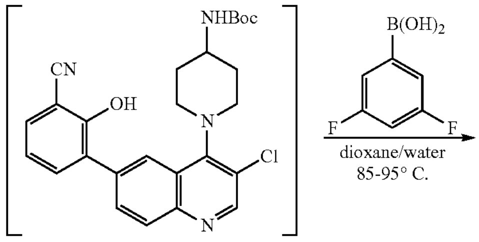

12

-continued

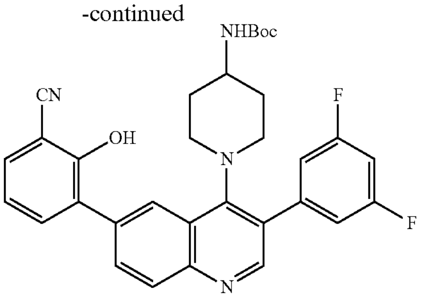

13

To a suspension of 11 (1.0 equiv), 5 (1.1 equiv), and amphos (0.051 equiv) in 1,4-dioxane (9 vol), a clear solution of $K_2CO_3$ (3.0 equiv) in water (3.0 vol) was added and degassed with argon for 30 min at ambient temperature. $Pd(OAc)_2$ (0.017 equiv) was added to the reaction under argon and degassed further for 10 min. The reaction mass was stirred at 60-85° C. for 40 min to 6 h while monitoring by TLC and HPLC. After completion of reaction as detected by HPLC, it was allowed to cool to ambient temperature. 3,5-Difluorophenylboronic acid (2.0 equiv) was charged to the pale brown clear solution of reaction mixture at ambient temperature and degassed with argon for 30 min. The reaction was then heated to 85-95° C. and stirred for 6 to 20 h while monitoring by TLC and HPLC.

The reaction mass was allowed to cool to 25±5° C. and transferred to the separating funnel (the reaction flask was rinsed with 1 vol of isopropyl acetate for complete transfer). The layers were separated and organic layer (1,4-dioxane) was concentrated to about 3.0 vol and chased with isopropyl acetate twice (5 vol each) to about 4 vol stage.

The resultant solution was diluted with IPAc (10.0 vol) and washed twice with water (2×10 vol). 1% N-acetyl-L-cysteine in water (10 vol) was added to the organic layer and stirred for 15 min before separation. 1% N-acetyl-L-cysteine treatment repeated again. The layers were filtered through a celite bed the layers were separated. The organic layer was washed with purified water (10 vol). Activated charcoal (10% w/w) was added to the organic layer at 25±5° C., stirred for 1 h, filtered through celite bed and washed with isopropyl acetate (2.0 vol). The filtrate was concentrated to 6 vol and the resultant yellow suspension heated to 80±5° C. for 1 hour. The suspension was cooled to 25±5° C. and stirred for 1 hour and further cooled to 10±5° C., stirred for 1 hour. The suspension was collected by filtration and washed with pre-cooled (5±5° C.) isopropyl acetate (1.0 vol). The solid was dried under reduced pressure at 50±5° C. for 4 hours to get crude 13 as pale yellow solid (55-56%, ~98.0% HPLC purity).

Pd Mitigation: The crude 13 was dissolved in 2-Me-THF (30.0 vol), Si-Thiol (1:0.25 w.r.t starting 11) was added and stirred for 3 h at ambient temperature, filtered on celite bed and washed with 2.0 vol of 2-Me-THF. The filtrate was concentrated to about 2 vol stage and charged 2 vol of ethanol and 2 vol of IPAc. The resultant suspension was refluxed for 6 h, cooled to 25±5° C. and stirred for 1 hour and further cooled to 10±5° C., stirred for 1 hour. The suspension was collected by filtration and washed with pre-cooled (5±5° C.) isopropyl acetate (1.0 vol). The solid was dried under reduced pressure at 50±5° C. for 4 hours to get crude 13 as a pale yellow solid (45-48%, ~99.0% HPLC purity).

Example 9b: Alternative Synthesis of tert-Butyl (1-(6-(3-cyano-2-hydroxyphenyl)-3-(3,5-difluorophenyl)quinolin-4-yl)piperidin-4-yl)carbamate (13)

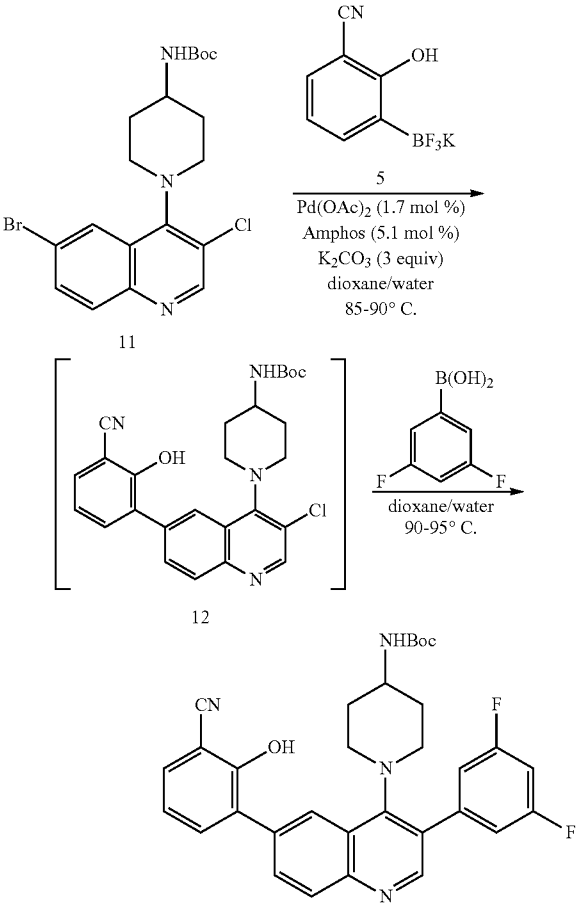

To a clean, dry 400 mL reaction vessel was charged 11 (9.96 g, 22.6 mmol, 1 eq), 5 (5.34 g, 23.75 mmol, 1.05 eq), and amphos (0.307 g, 0.051 eq). The vessel was capped and swept with nitrogen before addition of $K_2CO_3$ solution (23.7 w/w $K_2CO_3$ in water, 39.407 g, 3 eq) and 1,4-dioxane (92.3 g, 9 volumes) under inert atmosphere. The nitrogen line was lowered to sparge the biphasic solution with nitrogen for 15 minutes while mixing by overhead stirrer. While sparging, $Pd(OAc)_2$ (0.087 g, 1.7 mol %) was added. The reaction mixture was stirred while sparging at room temperature for 10 minutes. The nitrogen line was shifted to the top of the reflux condenser (cooled by chiller set to 10° C.), and the reaction vessel was heated to 60° C. to reflux (85-90° C.). Conversion was confirmed to be >95% within 30 minutes of reaching reflux, and the reaction mixture was cooled down to RT with stirring and nitrogen stream maintained throughout.

Under nitrogen stream, 3,5-difluorophenylboronic acid (7.195 g, 2 eq) was added, and the reaction mixture was sparged for 10 minutes, then heated to reflux (90-95° C.). The biphasic reaction mixture was monitored by HPLC over 10 hour reaction time and the reaction conversion reached to about 98%.

The biphasic reaction mixture was cooled to RT, transferred to a separatory funnel, and rinsed with IPAc (50 g). The organic layer was concentrated in vacuo to 3 volumes (40 g) and chased with IPAc (3×5 volumes). The thick slurry was diluted with IPAc (300 g total mass) and extracted with 100 mL $H_2O$. The hazy organic phase was treated with 1% N-acetyl-L-cysteine (10 vol) for 15 minutes and filtered through celite. The celite bed was rinsed with IPAc (20 mL) prior to separation. The hazy orange organic phase was treated with another 100 mL (10 vol) of 1% N-acetyl-L-cysteine solution. Solids crashed out of solution on top of celite bed. The celite was rinsed down with IPAc (50 mL) and 2-Me-THF (50 mL). The solution was decanted, and the solid was rinsed with IPAc to afford the first crop of product. The remaining solution was concentrated in vacuo, chased with IPAc (3×5 volumes) to 6 volumes, refluxed for 2 hours before cooled to RT and stirred overnight. The slurry was stirred at 10-15° C. for 2 hours, filtered to afford off-white solids. The cake was rinsed with 15 mL cold IPAc (ca. 0° C.) and dried in vacuo at 50° C. overnight to afford the second crop of product. Total final mass of two crops of product is 7.1 g (58% isolated yield) of off-white solid with HPLC purity of 99.5%.

Example 10: Synthesis of Crystalline Pattern B of 3-(4-(4-aminopiperidin-1-yl)-3-(3,5-difluorophenyl)quinolin-6-yl)-2-hydroxybenzonitrile dimesylate (Compound A•2MSA)

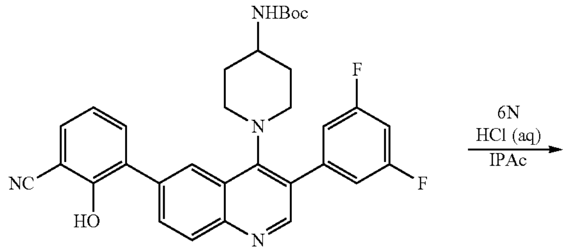

13

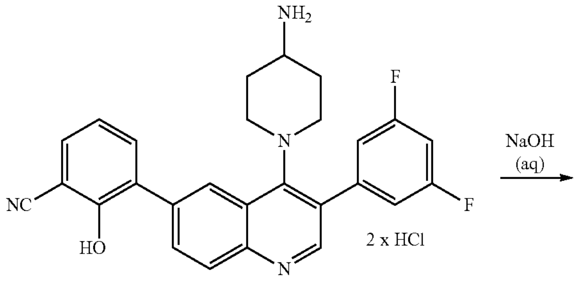

Compound A-2HCl

-continued

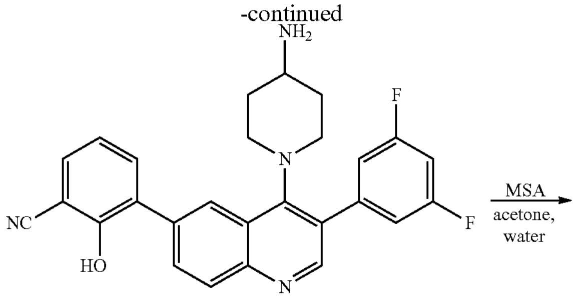

Compound A

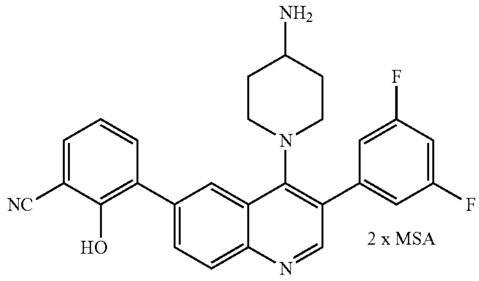

Compound A-2MSA

To a suspension of 13 (1.8 kg, 3.23 mol) in isopropyl acetate (9.0 L, 5 vol) was added 6N HCl solution (9.0 L, 5 vol) at 25±5° C. over a period of 30 minutes. To the suspension added isopropyl acetate (14.4 L, 8 vol) at 25±5° C. and stirred for 2 hours at 25±5° C. Reaction progress was monitored by TLC. After reaction completion, isopropyl acetate (5.4 L, 3 vol) was added to the reaction mixture and purged with argon gas for about 15 minutes to remove excess of HCl gas from the reaction mixture. After purging, the reaction mixture was stirred for 1 hour at 25±5° C. The solid was collected by filtration and washed with isopropyl acetate (5.4 L, 3.0 vol) and dried under reduced pressure at 45±5° C. for 12 hours to get 1.8 kg of Compound A•2HCl as a pale yellow solid with 99.18% purity by HPLC. The above solid was taken in purified water (108 L, 60 vol) and adjusted the pH to 9-10 using sodium hydroxide solution (3N) at 25±5° C. After pH adjustment, the mixture was stirred for 1 hour at 25±5° C. and filtered and washed with purified water (18 L, 10 vol) until the pH of last drop became 7 to 8. The solid was dried under reduced pressure at 55±5° C. for 12 hours to get 1.5 kg of Compound A (free base) as a pale yellow solid with 99.37% purity.

To a suspension of Compound A (free base) (1.5 kg, 3.28 mol) in acetone (9.0 L, 6 vol) at 25±5° C., is added seed (Pattern B, 6.6 g, 0.0044 w/w) and the suspension is heated to 50±5° C. for 5 min. A solution of methane sulfonic acid solution in water (1.35 L, 0.9 vol; 0.6 Kg MSA in 1.2 L water) is added to the suspension in a single lot at 50±5° C. and the resulting solutions is stirred for 10 minutes. The reaction mixture was then diluted with acetone (9.0 L, 6 vol) and stirred for 3 hours at 50±5° C. The resulting suspension was cooled to 25±5° C. and stirred for 15 minutes. The solid was collected by filtration and washed with acetone (3.0 L, 2 vol). The wet solid was dried under reduced pressure at 30±5° C. for 8 hours to get Compound A•2MSA (1.57 kg, 73% yield) as a pale yellow solid with HPLC purity 99.5%. The XRPD was consistent with Pattern B.

Example 11: Alternative Synthesis of Crystalline Pattern B of 3-(4-(4-aminopiperidin-1-yl)-3-(3,5-difluorophenyl)quinolin-6-yl)-2-hydroxybenzonitrile dimesylate (Compound A•2MSA)

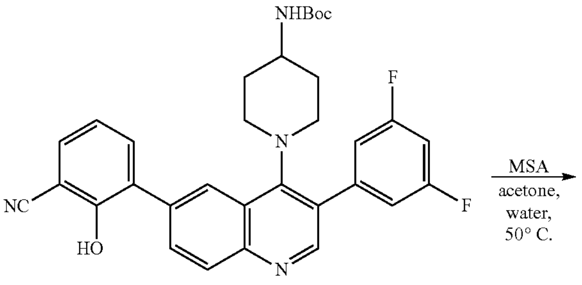

13

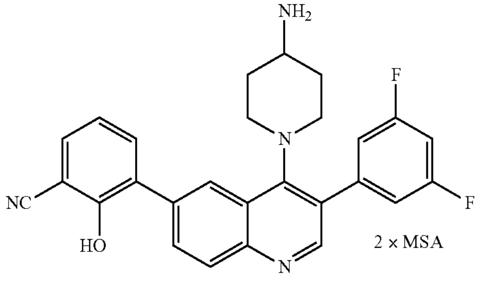

Compound A-2MSA

A suspension of 13 (1 g, 1.79 mmol) in acetone (6 mL, 6 vol.) was stirred for 5 min and heated to 45-50° C. A solution of MSA (0.58 mL, 5 equiv) in water (0.58 mL, 18 equiv) was added to the slurry at 45-50° C. The mixture was then seeded with 50 mg of Pattern B and stirred for 1.5 h at 50° C. TLC and HPLC showed complete reaction. Acetone (6 mL, 6 vol.) was slowly added to the mixture at same temperature and then allowed to cool to 25-30° C. The pale-yellow slurry was then filtered, washed with 1:10 mixture of acetone (2 mL, 2 vol.) and dried under vacuum oven at 50° C. for 3.5 h to afford 1 g of Compound A•2MSA (with 99.73% HPLC purity) as a pale yellow solid.

Synthesis of clean Pattern B by humidification: In a closed container, 1 g of above material was placed in a petri dish along with a beaker (250 mL) containing water (~200 mL, initial water temperature about 30° C. and no further temperature control needed) to create a high humidity environment. The set up was left for 24 h to expose the sample to humidity to afford 1 g of Compound A•2MSA as a pale-yellow solid. The XRPD of the resulting solid was consistent with Pattern B.

Example 12: Alternative Synthesis of Crystalline Pattern B of 3-(4-(4-aminopiperidin-1-yl)-3-(3,5-difluorophenyl)quinolin-6-yl)-2-hydroxybenzonitrile dimesylate (Compound A•2MSA)

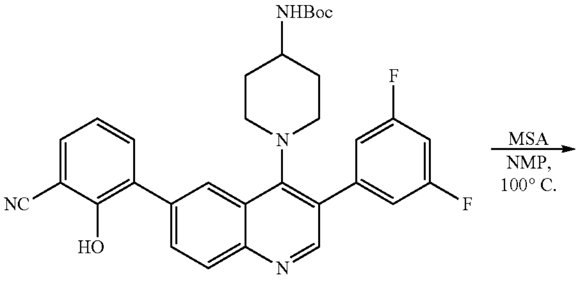

13

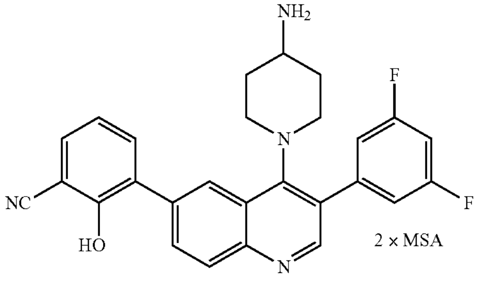

Compound A-2MSA

To a solution of 13 (2 g, 3.59 mmol) in NMP (6 mL, 3 vol.) was added MSA (1.16 mL, 5 equiv) and heated at 100° C. for 2 h. TLC and HPLC showed complete reaction. The reaction was allowed to cool to RT and stirred for another 10 h. The solids were filtered, washed with EtOAc and vacuum dried. The wet cake was slurried in EtOAc under reflux for 1 h to remove residual NMP. The mixture was allowed to cool to RT, filtered, washed with EtOAc and dried under vacuum to afford 2 g of Compound A•2MSA as pale yellow solid with unknown XRPD pattern. The solid was humidified according to above procedure to afford 2 g of Compound A•2MSA (HPLC purity: 99.62%) as pale yellow solid with an XRPD pattern consistent with Pattern B.

Example 13: Synthesis of Crystalline Pattern A of 3-(4-(4-aminopiperidin-1-yl)-3-(3,5-difluorophenyl)quinolin-6-yl)-2-hydroxybenzonitrile dimesylate (Compound A•2MSA)

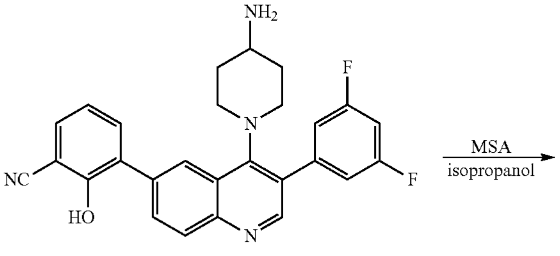

Compound A

-continued

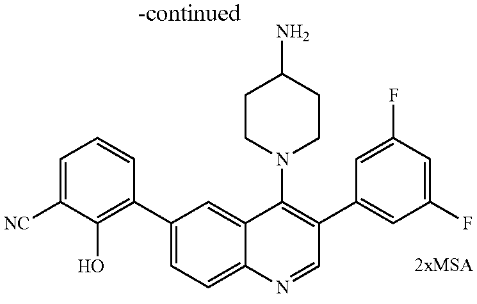

2xMSA

Compound A-2MSA

A slurry of Compound A (free base) (5 g) in isopropanol (75 mL, 15 vol.) was heated to 50-55° C. for 30 min. MSA (1.7 mL, 2.4 equiv) was added to the hot slurry and stirred for 30 min. The reaction was allowed to cool to RT and stirred for another 10 h. The solids were filtered, washed with isopropanol (2×2 vol.) and vacuum dried at 50° C. for 5 h to afford 7 g (98%) of Compound A•2MSA as pale yellow solid with an XRPD pattern consistent with Pattern A (HPLC purity: 99.68%). Karl-Fischer titration measured a water content of 1.38 wt. %.

Polymorph Screening Methods

Example A-1: Short Term Gravimetric Solubility Slurries

Short term slurries were carried out at two temperatures in 14 solvents. About 25 mg solid was added to a 2 mL vial followed by 0.70 mL of solvent. If all solids dissolved, more solid was added until a slurry was formed within reason. Slurries were stirred at constant temperature for four days (ambient temperature, 21-23° C.; or high temperature, 50° C.). After stirring for four days, solids were allowed to settle and were then recovered for XRPD analysis. XRPD analysis was performed on the wet cake, and if a new pattern was observed, the sample was dried in a vacuum oven at 50° C. for a minimum of 4 hours, then the dried sample was analyzed by XRPD.

Nine unique patterns and one pattern that was a combination of a unique pattern and an unknown pattern were recovered from the slurries. The patterns that were stable upon drying were Patterns A, B, C and I. Pattern C was recovered from EtOH, Patterns D and E converted to Pattern A upon drying, and Patterns F, G and H converted to Pattern I upon drying. Some Pattern B samples exhibited minor peak shifts at high values of 20.

TABLE 1

XRPD patterns of solids obtained from short term slurry experiments

| | XRPD Pattern | |
|---|---|---|
| Solvent | Room Temperature Slurry (21-23° C.) | High Temperature Slurry (50° C.) |
| heptane | A (wet/dry) | A |
| cyclohexane | A | A |
| Me0H | B (wet/dry) | B |
| EtOH | C (wet/dry) | C + J |
| IPA | D(wet); A (dry) | D |
| THF | E (wet); A (dry) | E |
| acetone | A | A |
| MIBK | F (wet); I (dry) | F[a] |
| Et0Ac | G (wet); I (dry) | G |

TABLE 1-continued

XRPD patterns of solids obtained from short term slurry experiments

| | XRPD Pattern | |
|---|---|---|
| Solvent | Room Temperature Slurry (21-23° C.) | High Temperature Slurry (50° C.) |
| IPAc | H (wet); I (dry) | H |
| acetonitrile | I (wet/dry) | I |
| Me0Ac* | B | B |
| acetone:water (9:1) | B+ | B+ |
| acetone:water (8:2) | B+ | |

[a]low crystallinity; *Me0Ac is saturated with water; + indicates minor peaks at 26.1 ° and 26.8 ° 20

Example A-2: Evaporative Crystallization

Supernatant from gravimetric solubility slurries was recovered for evaporative crystallization. The solutions were evaporated to dryness at 50° C. in atmosphere overnight and then placed at 50° C. under vacuum overnight (ca. 16 hours). Most vials did not contain enough solids for analysis. For those that did, the recovered solids exhibited Pattern B with the exception of EtOH, from which a new unique pattern, K, was observed. A summary of results is presented in Table 2.

TABLE 2

XRPD patterns of solids obtained from evaporative recrystallization

| | XRPD Pattern | |
|---|---|---|
| Solvent | Supernatant from RT Slurry (21-23° C.) | Supernatant from HT Slurry (50° C.) |
| MeOH | B | B |
| EtOH | K | K |
| acetone:water (9:1) | B [a] | B |
| acetone:water (8:2) | B | B [a] |

[a] low crystallinity

An additional set of evaporative crystallization experiments were performed at 50° C. with stirring. About 10 mg of Compound A•2MSA was added to a vial, the chosen solvent was added and the mixture was stirred at 50° C. In THF, acetone, and IPAc dissolution did not occur after addition of about 1900 volumes solvent. Water was added in order to dissolve the solids in THF and acetone. MeOH was used in an effort to aid the dissolution in IPAc but was unsuccessful. The solutions were uncapped and the solvent allowed to evaporate with continued stirring at 50° C. Patterns indicating low crystalline solids were obtained from the evaporated solutions. THF/water (final composition 97:3 vol.) and ACN:water (9:1 vol.) yielded Pattern B, water saturated MeOAc and acetone/water (final composition 95:5 vol.) yielded patterns that were primarily amorphous with some unidentifiable minor features. Table 3 presents a summary of data.

TABLE 3

XRPD patterns of solids obtained from evaporative recrystallization at 50° C. with stirring

| Solvent | Volumes | XRPD Pattern |
|---|---|---|
| THF:water (97:3) | 1875 | B + peak at 8.1 ° 2θ |
| acetone:water (95:5) | 1923 | amorphous + minor features |
| IPAc:MeOH (9:1) | 1842 | — |

TABLE 3-continued

| XRPD patterns of solids obtained from evaporative recrystallization at 50° C. with stirring | | |
|---|---|---|
| Solvent | Volumes | XRPD Pattern |
| ACN:water (9:1) | 490 | B [a] + peak at 8.1 ° 2θ |
| MeOAc* | 179 | amorphous + minor features |

[a] low crystallinity;

*MeOAc is saturated with water

Example A-3: Generation of Amorphous Material

About 100 mg of Compound A•2MSA was dissolved in 1 mL of ACN:water (8:2 vol.) and flash-frozen in an IPA/dry ice bath (−78° C.). The frozen solution was lyophilized overnight (~16 hrs). The resultant fluffy yellow solid was characterized by)(RFD, simultaneous TGA/DSC, modulated DSC, solution 1HNMR, and microscopy. The XRPD pattern showed a lack of crystallinity. The TGA pattern show a mass loss of 3.85% between 40 and 170° C. (FIG. 2*a*). Modulated DSC of the sample was performed. Analysis of the reversible heat flow indicates that the glass transition temperature has an onset at 166.6° C. (FIG. 1). The solution (DMSO-$d_6$) $^1$H-NMR spectrum conforms to the Compound A•2MSA structure.

A second batch of amorphous material was generated. About 350 mg of Compound A•2MSA was dissolved in 2 mL of ACN:water (8:2 vol.) and flash-frozen in liquid nitrogen (−196° C.). The frozen sample was connected to the freeze drier and kept under dynamic vacuum over the weekend (3 days). The resultant fluffy yellow solid exhibited a characteristically amorphous pattern by XRPD.

Example A-4: Slurries of Amorphous Material

About 22 mg of amorphous material was dispensed into vials and 0.5 mL (ca. 23 volumes) of the chosen solvent was added, and the mixture was stirred at room temperature (20-23° C.). A solution was formed in water and water saturated MeOAc. Additional solid was added to these solutions, but when a solution remained after roughly doubling the original solid quantity (ca. 90 mg/mL), further addition was ceased. All the other samples remained as slurries. After slurrying for 4 hours, an aliquot was taken for XRPD analysis of the slurry solids from all the samples except the water and water saturated MeOAc samples as they remained solutions. The mixtures continued to stir at room temperature overnight then the remaining slurry solids were collected (total slurry time of about 24 hours).

Amorphous material was recovered from heptane at both time points. At 4 hours, the solids recovered from EtOH slurry matched Pattern K, after 24 hours Pattern C was recovered. Pattern D was recovered from IPA slurry. Pattern I was recovered from THF (24 hours), MIBK (4 and 24 hours) and EtOAc (4 and 24 hours) slurries. Pattern F was recovered from IPAc after 24 hours. Acetone slurry yielded a new pattern, M, which lost crystallinity upon drying. ACN slurry yielded a new pattern, N, which was stable upon drying. These results are summarized in Table 4.

TABLE 4

| XRPD patterns of solids obtained from slurry experiments with amorphous material | | | |
|---|---|---|---|
| Solvent | Volumes | 4 hr | 24 hr |
| water | ~11 | dissolved | dissolved |
| heptane | 22 | Am[b] | Am |
| EtOH | 22 | K | C |
| IPA | 24 | D | D |
| THF | 24 | Am + two small peaks | I |
| acetone | 22 | M (wet); — [c] (dry) | M |
| MIBK | 23 | I | I + peak at 5.63 ° 2θ |
| EtOAc | 23 | I [a] | I + peak at 8.11 ° 2θ |
| IPAc | 21 | — [d] | F |
| ACN | 21 | N (wet/dry) | N |
| MeOAc* | ~11 | dissolved | dissolved |

[a] low crystallinity;

[b]Am = amorphous;

[c] low crystallinity with peak shifts;

[d] insufficient solids for analysis;

*MeOAc is saturated with water

Example A-5: Cooling Crystallization

About 30 mg of amorphous material was loaded into vials with stir bars. The chosen solvent was added to dissolve the solids at 50° C. THF and IPAc were unsuccessful in dissolving the solids in 20 mL, even with heating to 60° C. In THF:water (9:1 vol.) the solution separated into an oily orange layer and yellow solution. The fast-cooled samples were moved from stirring at 50° C. into an ice bath without stirring. After 3 hours without precipitation, these vials were transferred to a freezer at −20° C. No precipitation was observed the following day, the vials and are being monitored daily. The slow-cooled samples were kept stirring and the heating block temperature reduced at a rate of 5° C./hr down to room temperature. The solids that precipitated from EtOH were collected within a day and analyzed by XRPD to show Pattern K. The other samples remained solutions and were kept stirring at room temperature and are being monitored daily. Table 5 presents a summary of results.

TABLE 5

| XRPD patterns of solids obtained from the cooling crystallization experiments | | |
|---|---|---|
| Cooling Rate | Solvent | XRPD Pattern |
| Fast | EtOH | dissolved |
| | THF | — |
| | IPAc | — |
| | acetone:water (9:1) | dissolved |
| | IPA:water (9:1) | dissolved |
| | THF:water (9:1) | dissolved |
| | ACN:water (9:1) | dissolved |
| Slow (5° C./hr) | EtOH | K |
| | THF | — |
| | IPAc | — |
| | acetone:water (9:1) | dissolved |
| | IPA:water (9:1) | dissolved |
| | THF:water (9:1) | dissolved |
| | ACN:water (9:1) | dissolved |

Example A-6: Antisolvent Crystallization

Vials were loaded with about 25 mg of amorphous material which was dissolved in 5 volumes of solvent at room temperature (20-23° C.). Two antisolvent addition regimes were employed.

For direct anti-solvent addition, twice the volume of solvent was used for the anti-solvent, and this was added dropwise in 4 portions over 40 minutes. For example, if solids dissolved in 0.5 mL solvent then 1.0 mL antisolvent was added over 40 minutes.

For reverse anti-solvent addition, the solution was transferred all at once to 4 times the solvent volume of anti-solvent with rapid stirring. For example, if solids dissolved in 0.5 mL solvent then the solution was added at once to 2.0 mL antisolvent while stirring. The reverse addition experiments immediately developed into yellow slurries upon addition of the solution to the antisolvent. Pattern K was recovered from both reverse addition experiments.

A new pattern, O, was recovered from the direct addition experiments and was stable upon drying. A summary of data is presented in Table 6.

TABLE 6

XRPD patterns of solids obtained from the antisolvent crystallization experiments

| Solvent | Volumes | Antisolvent | Volumes | XRPD |
|---|---|---|---|---|
| acetone:water (8:2) | 5 | acetone | 10 | O (wet/dry) |
| acetone:water (8:2) | 5 | acetone | 20 | K |
| ACN:water (8:2) | 5 | ACN | 10 | O |
| ACN:water (8:2) | 5 | ACN | 20 | K+ |

+indicates broad peak at 20.3 ° 2θ

Example A-7: Milling Experiments

Dry and solvent drop milling was done using a small Wig-L-Bug ball mill with ¼" stainless steel ball as milling media. About 30 mg of amorphous material was weighed into a milling capsule and one volume of the chosen solvent was added. The milling was carried out in 3×30 second increments at 3500 rpm, scraping solids off the capsule walls to minimize caking between millings. The milled samples were analyzed by XRPD as a wet cake. The patterns recovered were generally of low crystallinity, the dry milled sample became amorphous.

The patterns recovered from solvent drop milling generally paired with the pattern recovered from slurries in that solvent. From ACN a combination of Patterns I and N was observed, one of which was recovered from slurry of Pattern A in ACN, the other from slurry of the amorphous in ACN. The exception was Pattern K recovered from acetone:water (9:1 vol.), the solvent system yielded Pattern B in slurries. Table 7 presents a summary of the data.

TABLE 7

XRPD patterns of solids obtained from milling experiments

| Solvent | XRPD |
|---|---|
| Dry (no solvent) | Am [b] |
| MeOH | B [a] |
| EtOH | C [a] |
| IPAc | H [a] |
| ACN | I + N [a] |
| acetone:water (9:1) | K [a] |

[a] low crystallinity;
[b] Am = amorphous

Generation of Selected Crystalline Patterns of Compound A•2MSA

Example B-1: Generation of crystalline hydrate Pattern B of 3-(4-(4-aminopiperidin-1-yl)-3-(3,5-difluorophenyl)quinolin-6-yl)-2-hydroxybenzonitrile dimesylate Compound A•2MSA (Pattern A, 0.2649 g) was added to a 20 mL vial with a stir bar. Ten volumes (2.65 mL) of acetone:water (9:1 vol.) was added and the slurry was stirred at room temperature. After about 5 minutes, the slurry had frozen and an additional 5 volumes (3.98 mL total volume) was added to form a mixable slurry. The slurry was stirred overnight (~20 hours), sampled to confirm the correct pattern was generated, then the solids were collected by filtration. The resultant pale-yellow solid was dried in a vacuum oven at 50° C. under dynamic vacuum for 2 hours, then under static vacuum overnight (~16 hours). Pattern B (0.1174 g, 44% yield) was characterized by)(RFD, solution $^1$H-NMR, simultaneous TGA/DSC, and stand-alone DSC. The solution $^1$H-NMR spectrum conformed with the structure of the dimesylate and showed 0.47 wt. % residual acetone. TGA showed a mass loss of 2.9% between 40 and 205° C. A coincident endotherm of 64 J/g (onset 86.3° C.) is observed in DSC, implying that the mass loss is water. A melting endotherm was also observed in DSC with an onset of 213.2° C. DVS was performed on Pattern B and showed a total mass difference of 3.2 wt. % over the 2-95% RH range. In the range of 10-80% RH, the mass change was 1.3 wt. %. There was no change in form after the experiment, the XRPD pattern remained Pattern B.

Crystalline Pattern B is assigned as a crystalline hydrate of 3-(4-(4-aminopiperidin-1-yl)-3-(3,5-difluorophenyl)quinolin-6-yl)-2-hydroxybenzonitrile dimesylate.

Figure 9B:
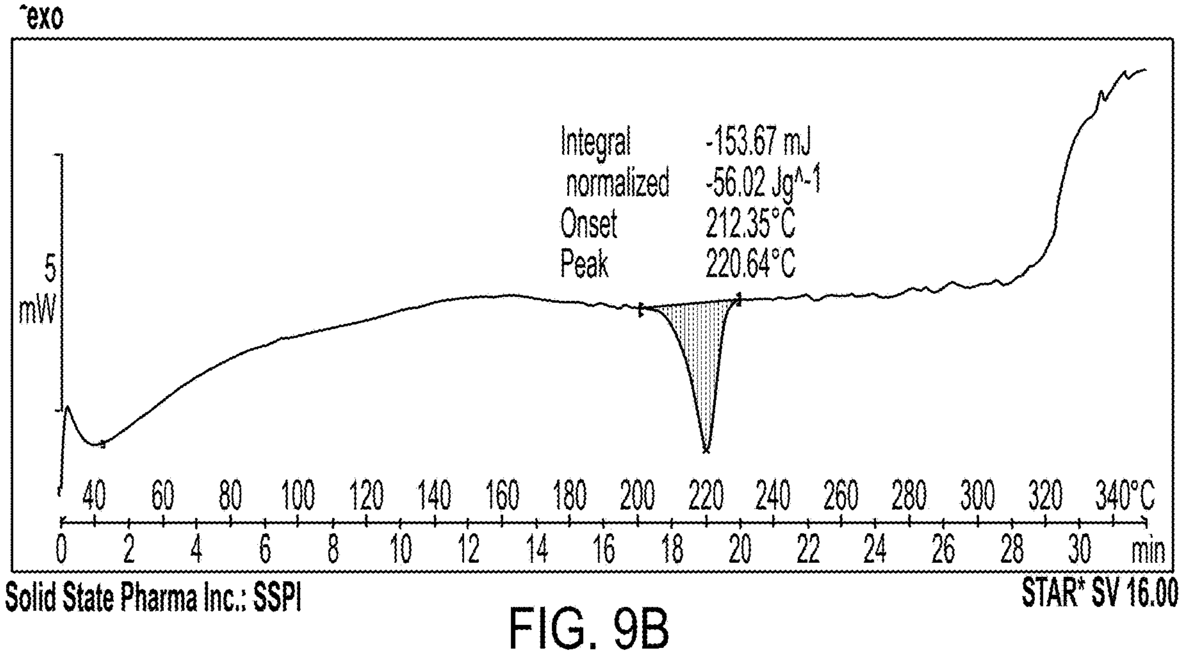
FIG. 9*b* shows the DSC thermogram of Compound A•2MSA Pattern B.

Characterization after storage under ambient conditions: Pattern B was left at ambient conditions (21-22° C., 10-40% RH) for a week then characterized by)(RFD, TGA/DSC, and water content measured by Karl-Fischer titration. The XRPD pattern is identical to Pattern B. TGA showed a mass loss of 4.23%, about an additional 1.4% water from the TGA recorded soon after removing the sample from the oven. The water content was confirmed by KF titration which yielded a value of 4.20 wt. %. An additional exotherm (onset 243.0° C.) and endotherm (onset 278.0° C.) after the melting endotherm of Pattern B (onset 205.6° C.) were observed in the DSC thermogram (FIG. 10*b*). It may be just by chance that these phase changes did not occur in the previous thermal analysis of Pattern B (FIG. 9*b*).

Stability on Drying: A sample of Pattern B was prepared on an XRPD sample holder and analysed by XRPD to create a baseline. The disk was then left in a vacuum oven at 50° C. under static vacuum for 3 days. On the third day, the sample was removed from the oven and the "dry" pattern was recorded immediately. The dry pattern matched Pattern B.

Example B-2: Alternative Generation of Crystalline Hydrate Pattern B of 3-(4-(4-aminopiperidin-1-yl)-3-(3,5-difluorophenyl)quinolin-6-yl)-2-hydroxybenzonitrile dimesylate An additional lot of Pattern B was generated by exposing Pattern A to an environment of 90%+RH at room temperature (20-23° C.) for 5 days. The humid environment was created by placing a beaker of saturated $K_2SO_4$ (aq) in a sealed container. A noticeable colour change from bright yellow to a pale, off-white/yellow was apparent. A sample was dried for an hour and then analyzed by solution $^1$H-NMR. Residual IPA was below the detectable limit by proton NMR. XRPD was consistent with Pattern B.

Example B-3: Alternative Generation of Crystalline Hydrate Pattern B of 3-(4-(4-aminopiperidin-1-yl)-3-(3,5-difluorophenyl)quinolin-6-yl)-2-hydroxybenzonitrile dimesylate Compound A (free base) (25.6 mg) was slurried in 0.153 mL (6 volumes) of acetone. The thick yellow slurry was seeded with ca. 1 mg of Pattern B. A solution of 0.518 mg/mL of MSA in water was prepared and 0.023 mL (2.2 eq.) was added to the yellow slurry bringing the solvent composition to acetone:water (85:15 vol). The slurry thinned considerably and was stirred for 1 hour at 50° C., then moved to a room temperature stirring plate to cool. The slurry thickened over the next 30 minutes and an additional 0.153 mL (6 volumes) acetone was added, bringing the solvent composition to acetone:water (92.5:7.5 vol) to generate a medium thickness pale-yellow slurry which was stirred an additional 15 minutes. The solids were collected by filtration and the wet cake was washed once with 2 volumes of acetone before drying in a vacuum oven at 50° C. for 3.5 hours. The dried solid was weighed (25 mg, 57% yield) and exhibited Pattern B by XRPD analysis.

Example B-4: Generation of crystalline Pattern C of 3-(4-(4-aminopiperidin-1-yl)-3-(3,5-difluorophenyl)quinolin-6-yl)-2-hydroxybenzonitrile dimesylate Compound A•2MSA (Pattern A, 0.2622 g) was added to a 20 mL vial with a stir bar. Fifteen volumes (3.93 mL) of EtOH was added and the slurry was stirred overnight (~20 hours). The slurry was sampled to confirm the correct pattern was generated, then the solids were collected by filtration. The resultant yellow solid was dried in a vacuum oven at 50° C. under dynamic vacuum for 2 hours, then under static vacuum overnight (~16 hours) to yield 0.2015 g (77% yield). The in-situ sample drawn was dried for 3 hours then the solid was used for characterization by solution $^1$H-NMR spectroscopy and simultaneous TGA/DSC. The bulk was dried overnight and used for stand-alone DSC, and thermal treatment. The bulk was analyzed by XRPD to generate a higher quality pattern after 6 days at ambient conditions, but this yielded a pattern resembling Pattern I.

XRPD analysis of the initial sample was consistent with Pattern C. The solution $^1$H-NMR spectrum conformed with the structure of the dimesylate. TGA showed a mass loss of 0.12% between 40 and 140° C. and a mass loss of 0.62% was observed between 140 and 290° C., with a step at 260° C. DSC showed an exotherm with an onset of 192.7° C., a broad endotherm with an onset of 252.2° C., and a melting endotherm with an onset of 296.6° C.

Pattern C is designated as an anhydrous crystalline solid of 3-(4-(4-aminopiperidin-1-yl)-3-(3,5-difluorophenyl)quinolin-6-yl)-2-hydroxybenzonitrile dimesylate.

Example B-5: Alternative Generation of crystalline Pattern C of 3-(4-(4-aminopiperidin-1-yl)-3-(3,5-difluorophenyl)quinolin-6-yl)-2-hydroxybenzonitrile dimesylate Compound A•2MSA (Pattern A) was slurried in EtOH overnight at room temperature (ca. 16 hours). A sample of the slurry solids exhibited Pattern C by XRPD. The remainder of the solids were collected, and a sample of the bulk wet-cake was analyzed by XRPD and showed Pattern C. The bulk was dried in a vacuum oven at 50° C. under dynamic vacuum for 4.5 hours. The dried solids were removed from the oven and a "dry" XRPD analysis was collected. The dry solids exhibited a pattern that was a combination of Patterns C and I. The wet sample left at ambient conditions did not change over 24 hours. Pattern C was observed to convert to I.

Example B-6: Generation of crystalline Pattern I of 3-(4-(4-aminopiperidin-1-yl)-3-(3,5-difluorophenyl)quinolin-6-yl)-2-hydroxybenzonitrile dimesylate Compound A•2MSA (Pattern A, 0.2659 g) was added to a 20 mL vial with a stir bar. Twenty-five volumes (6.65 mL) of ACN was added and the slurry was stirred overnight (~20 hours). The slurry was sampled to confirm the correct pattern was generated, then the solids were collected by filtration. The resultant yellow solid was dried in a vacuum oven at 50° C. under dynamic vacuum for 2 hours, then under static vacuum overnight (~16 hours) to yield 0.2255 g (85% yield). The sample drawn was dried for 3 hours then the solid was used for characterization by solution $^1$H-NMR spectroscopy and simultaneous TGA/DSC. The bulk was dried overnight and used for stand-alone DSC. The bulk was analyzed by XRPD to generate a higher quality pattern after 6 days at ambient conditions, but this yielded a pattern with additional peaks.

XRPD analysis of the in-situ sample was consistent with Pattern I. The solution $^1$H-NMR spectrum conformed with the structure of the dimesylate. TGA showed a mass loss of 0.19% between 40 and 185° C. and a mass loss of 0.67% between 185 and 290° C., with a step at 255° C. A few thermal events were observed in DSC in close proximity. A broad endotherm with an onset of 260.9° C. overlaps with a shoulder feature of the sharpest endotherm which had an onset of 292.6° C. Karl-Fischer titration measured a water content of 0.29 wt. %. DVS was performed (see FIG. 18). The solid converted to Pattern B during the experiment. The solids at the end of the experiment were a pale, off-white/yellow as opposed to the input Pattern I which was a bright yellow. There was a total mass difference of 9.1% on the sorption segment, and 4.6% on the desorption segment over the 2-95% RH range. In the range of 15-75% RH, the mass change was 2.5 wt. %.

Pattern I was designated as an anhydrous crystalline solid of 3-(4-(4-aminopiperidin-1-yl)-3-(3,5-difluorophenyl)quinolin-6-yl)-2-hydroxybenzonitrile dimesylate.

Analysis and Characterization Methods

Example C-1: X-Ray Powder Diffraction (XRPD)

X-ray powder diffraction was done using a Rigaku MiniFlex 600. Samples were prepared on Si zero-return wafers. A typical scan is from 2θ of 4 to 30 degrees, with step size 0.05 degrees over five minutes with 40 kV and 15 mA. A high-resolution scan is from 2θ of 4 to 40 degrees, with step size 0.05 degrees over thirty minutes with 40 kV and 15 mA. Typical parameters for XRPD are listed below.

| Parameters for Reflection Mode | |
|---|---|
| X-ray wavelength | Cu Kα1, 1.540598 Å, |
| X-ray tube setting | 40 kV, 15 mA |

-continued

| Parameters for Reflection Mode | |
|---|---|
| Slit condition | Variable + Fixed Slit System |
| Scan mode | Continuous |
| Scan range (°2TH) | 4-30 |
| Step size (°2TH) | 0.05 |
| Scan speed (°/min) | 5 |

XRPD Characterization of Solid Forms of Compound A•2MSA

The X-Ray powder diffraction pattern for the amorphous form of 3-(4-(4-aminopiperidin-1-yl)-3-(3,5-difluorophenyl)quinolin-6-yl)-2-hydroxybenzonitrile dimesylate showed a lack of crystallinity.

The X-Ray powder diffraction pattern for the crystalline Pattern A of 3-(4-(4-aminopiperidin-1-yl)-3-(3,5-difluorophenyl)quinolin-6-yl)-2-hydroxybenzonitrile dimesylate is displayed in FIG. 3. Peaks include the peaks listed in the following table:

| 2θ (degrees) | Relative intensity (a.u.) |
|---|---|
| 6.20 | 67.6 |
| 6.76 | 100.0 |
| 17.14 | 54.0 |
| 19.73 | 44.1 |
| 21.70 | 64.6 |
| 22.02 | 44.9 |
| 26.77 | 40.5 |

The X-Ray powder diffraction pattern for the crystalline hydrate Pattern B of 3-(4-(4-aminopiperidin-1-yl)-3-(3,5-difluorophenyl)quinolin-6-yl)-2-hydroxybenzonitrile dimesylate is displayed in FIG. 7. Peaks include the peaks listed in the following table:

| 2θ (degrees) | Relative intensity (a.u.) |
|---|---|
| 5.58 | 57.5 |
| 7.48 | 43.6 |
| 13.58 | 29.4 |
| 15.51 | 36.0 |
| 15.94 | 100.0 |
| 18.48 | 23.6 |
| 20.91 | 29.8 |
| 25.13 | 80.0 |

The X-Ray powder diffraction pattern for the crystalline Pattern C of 3-(4-(4-aminopiperidin-1-yl)-3-(3,5-difluorophenyl)quinolin-6-yl)-2-hydroxybenzonitrile dimesylate is displayed in FIG. 12. Peaks include the peaks listed in the following table:

| 2θ (degrees) | Relative intensity (a.u.) |
|---|---|
| 7.10 | 58.9 |
| 17.44 | 100.0 |
| 20.79 | 30.5 |
| 21.44 | 35.2 |
| 22.18 | 89.3 |
| 23.32 | 30.2 |
| 25.20 | 40.9 |

The X-Ray powder diffraction pattern for the crystalline Pattern I of 3-(4-(4-aminopiperidin-1-yl)-3-(3,5-difluorophenyl)quinolin-6-yl)-2-hydroxybenzonitrile dimesylate is displayed in FIG. 15. Peaks include the peaks listed in the following table:

| 2θ (degrees) | Relative intensity (a.u.) |
|---|---|
| 6.74 | 100.0 |
| 11.17 | 11.5 |
| 13.50 | 8.9 |
| 20.83 | 11.5 |
| 21.65 | 13.4 |
| 22.58 | 8.5 |
| 24.69 | 8.0 |

The X-Ray powder diffraction pattern for the crystalline isopropanol solvate Pattern D of 3-(4-(4-aminopiperidin-1-yl)-3-(3,5-difluorophenyl)quinolin-6-yl)-2-hydroxybenzonitrile dimesylate is displayed in FIG. 19. Peaks include the peaks listed in the following table:

| 2θ (degrees) | Relative intensity (a.u.) |
|---|---|
| 6.10 | 100.0 |
| 6.70 | 79.7 |
| 13.31 | 12.7 |
| 17.75 | 18.1 |
| 19.17 | 11.9 |
| 20.21 | 11.9 |
| 22.22 | 37.0 |

The X-Ray powder diffraction pattern for the crystalline tetrahydrofuran solvate Pattern E of 3-(4-(4-aminopiperidin-1-yl)-3-(3,5-difluorophenyl)quinolin-6-yl)-2-hydroxybenzonitrile dimesylate is displayed in FIG. 20. Peaks include the peaks listed in the following table:

| 2θ (degrees) | Relative intensity (a.u.) |
|---|---|
| 6.42 | 100.0 |
| 17.76 | 15.4 |
| 19.99 | 33.1 |
| 22.12 | 32.2 |

The X-Ray powder diffraction pattern for the crystalline methyl isobutyl ketone solvate Pattern F of 3-(4-(4-aminopiperidin-1-yl)-3-(3,5-difluorophenyl)quinolin-6-yl)-2-hydroxybenzonitrile dimesylate is displayed in FIG. 21. Peaks include the peaks listed in the following table:

| 2θ (degrees) | Relative intensity (a.u.) |
|---|---|
| 5.63 | 47.4 |
| 6.27 | 100.0 |
| 20.55 | 13.6 |
| 22.33 | 20.4 |

The X-Ray powder diffraction pattern for the crystalline ethyl acetate solvate Pattern G of 3-(4-(4-aminopiperidin-1-yl)-3-(3,5-difluorophenyl)quinolin-6-yl)-2-hydroxybenzonitrile dimesylate is displayed in FIG. 22. Peaks include the peaks listed in the following table:

| 2θ (degrees) | Relative intensity (a.u.) |
|---|---|
| 6.62 | 100.0 |
| 13.21 | 14.9 |
| 19.79 | 17.4 |
| 21.72 | 14.2 |

The X-Ray powder diffraction pattern for the crystalline isopropyl acetate solvate Pattern H of 3-(4-(4-aminopiperidin-1-yl)-3-(3,5-difluorophenyl)quinolin-6-yl)-2-hydroxybenzonitrile dimesylate is displayed in FIG. 23. Peaks include the peaks listed in the following table:

| 2θ (degrees) | Relative intensity (a.u.) |
|---|---|
| 5.66 | 100.0 |
| 10.93 | 6.7 |
| 16.77 | 9.0 |
| 22.78 | 12.4 |

The X-Ray powder diffraction pattern for the crystalline Pattern J of 3-(4-(4-aminopiperidin-1-yl)-3-(3,5-difluorophenyl)quinolin-6-yl)-2-hydroxybenzonitrile dimesylate is displayed in FIG. 24. Peaks include the peaks listed in the following table:

| 2θ (degrees) | Relative intensity (a.u.) |
|---|---|
| 6.32 | 67.2 |
| 6.72 | 100.0 |
| 7.16 | 42.1 |
| 17.50 | 32.3 |
| 21.47 | 38.7 |
| 22.31 | 33.8 |

The X-Ray powder diffraction pattern for the crystalline Pattern K of 3-(4-(4-aminopiperidin-1-yl)-3-(3,5-difluorophenyl)quinolin-6-yl)-2-hydroxybenzonitrile dimesylate is displayed in FIG. 25. Peaks include the peaks listed in the following table:

| 2θ (degrees) | Relative intensity (a.u.) |
|---|---|
| 5.42 | 100.0 |
| 7.57 | 9.0 |
| 15.90 | 40.7 |
| 18.92 | 9.8 |
| 19.59 | 16.9 |
| 21.52 | 10.5 |
| 29.48 | 8.0 |

The X-Ray powder diffraction pattern for the crystalline acetone solvate Pattern M of 3-(4-(4-aminopiperidin-1-yl)-3-(3,5-difluorophenyl)quinolin-6-yl)-2-hydroxybenzonitrile dimesylate is displayed in FIG. 27. Peaks include the peaks listed in the following table:

| 2θ (degrees) | Relative intensity (a.u.) |
|---|---|
| 5.67 | 100.0 |
| 14.63 | 59.5 |
| 16.67 | 30.3 |
| 19.70 | 33.8 |
| 22.14 | 60.8 |
| 24.46 | 39.7 |
| 24.91 | 50.9 |
| 26.35 | 33.7 |

The X-Ray powder diffraction pattern for the crystalline acetonitrile solvate Pattern N of 3-(4-(4-aminopiperidin-1-yl)-3-(3,5-difluorophenyl)quinolin-6-yl)-2-hydroxybenzonitrile dimesylate is displayed in FIG. 28. Peaks include the peaks listed in the following table:

| 2θ (degrees) | Relative intensity (a.u.) |
|---|---|
| 5.18 | 100.0 |
| 17.21 | 9.5 |
| 21.11 | 6.8 |

The X-Ray powder diffraction pattern for the crystalline hydrate Pattern O of 3-(4-(4-aminopiperidin-1-yl)-3-(3,5-difluorophenyl)quinolin-6-yl)-2-hydroxybenzonitrile dimesylate is displayed in FIG. 30. Peaks include the peaks listed in the following table:

| 2θ (degrees) | Relative intensity (a.u.) |
|---|---|
| 5.56 | 73.3 |
| 15.87 | 100.0 |
| 17.50 | 30.4 |
| 18.43 | 36.6 |
| 20.22 | 34.4 |
| 20.96 | 26.1 |
| 22.38 | 23.4 |
| 24.80 | 39.5 |

The X-Ray powder diffraction pattern for the crystalline Pattern P of 3-(4-(4-aminopiperidin-1-yl)-3-(3,5-difluorophenyl)quinolin-6-yl)-2-hydroxybenzonitrile dimesylate is displayed in FIG. 32. Peaks include the peaks listed in the following table:

| 2θ (degrees) | Relative intensity (a.u.) |
|---|---|
| 6.97 | 100.0 |
| 10.97 | 16.7 |
| 13.88 | 17.1 |
| 17.26 | 18.9 |
| 19.33 | 29.5 |
| 20.94 | 19.5 |

Example C-2: Differential Scanning Calorimetry (DSC)

Differential scanning calorimetry was done using a Mettler Toledo DSC3+. The desired amount of sample is weighed directly in a hermetic aluminum pan with pin-hole. A typical sample mass for is 3-5 mg. A typical temperature range is 30° C. to 300° C. at a heating rate of 10° C. per minute (total time of 27 minutes). Typical parameters for DSC are listed below.

| Parameters | |
|---|---|
| Method | Ramp |
| Sample size | 3-5 mg |
| Heating rate | 10.0° C./min |
| Temperature range | 30 to 300° C. |
| Method gas | $N_2$ at 60.00 mL/min |

| Parameters | |
|---|---|
| Method | Modulation |
| Sample size | 5-10 mg |
| Amplitude | 1 |
| Period | 60 s |

-continued

| Parameters | |
|---|---|
| Method | Modulation |
| Heating rate | 2.0° C./min |
| Temperature range | 30 to 350° C. |
| Method gas | $N_2$ at 60.00 mL/min |

Stand-Alone DSC Thermograms of Solid Forms of Compound A•2MSA

The modulated DSC thermogram of the amorphous solid form of 3-(4-(4-aminopiperidin-1-yl)-3-(3,5-difluorophenyl)quinolin-6-yl)-2-hydroxybenzonitrile dimesylate is displayed in FIG. 1. The modulated DSC thermogram has a glass transition temperature having an onset at about 166.6° C. and a midpoint at about 169.3° C.

The stand-alone DSC thermogram for the crystalline Pattern A of 3-(4-(4-aminopiperidin-1-yl)-3-(3,5-difluorophenyl)quinolin-6-yl)-2-hydroxybenzonitrile dimesylate is displayed in FIG. 4. The stand-alone DSC thermogram has four endothermic events having: an onset at about 78.4° C. and a peak at about 81.8° C.; an onset at about 266.1° C. and a peak at about 270.1° C.; an onset at about 281.1° C. and a peak at about 286.1° C.; and an onset at about 294.6° C. and a peak at about 297.7° C.

The stand-alone DSC thermogram for the crystalline hydrate Pattern B of 3-(4-(4-aminopiperidin-1-yl)-3-(3,5-difluorophenyl)quinolin-6-yl)-2-hydroxybenzonitrile dimesylate is displayed in FIG. 8. The stand-alone DSC thermogram has a broad endothermic event having an onset at about 86.3° C. and a peak at about 115.1° C.; and an endothermic event having an onset at about 213.2° C. and a peak at about 221.8° C.

The stand-alone DSC thermogram for the crystalline Pattern C of 3-(4-(4-aminopiperidin-1-yl)-3-(3,5-difluorophenyl)quinolin-6-yl)-2-hydroxybenzonitrile dimesylate is displayed in FIG. 13. The stand-alone DSC thermogram has an exothermic event having an onset at about 192.8° C. and a peak at about 213.3° C.; an endothermic event having an onset at about 252.2° C. and a peak at about 272.3° C.; and an endothermic event having an onset at about 296.6° C. and a peak at about 298.9° C.

The stand-alone DSC thermogram for the crystalline Pattern I of 3-(4-(4-aminopiperidin-1-yl)-3-(3,5-difluorophenyl)quinolin-6-yl)-2-hydroxybenzonitrile dimesylate is displayed in FIG. 16. The stand-alone DSC thermogram has an endothermic event having an onset at about 260.9° C. and a peak at about 274.8° C.; and an endothermic event having an onset at about 292.7° C. and a peak at about 296.0° C.

Characterization of Solid Forms of Compound A•2MSA on Thermal Treatment

Pattern A

Pattern A was heated to 277° C., monitored by DSC. The pan contents were recovered and analyzed by XRPD, exhibiting a new pattern, P. Pattern P was subsequently independently made by heating Pattern A to 255° C. This material was exposed to ~90% RH at room temperature and slurried in ACN and after 4 hours the Patterns B and I were recovered, respectively.

Pattern B

Pattern B was heated beyond the water loss and monitored by DSC. The pan was allowed to cool to room temperature then the contents were recovered and analyzed by XRPD. The pattern recovered matches Pattern B. Another sample was heated to 270° C. followed by cooling naturally to room temperature and the pan contents were analyzed by XRPD to determine what form crystallized at 250° C. The pattern is low crystalline with a few broad peaks, but seems to conform well to Pattern I. The XRPD sample was put in an atmosphere of −88% RH overnight (16 hrs) and then analyzed again. The pattern after humidity seemed to be in the process of reverting back to Pattern B.

Pattern C

Pattern C was heated to 240° C. (just beyond the exothermic event) and monitored by DSC. The pan was allowed to cool to room temperature then the contents recovered and analyzed by XRPD, indicating formation of Pattern I. Another experiment was performed where a sample was heated to 280° C., beyond the first endotherm. The pan was then allowed to cool to room temperature and the contents recovered and analyzed by XRPD. There are some differences in the intensity of a number of peaks when comparing to the pattern recovered when heating just beyond the exotherm, but the pattern still resembles pattern I.

Example C-3: Simultaneous Thermogravimetric Analysis (TGA) and Differential Scanning Calorimetry (DSC)

Thermogravimetric analysis and differential scanning calorimetry was done using a Mettler Toledo TGA/DSC3+. The desired amount of sample is weighed directly in a hermetic aluminum pan with pin-hole. A typical sample mass for the measurement is 5-10 mg. A typical temperature range is 30° C. to 300° C. at a heating rate of 10° C. per minute (total time of 27 minutes). Protective and purge gasses are nitrogen (20-30 mL/min and 50-100 mL/min).

Typical parameters for DSC/TGA are listed below.

| Parameters | |
|---|---|
| Method | Ramp |
| Sample size | 5-10 mg |
| Heating rate | 10.0° C./min |
| Temperature range | 30 to 300° C. |

Simultaneous TGA/DSC Thermograms of Solid Forms of Compound A•2MSA

Figure 2B:
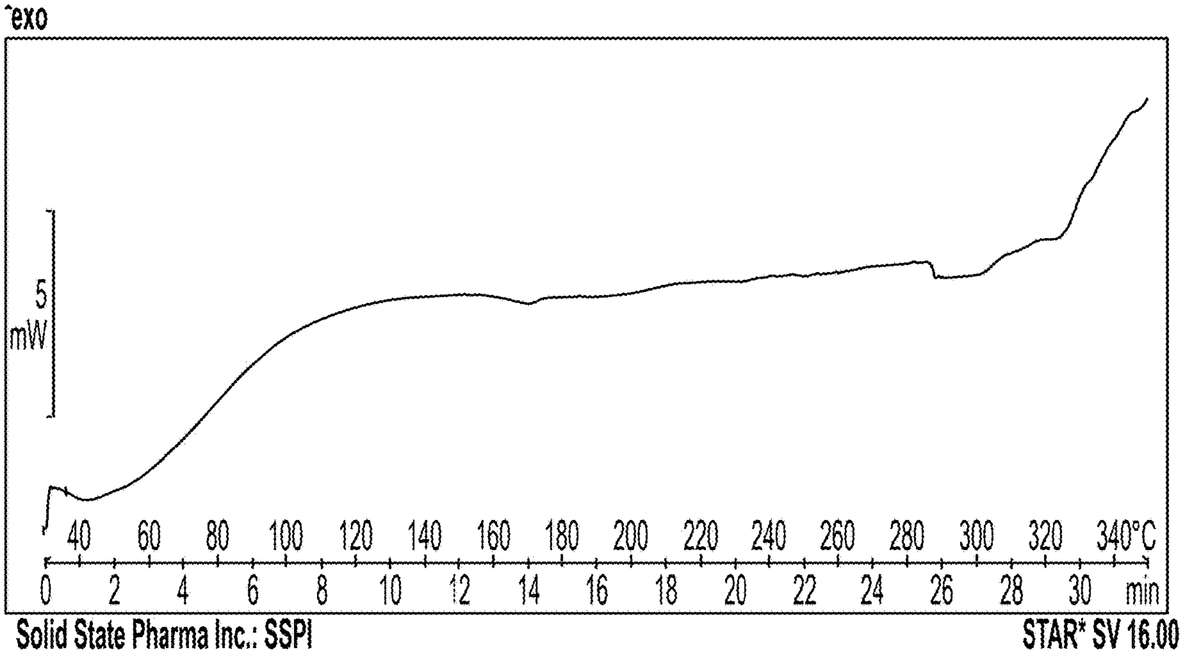
FIG. 2*b* shows the DSC thermogram of amorphous Compound A•2MSA.

The TGA pattern of the amorphous solid form of 3-(4-(4-aminopiperidin-1-yl)-3-(3,5-difluorophenyl)quinolin-6-yl)-2-hydroxybenzonitrile dimesylate is displayed in FIG. 2*a*. The thermogravimetric analysis pattern has a 3.85% w/w loss between 40 and 170° C. The DSC thermogram of the amorphous solid form of 3-(4-(4-aminopiperidin-1-yl)-3-(3,5-difluorophenyl)quinolin-6-yl)-2-hydroxybenzonitrile dimesylate is displayed in FIG. 2*b*.

Figure 5B:
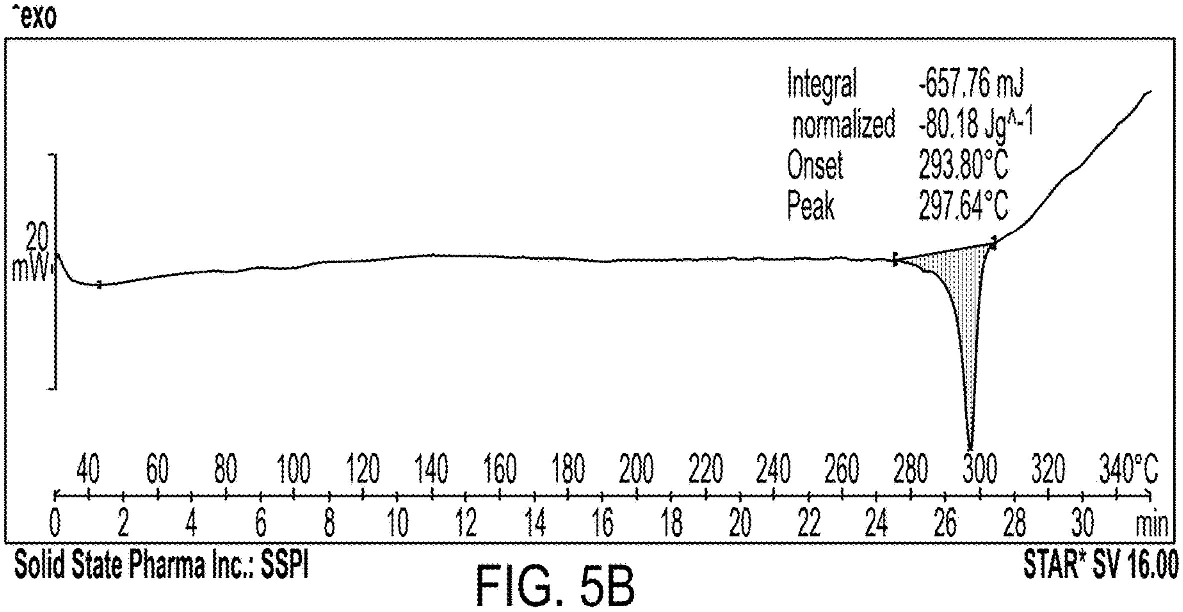
FIG. 5*b* shows the DSC thermogram of Compound A•2MSA Pattern A.

The TGA pattern of the crystalline Pattern A of 3-(4-(4-aminopiperidin-1-yl)-3-(3,5-difluorophenyl)quinolin-6-yl)-2-hydroxybenzonitrile dimesylate is displayed in FIG. 5*a*. The thermogravimetric analysis pattern has a 2.28% w/w loss from 60 to 180° C. The DSC thermogram of the crystalline Pattern A of 3-(4-(4-aminopiperidin-1-yl)-3-(3,5-difluorophenyl)quinolin-6-yl)-2-hydroxybenzonitrile dimesylate is displayed in FIG. 5*b*. The DSC thermogram has an endothermic event having an onset at about 293.8° C. and a peak at about 297.6° C.

The TGA pattern of the crystalline hydrate Pattern B of 3-(4-(4-aminopiperidin-1-yl)-3-(3,5-difluorophenyl)quinolin-6-yl)-2-hydroxybenzonitrile dimesylate is displayed in FIG. 9*a*. The thermogravimetric analysis pattern has a 2.9% w/w loss from 40 to 205° C. The DSC thermogram of the crystalline hydrate Pattern B of 3-(4-(4-aminopiperidin-1-yl)-3-(3,5-difluorophenyl)quinolin-6-yl)-2-hydroxybenzonitrile dimesylate is displayed in FIG. 9*b*. The DSC thermogram has an endothermic event having an onset at about 212.4° C. and a peak at about 220.6° C.

The TGA pattern of the crystalline hydrate Pattern B of 3-(4-(4-aminopiperidin-1-yl)-3-(3,5-difluorophenyl)quinolin-6-yl)-2-hydroxybenzonitrile dimesylate, after sitting at ambient conditions, is displayed in FIG. 10*a*. The thermogravimetric analysis pattern has a 4.23% w/w loss from 45 to 175° C. The DSC thermogram of the crystalline hydrate Pattern B of 3-(4-(4-aminopiperidin-1-yl)-3-(3,5-difluorophenyl)quinolin-6-yl)-2-hydroxybenzonitrile dimesylate, after sitting at ambient conditions, is displayed in FIG. 10*b*. The DSC thermogram has an endothermic event having an onset at about 205.6° C. and a peak at about 221.8° C.; an exothermic event having an onset at about 243.0° C. and a peak at about 254.2° C.; and an endothermic event having an onset at about 278.0° C. and a peak at about 288.2° C.

Figure 14B:
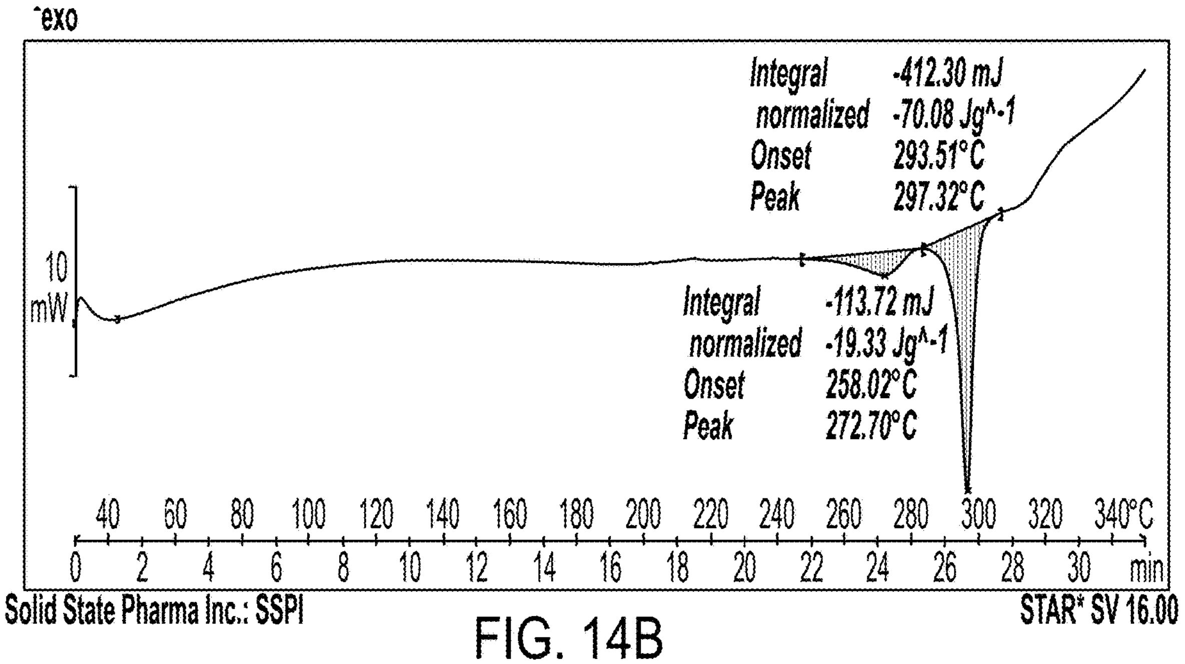
FIG. 14*b* shows the DSC thermogram of Compound A•2MSA Pattern C.

The TGA pattern of the crystalline Pattern C of 3-(4-(4-aminopiperidin-1-yl)-3-(3,5-difluorophenyl)quinolin-6-yl)-2-hydroxybenzonitrile dimesylate is displayed in FIG. 14*a*. The thermogravimetric analysis pattern has a 0.12% w/w loss from 40 to 140° C. and a further 0.62% w/w loss from 140 to 290° C. The DSC thermogram of the crystalline Pattern C of 3-(4-(4-aminopiperidin-1-yl)-3-(3,5-difluorophenyl)quinolin-6-yl)-2-hydroxybenzonitrile dimesylate is displayed in FIG. 14*b*. The DSC thermogram has an endothermic event having an onset at about 258.0° C. and a peak at about 272.7° C.; and an endothermic event having an onset at about 293.5° C. and a peak at about 297.3° C.

Figure 17B:
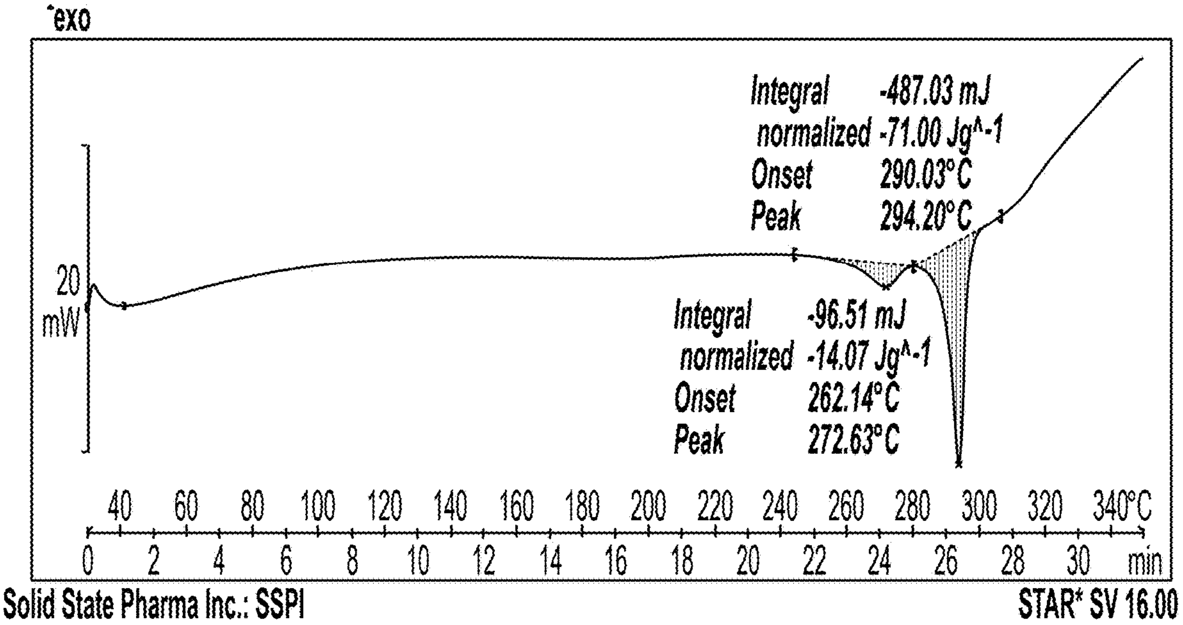
FIG. 17*b* shows the DSC thermogram of Compound A•2MSA Pattern I.

The TGA pattern of the crystalline Pattern I of 3-(4-(4-aminopiperidin-1-yl)-3-(3,5-difluorophenyl)quinolin-6-yl)-2-hydroxybenzonitrile dimesylate is displayed in FIG. 17*a*. The thermogravimetric analysis pattern has a 0.19% w/w loss from 40 to 185° C. and a further 0.67% w/w loss from 185 to 290° C. The DSC thermogram of the crystalline Pattern I of 3-(4-(4-aminopiperidin-1-yl)-3-(3,5-difluorophenyl)quinolin-6-yl)-2-hydroxybenzonitrile dimesylate is displayed in FIG. 17*b*. The DSC thermogram has an endothermic event having an onset at about 262.1° C. and a peak at about 272.6° C.; and an endothermic event having an onset at about 290.0° C. and a peak at about 294.2° C.

The TGA pattern of the crystalline Pattern K of 3-(4-(4-aminopiperidin-1-yl)-3-(3,5-difluorophenyl)quinolin-6-yl)-2-hydroxybenzonitrile dimesylate is displayed in FIG. 26*a*. The thermogravimetric analysis pattern has a 0.1% w/w loss from 40 to 190° C. and a further 0.69% w/w loss from 190 to 310° C. The DSC thermogram of the crystalline Pattern K of 3-(4-(4-aminopiperidin-1-yl)-3-(3,5-difluorophenyl)quinolin-6-yl)-2-hydroxybenzonitrile dimesylate is displayed in FIG. 26*b*. The DSC thermogram has an endothermic event having an onset at about 254.1° C. and a peak at about 271.9° C.; and an endothermic event having an onset at about 294.5° C. and a peak at about 297.7° C.

The TGA pattern of the crystalline acetonitrile solvate Pattern N of 3-(4-(4-aminopiperidin-1-yl)-3-(3,5-difluorophenyl)quinolin-6-yl)-2-hydroxybenzonitrile dimesylate is displayed in FIG. 29*a*. The thermogravimetric analysis pattern has a 5.44% w/w loss from 40 to 220° C. The DSC thermogram of the crystalline acetonitrile solvate Pattern N of 3-(4-(4-aminopiperidin-1-yl)-3-(3,5-difluorophenyl)quinolin-6-yl)-2-hydroxybenzonitrile dimesylate is displayed in FIG. 29*b*. The DSC thermogram has an endothermic event having an onset at about 132.6° C. and a peak at about 144.0° C.; an endothermic event having an onset at about 179.7° C. and a peak at about 193.5° C.; and an endothermic event having an onset at about 192.4° C. and a peak at about 211.1° C.

The TGA pattern of the crystalline hydrate Pattern O of 3-(4-(4-aminopiperidin-1-yl)-3-(3,5-difluorophenyl)quinolin-6-yl)-2-hydroxybenzonitrile dimesylate is displayed in FIG. 31*a*. The thermogravimetric analysis pattern has a 4.54% w/w loss from 40 to 260° C. The DSC thermogram of the crystalline hydrate Pattern O of 3-(4-(4-aminopiperidin-1-yl)-3-(3,5-difluorophenyl)quinolin-6-yl)-2-hydroxybenzonitrile dimesylate is displayed in FIG. 31*b*. The DSC thermogram has an endothermic event having an onset at about 206.9° C. and a peak at about 217.6° C.

Example C-4: Dynamic Vapor Sorption (DVS)

Dynamic Vapor Sorption (DVS) was done using a DVS Intrinsic 1. The sample is loaded into a sample pan and suspended from a microbalance. A typical sample mass for DVS measurement is 25 mg. Nitrogen gas bubbled through distilled water provides the desired relative humidity.

A typical measurement comprises the steps:

1—Equilibrate at 50% RH 2-50% to 2%. (50%, 40%, 30%, 20%, 10% and 2%)

a. Hold minimum of 5 mins and maximum of 240 minutes at each humidity. The pass criteria is less than 0.002% change 3-2% to 95% (2%, 10%, 20%, 30%, 40%, 50%, 60%, 70%, 80%, 90%, 95%)

a. Hold minimum of 5 mins and maximum of 240 minutes at each humidity. The pass criteria is less than 0.002% change 4-95% to 2% (95%, 80%, 70%, 60%, 50%, 40%, 30%, 20%, 10%, 2%)

a. Hold minimum of 5 mins and maximum of 240 minutes at each humidity. The pass criteria is less than 0.002% change 5-2% to 50% (2%, 10%, 20%, 30%, 40%, 50%)

a. Hold minimum of 5 mins and maximum of 240 minutes at each humidity. The pass criteria is less than 0.002% change Dynamic Vapor Sorption Isotherm Plots of Solid Forms of Compound A•2MSA The DVS isotherm plot of the crystalline Pattern A of 3-(4-(4-aminopiperidin-1-yl)-3-(3,5-difluorophenyl)quinolin-6-yl)-2-hydroxybenzonitrile dimesylate is displayed in FIG. 6. The DVS isotherm plot shows a reversible water uptake (9.8% w/w) between 2% and 95% Relative Humidity (RH).

The DVS isotherm plot of the crystalline hydrate Pattern B of 3-(4-(4-aminopiperidin-1-yl)-3-(3,5-difluorophenyl)quinolin-6-yl)-2-hydroxybenzonitrile dimesylate is displayed in FIG. 11. The DVS isotherm plot shows a reversible water uptake (3.2% w/w) between 2% and 95% Relative Humidity (RH).

The DVS isotherm plot of the crystalline Pattern I of 3-(4-(4-aminopiperidin-1-yl)-3-(3,5-difluorophenyl)quinolin-6-yl)-2-hydroxybenzonitrile dimesylate is displayed in FIG. 18. The DVS isotherm plot shows a reversible water uptake (9.1% w/w) between 2% and 95% Relative Humidity (RH); with a 2.5% w/w water uptake between 15 and 75% RH. Pattern I converts to Pattern B after DVS analysis between 2% and 95% RH and 25° C., as determined by XRPD.

Example C-5: Karl-Fischer Titration

Karl-Fischer titration for water determination was done using a Mettler Toledo C20S Coulometric KF Titrator equipped with a current generator cell with a diaphragm, and a doubleplatinum-pin electrode. Aquastar™ CombiCoulomat fritless reagent was used in both the anode and cathode compartments. Samples of approximately 0.03-0.10 g were dissolved in the anode compartment and titrated until the solution potential dropped below 100 mV. Hydranal 1 wt. % water standard is used for validation prior to sample analysis.

Results for select patterns are in the following table.

| Pattern | Water Content |
|---|---|
| A | 1.5% w/w |
| B | 4.2% w/w |
| I | 0.29% w/w |

Example C-6: Humidity Stress Tests

About 15 mg of Compound A•2MSA (Pattern A) was loaded into a 4 mL vial and the opening was covered with a Kimwipe. This was placed in a 20 mL vial with saturated aqueous $K_2SO_4$ and sealed to provide an environment of 94-96% Relative Humidity (RH) at room temperature (RT). After 3 days the solid was analyzed by XRPD and exhibited Pattern B. The sample was dried in a vacuum oven overnight and a dry XRPD pattern collected, exhibiting no change in pattern.

About 10 mg of Compound A•2MSA Pattern A and Pattern B were loaded into separate 4 mL vials. These were placed in 20 mL vials with saturated aqueous NaCl and sealed to provide an environment of 75% RH at 40° C. After one week, Pattern A had converted to Pattern B, and Pattern B remained the same. The same 1 week study was done with Pattern C (+I) and Pattern I, both remained stable by XRPD. The samples were also collected for chemical purity analysis by HPLC and did not degrade relative to the as-received material.

A summary of humidity stress tests data is presented the following table.

| Conditions | Input XRPD | Output XRPD |
|---|---|---|
| RT/96% RH/3 days | A | B |
| 40° C./75% RH/7 days | A | B |
| 40° C./75% RH/7 days | B | B |
| 40° C./75% RH/7 days | C + I | C + I |
| 40° C./75% RH/7 days | I | I |

Example C-7. Solubility in Simulated Fluids and Water

The solubility Compound A•2MSA, Patterns A, B and I, was measured in water, fasted state simulated gastric fluid (FaSSGF) and fasted state simulated intestinal fluid (FaSSIF) at 37° C. by slurrying in the respective media for 24 hours. 1.5 mL of the fluid was stirred at 37° C. About 5 mg of the specified solid was added to FaSSIF and a thin slurry was immediately formed. As a test, approximately 80 and 60 mg of Pattern A was added to 1.5 mL of water and FaSSGF, respectively without formation of a slurry. Therefore, about 10 mg of the desired Pattern was added to water and FaSSGF solutions. The samples were allowed to stir at 37° C. for 24 hrs. The stir bars were removed from the FaSSIF vials and the solids allowed to settle for 0.5 hours at 37° C. The supernatant/solutions were syringe filtered and recovered for analysis by HPLC as well as for pH measurement. Table 8 gives a summary of results.

TABLE 8

Equilibrium solubility of Compound A · 2MSA Patterns A, B and I in simulated fluids and water at 37° C.

| Pattern | Fluid | HPLC Area | Dilution | Concentration ($mg^a$/mL) | pH (24 hr) | comments |
|---|---|---|---|---|---|---|
| A | water | 28673.71 | 10× | >9.77[b] | 2.71 | dissolved |
| | FaSSGF (pH 1.70) | 30271 | 10× | >10.31[b] | 1.82 | dissolved |
| | FaSSIF (pH 6.48) | 267.36 | | 0.009 | 6.11 | disproportionated |
| B | water | 18348.03 | 10× | >6.25[b] | 3.08 | dissolved |
| | FaSSGF (pH 1.70) | 19286.83 | 10× | >6.57[b] | 1.80 | dissolved |
| | FaSSIF (pH 6.48) | 334.08 | | 0.011 | 6.02 | disproportionated |
| C | water | 19351.32 | 10× | >6.59[b] | 3.09 | dissolved |
| | FaSSGF (pH 1.70) | 22738.73 | 10× | >7.75[b] | 1.84 | dissolved |
| | FaSSIF (pH 6.48) | 305.31 | | 0.010 | 6.06 | disproportionated |

[a]mg of Compound A (free base);
[b]the highest concentration used in developing the calibration curve was 0.472 mg/mL with an area of 13789.70;
[c]the solids from FaSSIF slurries were analyzed by XRPD and yielded amorphous patterns. Proton NMR indicated that the NH+ peak at 10.7 ppm and the MSA peak at 2.3 ppm are missing for the solids recovered from FaSSIF.

Example C-8. Comparison of Compound A Mono-HCl and 2MSA in Simulated Fluids

Generation of Compound A Mono-HCl Salt

Compound A (free base, 58.9 mg) was added to 0.59 mL (10 volumes) of IPA:water (95:5) to give a yellow slurry. Concentrated HCl (12.1 M, 10.7 μL, 1 eq.) was added. The colour of the mixture changed to orange and the slurry thinned (possible dissolution). The slurry was stirred at 50° C. for 15 minutes, then transferred to a room temperature (20-23° C.) stir plate to cool for 15 minutes during which time a thick orange slurry developed. The orange solids were collected by filtration and washed twice with 1 volume of IPA:water (95:5 vol.). The solids were dried in a vacuum oven at 50° C. under static vacuum overnight (~16 hrs). 3.68 wt % IPA was detected by solution $^1$H-NMR analysis.

Alternatively, Compound A•2HCl (102.6 mg) was added to 0.51 mL (5 volumes) of IPA:water (1:1 vol.) at 45° C. to give a thick yellow slurry. Concentrated (~28 wt. %) $NH_3$ (aq.) (11 µL, 0.8 eq.) was added, some slurry on the walls of the vial turned orange. The mixture was vortexed to ensure good mixing and the slurry returned to yellow, then stirring continued at 45° C. for 10 minutes. The vial was moved to a room temperature stir plate and allowed to cool to room temperature (20-23° C.). Water (1.0 mL, 10 volumes) was added dropwise over 2 minutes to form a medium thickness slurry and this was allowed to stir overnight (~16 hrs) at room temperature. The bulk was collected by filtration and washed with 3×3 volumes of IPA:water (15:85 vol.)—the crust of the wet-cake turned orange on the second washing. The damp solids were loaded into a vial and dried in a vacuum oven at 50° C. under dynamic vacuum for 4 hours, the dry chunks were broken down after drying about 1.5 hours. 0.65 wt % IPA was detected by solution $^1$H-NMR analysis.

Kinetic Solubility Studies in FaSSIF and FeSSIF

The solubility of the dimesylate (Pattern B) and mono-HCl salts of Compound A was determined in FaSSIF (pH 6.5) at 37° C. after a slurry time of 5, 20 and 40 minutes. FaSSIF was warmed to 37° C. and added to a vial of ca. 9 mg of the salt to mark t=0. The mixture was kept stirring at 37° C. and a sample drawn with a syringe at t+5, 20 and 40 minutes. The samples were syringe filtered and the filtrate was diluted 2× to ensure no precipitation while waiting for HPLC analysis. The pH of the solution collected at 40 minutes was measured. The slurry was sampled again the following day and the supernatant from syringe filtration was analyzed directly by HPLC without dilution. The same experiment was run with FeSSIF (pH 5.0).

A summary of data is presented in Table 9. The HCl salt exhibited roughly 6× the solubility of the 2MSA salt in FaSSIF; and the 2MSA salt exhibited 12× the HCl salt solubility in FeSSIF.

TABLE 9

Solubility of Compound A HCl and 2MSA salts in FaSSIF and FeSSIF.

| | | Concentration (mg/mL) | | | |
|---|---|---|---|---|---|
| Solution | Input Solids | 5 min | 20 min | 40 min | 1 day |
| FaSSIF (pH 6.5) | Mono-HCl (3.68 wt % IPA) | 0.079 | 0.098 | 0.102 (pH: 6.45) | 0.010 |
| | 2MSA Pattern B | 0.013 | 0.015 | 0.013 (pH: 6.22) | 0.008 |
| | Mono-HCl (0.65 wt % IPA) | 0.064 | 0.081 | 0.080 | — |
| FeSSIF (pH 5.0) | Mono-HCl (0.65 wt % IPA) | 0.042 | 0.048 | 0.051 (pH: 5.05) | 0.075 |
| | 2MSA Pattern B | 0.559 | 0.565 | 0.559 (pH: 4.94) | 0.502 |

Example C-9: High-Performance Liquid Chromatography (HPLC)

High performance liquid chromatography (HPLC) was conducted using an Agilent 1220 Infinity LC. Flow rate range is 0.2-5.0 mL/min, operating pressure range is 0-600 bar, temperature range is 5° C. above ambient to 60° C., and wavelength range is 190-600 nm.

Typical parameters for DSC/TGA are listed below.

| | |
|---|---|
| Mobile Phase (A) | 0.1% TFA in 1 L Milli Q water |
| Mobile Phase (B) | Acetonitrile |
| Diluent | ACN:water (1:1) |
| Injection Volume | 5 µL |
| Monitoring Wavelength | 232 nm |
| Column | Waters X-bridge C-18, 4.6 × 150mm, 3.5 µm |
| Column Temperature | 25-26° C. |

Gradient Method:

| Step | Time (min) | Mobile Phase A (%) | Mobile Phase B (%) |
|---|---|---|---|
| 1 | 0.01 | 98 | 2 |
| 2 | 16 | 2 | 98 |
| 3 | 19 | 2 | 98 |
| 4 | 22 | 98 | 2 |
| 5 | 25 | 98 | 2 |

Example C-10: Nuclear Magnetic Resonance (NMR)

Proton NMR was done on a Bruker Avance 300 MHz spectrometer. Solids are dissolved in 0.75 mL deuterated solvent in a 4 mL vial and transferred to an NMR tube (Wilmad 5 mm thin wall 8" 200 MHz, 506-PP-8). A typical measurement is usually 16 scans.

Pharmaceutical Formulations

Example D-1: Parenteral Pharmaceutical Composition

To prepare a parenteral pharmaceutical composition suitable for administration by injection (subcutaneous, intravenous), 1-100 mg of a water-soluble salt of a compound disclosed herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example D-2: Oral Solution

To prepare a pharmaceutical composition for oral delivery, a sufficient amount of a compound disclosed herein, or a pharmaceutically acceptable salt thereof, is added to water (with optional solubilizer(s), optional buffer(s) and taste masking excipients) to provide a 20 mg/mL solution.

Example D-3: Oral Tablet

A tablet is prepared by mixing 20-50% by weight of a compound disclosed herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example D-4: Oral Capsule

To prepare a pharmaceutical composition for oral delivery, 10-500 mg of a compound disclosed herein, or a pharmaceutically acceptable salt thereof, is optionally mixed with starch or other suitable powder blends. The mixture is incorporated into an oral dosage unit such as a hard gelatin capsule, which is suitable for oral administration.

In another embodiment, 10-500 mg of a compound disclosed herein, or a pharmaceutically acceptable salt thereof, is placed into Size 4 capsule, or size 1 capsule (hypromellose or hard gelatin) and the capsule is closed.

The examples and embodiments described herein are for illustrative purposes only and various modifications or changes suggested to persons skilled in the art are to be included within the spirit and purview of this application and scope of the appended claims.

We claim:

1. A mesylate salt of 3-(4-(4-aminopiperidin-1-yl)-3-(3,5-difluorophenyl) quinolin-6-yl)-2-hydroxybenzonitrile, or solvate thereof, wherein the mesylate salt is:

an amorphous form of 3-(4-(4-aminopiperidin-1-yl)-3-(3,5-difluorophenyl) quinolin-6-yl)-2-hydroxybenzonitrile dimesylate and is characterized as having: a modulated Differential Scanning calorimetry thermogram with a glass transition temperature having an onset at about 166.6° C. and a midpoint at about 169.3° C.; a Thermogravimetric Analysis pattern with a 3.85% w/w loss between 4° and 170° C.; or a combination thereof;

a crystalline hydrate of 3-(4-(4-aminopiperidin-1-yl)-3-(3,5-difluornphenyl) quinolin-6-yl)-2-hydroxybenzonitrile dimesylate and is characterized as having an XRPD pattern with X-ray diffraction pattern reflections at about 7.10° 2-Theta, about 17.44° 2-Theta, about 22.18° 2-Theta, and about 25.20° 2-Theta as measured using Cu Kal radiation;

a crystalline isopropyl solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.10° 2-Theta, about 6.70° 2-Theta, about 17.75° 2-Theta, and about 22.22° 2-Theta as measured using Cu Kα1 radiation;

a crystalline tetrahydrofuran solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.42° 2-Theta, about 19.99° 2-Theta, and about 21.12° 2-Theta as measured using Cu Kα1 radiation;

a crystalline methyl isobutyl ketone solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.63 ° 2-Theta, about 6.27° 2-Theta, about 20.55° 2-Theta, and about 22.33 ° 2-Theta as measured using Cu Kα1 radiation;

a crystalline ethyl acetate solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.62° 2-Theta, about 13.21° 2-Theta, about 19.79 ° 2-Theta, and about 21.72° 2-Theta as measured using Cu Kα1 radiation;

a crystalline isopropyl acetate solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.66° 2-Theta, about 16.77° 2-Theta, and about 22.78° 2-Theta as measured using Cu Kal radiation;

crystalline 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.32° 2-Theta, about 6.72° 2-Theta about 12.33° 2-Theta, and about 21.47 ° 2-Theta as measured using Cu Kal radiation;

crystalline 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.42° 2-Theta, about 15.90° 2-Theta about 19.59° 2-Theta, and about 21 52° 2-Theta as measured using Cu Kal radiation;

a crystalline acetone solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.67 ° 2-Theta, about 14.63 ° 2-Theta, about 22.14° 2-Theta, and about 24.91 ° 2-Theta as measured using Cu Kα1 radiation;

a crystalline acetonitrile solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.18° 2-Theta, and about 17.21° 2-Theta as measured using Cu Kα1 radiation;

a crystalline hydrate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.56° 2-Theta, 15.87° 2-Theta, 18.43 ° 2-Theta, and about 24.80° 2-Theta as measured using Cu Kα1 radiation; or crystalline 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.97 ° 2-Theta, about 17.26° 2-Theta, about 19.33° 2-Theta, and about 20.94 ° 2-Theta as measured using Cu Kal radiation.

2. The mesylate salt of claim 1, or solvate thereof, wherein the mesylate salt is an amorphous form of 3-(4-(4-aminopiperidin-1-yl)-3-(3,5-difluorophenyl) quinolin-6-yl)-2-hydroxybenzonitrile dimesylate and is characterized as having:

a modulated Differential Scanning calorimetry thermogram with a glass transition temperature having an onset at about 166.6° C. and a midpoint at about 169.3° C.;

a Thermogravimetric Analysis pattern with a 3.85% w/w loss between 4° and 170° C.;

or a combination thereof.

3. The mesylate salt of claim 1, or solvate thereof, wherein the mesylate salt is a crystalline hydrate of 3-(4-(4-aminopiperidin-1-yl)-3-(3,5-difluornphenyl) quinolin-6-yl)-2-hydroxybenzonitrile dimesylate and is characterized as having:

an XRPD pattern with X-ray diffraction pattern reflections at about 7.10° 2-Theta, about 17.44° 2-Theta, about 22.18° 2-Theta, and about 25.20° 2-Theta as measured using Cu Kα1 radiation;

and is further characterized as having:

a Differential Scanning calorimetry thermogram with an exothermic event having an onset at about 192.8° C. and a peak at about 213.3° C.; an endothermic event having an onset at about 252.2° C. and a peak at about 272.3° C.; and an endothermic event having an onset at about 296.6° C. and a peak at about 298.9° C.;

a Thermogravimetric Analysis pattern with a 0.12% w/w loss from 40 to 140° C. and a further 0.62% w/w loss from 140 to 290° C.;

or a combination thereof.

4. The mesylate salt of claim 1, or solvate thereof, wherein the mesylate salt is a crystalline isopropyl solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.10° 2-Theta, about 6.70° 2-Theta, about 17.75° 2-Theta, and about 22.22° 2-Theta as measured using Cu Kα1 radiation.

5. The mesylate salt of claim 1, or solvate thereof, wherein the mesylate salt is a crystalline tetrahydrofuran solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.42° 2-Theta, about 19.99° 2-Theta, and about 21.12° 2-Theta as measured using Cu Kα1 radiation.

6. The mesylate salt of claim 1, or solvate thereof, wherein the mesylate salt is a crystalline methyl isobutyl ketone solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.63° 2-Theta, about 6.27° 2-Theta, about 20.55° 2-Theta, and about 22.33° 2-Theta as measured using Cu Kα1 radiation.

7. The mesylate salt of claim 1, or solvate thereof, wherein the mesylate salt is a crystalline ethyl acetate solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.62° 2-Theta, about 13.21° 2-Theta, about 19.79° 2-Theta, and about 21.72° 2-Theta as measured using Cu Kα1 radiation.

8. The mesylate salt of claim 1, or solvate thereof, wherein the mesylate salt is a crystalline isopropyl acetate solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.66° 2-Theta, about 16.77° 2-Theta, and about 22.78° 2-Theta as measured using Cu Kal radiation.

9. The mesylate salt of claim 1, or solvate thereof, wherein the mesylate salt is crystalline 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.32° 2-Theta, about 6.72° 2-Theta, about 12.33° 2-Theta, and about 21.47° 2-Theta as measured using Cu Kα1 radiation.

10. The mesylate salt of claim 1, or solvate thereof, wherein the mesylate salt is crystalline 3-(4-(4-aminopiperidin-1-yl)-3-(3,5-difluorophenyl) quinolin-6-yl)-2-hydroxybenzonitrile dimesylate and is characterized as having:

an XRPD pattern with X-ray diffraction pattern reflections at about 5.42° 2-Theta, about 15.90° 2-Theta, about 19.59° 2-Theta, and about 21 52° 2-Theta as measured using Cu Kα1 radiation;

and is further characterized as having:

a Differential Scanning calorimetry thermogram with an endothermic event having an onset at about 254.1° C. and a peak at about 271.9° C.; and an endothermic event having an onset at about 294.5° C. and a peak at about 297.7° C.;

a Thermogravimetric Analysis pattern with a 0.1% w/w loss from 40 to 190° C. and a further 0.69% w/w loss from 190 to 310° C.;

or a combination thereof.

11. The mesylate salt of claim 1, or solvate thereof, wherein the mesylate salt is a crystalline acetone solvate of 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 5.67° 2-Theta, about 14.63° 2-Theta, about 22.14° 2-Theta, and about 24.91° 2-Theta as measured using Cu Kα1 radiation.

12. The mesylate salt of claim 1, or solvate thereof, wherein the mesylate salt is a crystalline acetonitrile solvate of 3-(4-(4-aminopiperidin-1-yl)-3-(3,5-difluorophenyl) quinolin-6-yl)-2-hydroxybenzonitrile dimesylate and is characterized as having:

an XRPD pattern with X-ray diffraction pattern reflections at about 5.18° 2-Theta, and about 17.21° 2-Theta as measured using Cu Kα1 radiation;

and is further characterized as having:

a Differential Scanning calorimetry thermogram with an endothermic event having an onset at about 132.6° C. and a peak at about 144.0° C.; an endothermic event having an onset at about 179.7° C. and a peak at about 193.5° C.; and an endothermic event having an onset at about 192.4° C. and a peak at about 211.1° C.;

a Thermogravimetric Analysis pattern with a 5.44% w/w loss from 40 to 220° C.;

or a combination thereof.

13. The mesylate salt of claim 1, or solvate thereof, wherein the mesylate salt is a crystalline hydrate of 3-(4-(4-aminopiperidin-1-yl)-3-(3,5-difluorophenyl) quinolin-6-yl)-2-hydroxybenzonitrile dimesylate and is characterized as having:

an XRPD pattern with X-ray diffraction pattern reflections at about 5.56° 2-Theta, 15.87 °2-Theta, 18.43 ° 2-Theta, and about 24.80° 2-Theta as measured using Cu Kα1 radiation;

and is further characterized as having:

a Differential Scanning calorimetry thermogram with an endothermic event having an onset at about 206.9° C. and a peak at about 217.6° C.;

a Thermogravimetric Analysis pattern with a 4.54% w/w loss from 40 to 260° C.;

or a combination thereof.

14. The mesylate salt of claim 1, or solvate thereof, wherein the mesylate salt is crystalline 3-(4-(4-aminopiperidin-1-yl)-3-(3,5-difluorophenyl) quinolin-6-yl)-2-hydroxybenzonitrile dimesylate and is characterized as having an XRPD pattern with X-ray diffraction pattern reflections at about 6.97 ° 2-Theta, about 17.26° 2-Theta, about 19.33° 2-Theta, and about 20.94° 2-Theta as measured using Cu Kα1 radiation.

15. A pharmaceutical composition comprising the mesylate salt of claim 1, or a solvate thereof, and at least one pharmaceutically acceptable excipient.

16. A method of treating a disease or condition in a mammal comprising administering a mesylate salt of claim 1, or solvate thereof, to the mammal in need thereof, wherein the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

* * * * *